United States Patent [19]

Teig et al.

[11] Patent Number: 5,555,366
[45] Date of Patent: Sep. 10, 1996

[54] COMPUTER GRAPHICS SYSTEM FOR SELECTIVELY MODELLING MOLECULES AND INVESTIGATING THE CHEMICAL AND PHYSICAL PROPERTIES THEREOF

[75] Inventors: Steven L. Teig, Palo Alto; Scott D. Kahn, Los Altos, both of Calif.

[73] Assignee: MCC - Molecular Simulations, Burlington, Mass.

[21] Appl. No.: 365,677

[22] Filed: Dec. 29, 1994

Related U.S. Application Data

[62] Division of Ser. No. 732,496, Jul. 18, 1991, Pat. No. 5,386,507.

[51] Int. Cl.$^6$ .................................................. G06F 15/00
[52] U.S. Cl. ............................ 395/161; 395/159; 364/496
[58] Field of Search ..................................... 395/155–161, 395/119–127; 364/496–500

[56] References Cited

U.S. PATENT DOCUMENTS 5,249,137  9/1993  Wilson ..................................... 364/496

OTHER PUBLICATIONS

Alchemy II 1.01, Seltzer, MacWorld, Oct. 1990, p. 235.
Arduengo, A. J., III, KANVAS, E. I. du Pont de Nemours & Co., Wilmington, DE. *J. Amer. Chem. Soc.*, 1991, 113, 7071.
Hannessian, S., et al., J. Chem. Inf. Comput. Sci., 1990, 30, 413–425 "Computer Assisted Analysis and Perception of Stereochemical Features in Organic Molecules Using the Chiron Program".
Weininger, D., J. Chem. Inf. Comput. Sci., 1990, 30. 237–243 "Smile. 3. Depict. Graphical Depiction of Chemical Structures".
Nielson, G. M.; Olsen, D. R., Jr., Proceedings of 1986 Workshop on Interactive Computer Graphics, 1986, 175–182. "Direct Manipulation Techniques for 3D Objects Using 2D Locator Devices".
Chen. M., et al., Computer Graphics, 1988, 121–129, "A Study in Interactive 3–D Rotation Using 2–D Control Devices".
McCammon, J. A.; Harvey, S.C.; "Dynamics of Proteins and Nucleic Acids", Cambridge University Press: Cambridge, England (1987) 35, 36, 54–57.
Brooks, F. P., Jr., et al., Computer Graphics, 1990, 24 177–185, "Project Grope–Haptic Displays for Scientific Visualization".

*Primary Examiner*—Mark R. Powell
*Assistant Examiner*—John E. Breene
*Attorney, Agent, or Firm*—Allston L. Jones

[57] ABSTRACT

A computer graphics system for modeling chemical molecules includes simultaneous two-dimensional and three-dimensional display of models of molecules from a single data set, and allows a user to edit in either two dimensions or three dimensions. A two-dimensional model may be stylized while a three-dimensional model of the same molecule remains chemically (geometrically) correct. The system has editing tools for use in both two dimensions and three dimensions, and changes made in one mode are immediately reflected in the other, and the editing tools include manipulation components for the user to display on elements of a model, and to use to move parts of a model of a molecule relative to other parts. The system includes techniques for structure determination and display that significantly reduce the computer power required to perform system functions, rendering techniques formally reserved to supercomputers usable on smaller computer platforms. Physically based modeling is included, allowing the user to perturb the geometry of a model and to investigate interactively the effects of perturbation according to a dynamic force equation. The system also includes a procedure for displaying multiple models of molecules and performing docking studies between the models.

3 Claims, 42 Drawing Sheets

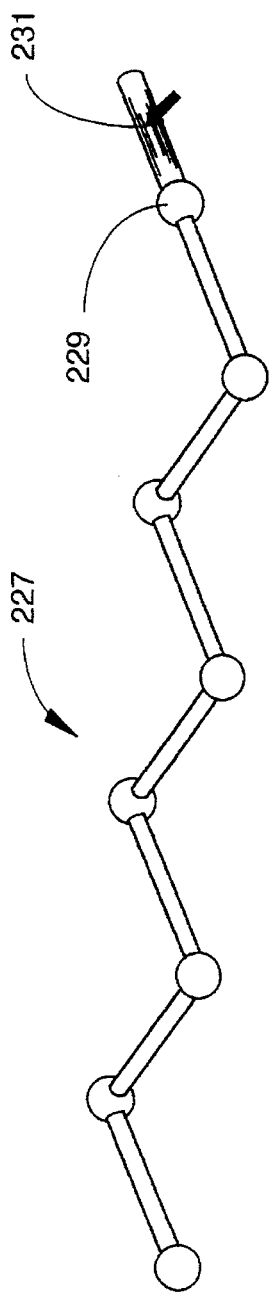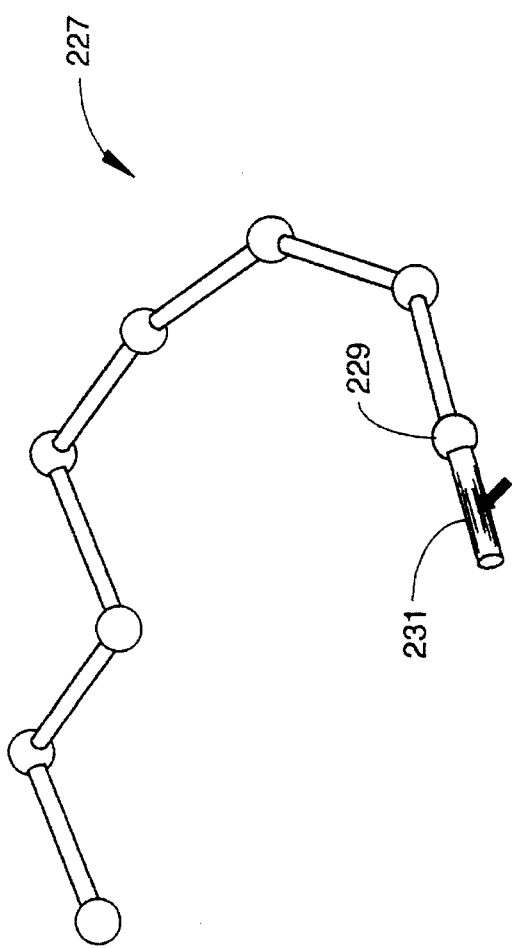
Fig. 24A
Fig. 24B

COMPUTER GRAPHICS SYSTEM FOR SELECTIVELY MODELLING MOLECULES AND INVESTIGATING THE CHEMICAL AND PHYSICAL PROPERTIES THEREOF

This is a divisional of application, Ser. No. 07/732,496, filed on Jul. 18, 1991, now U.S. Pat. No. 5,386,507.

FIELD OF THE INVENTION

The present invention relates to computerized systems for investigation of chemical compounds and techniques for using such systems. The invention has particular application in the art of synthesizing new drugs, and predicting the properties of proposed molecules.

BACKGROUND OF THE PRIOR ART

Chemical research today is the foundation of many industries, not the least of which are those that develop and market pharmaceuticals. The pharmaceutical marketplace is not only very competitive and profitable for those who are successful, but success in discovering and synthesizing new medicines also enhances the safety, health, and well being of people everywhere.

In the processes of chemical investigation, as in most other technical areas, the rapid growth of computer arts and science has brought new tools and techniques, and advanced the ability of researchers to accomplish their goals. In particular, in chemistry, computer graphics technologies have provided new ability to display and manipulate models of newly proposed chemical structures, and to study the projected physical behavior and interactions of such structures.

Even though computer techniques are being applied diligently to the needs of developmental chemists, or what have been called "bench" chemists in the art, the integration of computer techniques and traditional chemical procedures has not been without difficulty. One problem, as is true in many other fields, is that traditional chemists are not computer scientists, and have not been trained to be such. Traditional training for chemists still emphasizes, as it must, concepts of chemical bonding of atoms and molecules, the dynamics of the resulting structures, and interaction with other compounds. The computer tools that are currently available have many shortcomings, including that they are not very intuitive for persons trained in chemistry.

Although there have been advances in three-dimensional computer modeling techniques, and many have been applied to modeling the structure of chemical compounds, traditional chemistry still relies on two-dimensional representation of chemical connectivity and topology, even though the representations can only be approximate and stylized. One good reason is that textbooks are not capable of economic three-dimensional representations, particularly not dynamic representations, and the chemical literature (recorded knowledge) of the past, on which new developments of necessity must rest, is in two-dimensional representation. Moreover, over the many years of development in the chemical arts, standardized ways of representing chemical structures, bonds, and the like have been widely accepted and provide the foundation of cognition of structural similarity in the chemical sciences.

A chemist involved in a search for new compounds, for instance, gravitates to techniques that utilize two-dimensional material. Such material and technique, however, leave out a multitude of important information about a chemical structure, and some of that information can be absolutely critical to decisions shaping an investigation. For example, many chemical reactions rely on molecular shape (spatial or volumetric properties), rather than two-dimensional topology, valency, or other conventional properties. Enzyme-catalyzed reactions in biochemistry are an example. Enzymes interact with substrates as a result of complicated "lock and key" shapes that fit together—that are a partly a function of three-dimensional molecular shape.

A related difficulty stems from the fact that chemical compounds do not exist in just a single geometric conformation. Many molecular bonds are not static and immovable, but rather are rotatable and stretchable, giving rise to many different geometric arrangements (conformers) for a compound, some more stable than others. Where there are rotatable bonds, the number of conformers is infinite.

The very large number of different geometric conformations that molecules may assume cannot be safely ignored in any chemical investigation, because of the complex relationship between the different conformers and the observed reactivity, efficacy, etc. of a compound. Moreover, the conformational changes are extremely rapid, and a molecule typically assumes many different conformations over periods of time measured in pico-seconds. The study and investigation of such perturbations is called molecular dynamics, and lends itself handily to statistical analysis and computer techniques. A typical procedure in molecular dynamics involves many hours of supercomputer time to simulate and analyze changes that occur in a molecule in a pico-second.

One way that computers have been incorporated into chemical investigation has been by interaction between bench chemists and specialists trained and experienced in computer graphics and molecular dynamics. A single research organization, for example, might have traditional synthetic/medicinal chemists engaged in studying problems and proposing chemical solutions, such as new compounds to be synthesized. In another department, trained computer molecular modelers accept information from the traditional chemists and perform molecular modeling and dynamics studies.

Such cooperative approaches have had some success, but generally suffer from communications difficulties. Perhaps more importantly the research chemist is distanced from tools that could provide valuable insight on a moment-to-moment basis and which could more positively influence the direction and impact of a study.

Another approach used by the bench chemist to query three-dimensional chemical structures has been the use of metal and plastic physical models of molecules and compounds, connected by mechanisms that represent to some degree the natural connections. Springs can be used, for example, to preload structures and represent the forces inherent in a molecular system. Flexible materials are also useful. Such physical models have an advantage of hands-on feel, and are easily rotated, translated, and manipulated. As the size of a structure under scrutiny increases, however, such physical models become unwieldy and cumbersome, and the forces acting on various parts of a molecule are increasingly difficult to perceive, even approximately. Moreover, such models have no mechanism for representing the energy of various geometries of a molecular structure, and hence no way to incorporate molecular dynamics in a really useful way. The plastic and metal models also have no convenient mechanism for representing Van der Waals or electrostatic forces.

Yet another difficulty with techniques of the prior art is that where attempts have been made to computerize modeling and dynamics, the complexity of molecular structures and the forces between atoms in the molecules has required computers of considerable power and sophistication to provide modeling. There has been but little progress in reducing the magnitude of computer power needed to accomplish useful modeling techniques.

What is clearly needed to overcome these many difficulties is a comprehensive computerized system that allows a bench chemist to use both two-dimensional and three-dimensional representations, allowing input in either format, storing data for both formats, and updating displays in both formats as data changes. Ideally, such a system needs to come as close to "hands-on" manipulation as possible. The user, who will frequently be called the investigator in this specification, must be able to work in either the two-dimensional or the three-dimensional format as the need arises for a single situation, choosing that format that has the best advantage for the moment, and best matches the mental process of the investigator at that point in time. For example, setting up a structure from more elemental forms, such as assembling a compound from traditional ring structures, common substituent groups, and atoms, is best done in a two-dimensional format, following the traditional connectivity standards known in the art. Examining the volumetric shapes of a resulting structure is best done in a three-dimensional format with an ability to rotate, translate, and otherwise manipulate the model.

A system to be very useful directly by a bench chemist should comprise a facility for allowing the chemist to manipulate portions of a connected structure, such as rotating and bending bonds, within the constraints imposed by the known connective chemistry and the forces attendant according to the laws of physics relative to the structure. Moreover, as such manipulation is accomplished, the system should readily determine relative energies and related stability of the new physical configurations resulting from the manipulation. This facility would allow a chemist a truly interactive method for investigating alternative conformers of a compound without the time-consuming and very expensive application of supercomputer hardware, massive computational techniques, and employment of computer applications experts common to the current art of molecular modeling.

Another desirable feature of such a system would be an ability to display more than one molecule simultaneously and to allow a user to study docking characteristics relative to the displayed molecules, such as "lock and key" complementarity.

SUMMARY OF THE INVENTION

In accordance with the present invention a computer graphics system is provided for selectively modeling molecules and investigating chemical and physical properties of molecules. The system includes a processor; a control means coupled to the processor for directing operation of the system; a memory means also coupled to the processor for storing data relative to known atoms, to molecules, and to known influences between atoms in molecules; input means coupled to the processor for a user to enter data relative to selection of information from the memory means and for providing user commands to direct operation of the control means; and monitor means coupled to the processor to provide a display of information and models of the atoms and molecules selected by the user via the input means. The control means provides the user an ability to act interactively with the display on the monitor means, and the display has both a first portion for displaying a two-dimensional model of a selected molecule and a second portion for displaying a three-dimensional model of the same molecule. The first and second portions are displayable at the same time on the monitor means.

The simultaneous display of two-dimensional and three-dimensional models allows the user to use the mode that presents the best advantage for a given circumstance. To avoid possibility of error between the models, only one data set is used for each molecule selected to display, storing a single topology for a molecule. Both models originate from the single data set, and edits done in either mode change the single data set, so changes made in one mode are immediately reflected in the other mode.

There is a periodic table for a user to select atoms, and the table includes user-definable and alterable menus of molecular entities for use as building blocks to construct and display molecules. The periodic table also has a selection of coordination geometries to extend choices for addition of entities to existing models.

There is in the present invention a wide selection of editing techniques as tools for a user to accomplish editing goals. The two-dimensional display can be stylized by moving atomic centers in a molecule to apparent positions that would not be naturally occurring, which is a considerable aid in certain studies, and there is a clean-up function for causing the two-dimensional display to revert to a more standard display, which can be set up according to rules that a user can tailor to their specific needs.

For convenience the total display area can be altered and the relative portion used by the two-dimensional display and the three-dimensional display can be adjusted as well.

There is provided a unique ability to display manipulation elements, pictured as knurls and handles in the present invention, upon elements of a three-dimensional model for user interaction to perturb the geometry of a model. The knurls and handles provide an intuitive procedure for perturbation to investigate alternate conformers for molecular models, and the effects of alternate conformers on chemical characteristics. The control procedures provided allow deformation to be displayed as continuous movement in real time. The knurl perturbation techniques include two-handed manipulation.

There is also disclosed in the present invention a unique procedure, allied with the intuitive deformation techniques, for the accounting and displaying of restoring forces, energy, and strain while deforming a model of a molecule.

The method is termed physically-based modeling, and involves evaluation and determination using force field functions relative to atomic center positions in a model of a molecule, and, in some cases, between atoms in separate models of molecules. Physically-based modeling can be turned off, in which case deformations are determined and displayed as though there were no interactions between the atoms of a molecule, or turned on, in which case the system accounts for all of the interactions. With physically-based modeling turned on, the system can report steep gradients in deformation with colors, audio feedback, and tactile feedback.

There are also disclosed unique procedures with physically-based modeling for determining inter-molecular interactions such as Van der Waals forces and electrostatic forces, to minimize computation time, hence needed computer power, which makes the system viable for reasonably-sized computer platforms.

Also there is an investigative technique disclosed using the functions of the system to study docking behavior. In the present invention docking is investigated by displaying two (or more) molecules, which appear in both the two-dimensional and the three-dimensional displays. The two-dimensional display is used to identify areas of interest on the models for docking behavior, and to enter interatomic distance constraints. The use of the two-dimensional display is advantageous because of the provided ability to stylize the two-dimensional display, moving parts of a model aside that might occlude the parts of interest, and enhancing the display of areas of the models of interest for docking. Once constraints are entered in 2-dimensions, the system performs the docking and displays (if possible) the models in the constrained relationship in the three-dimensional display.

The system of the invention provides an intuitive computer laboratory with capabilities for chemical investigations far beyond those of any system available previously for the same or similar kinds of studies. In so doing, the system of the invention also solves the problem of communication between bench chemists and computer experts, because the system is intuitive and easily understood and thus used by the bench chemist.

BRIEF DESCRIPTION OF THE DRAWING FIGURES

FIG. 24A shows a model of a chain-type molecule with a handle manipulation element attached to one atom of the molecule.

FIG. 24B shows the model of FIG. 24A in a different conformer as a result of perturbing the geometry with the handle.

Figure 29A:
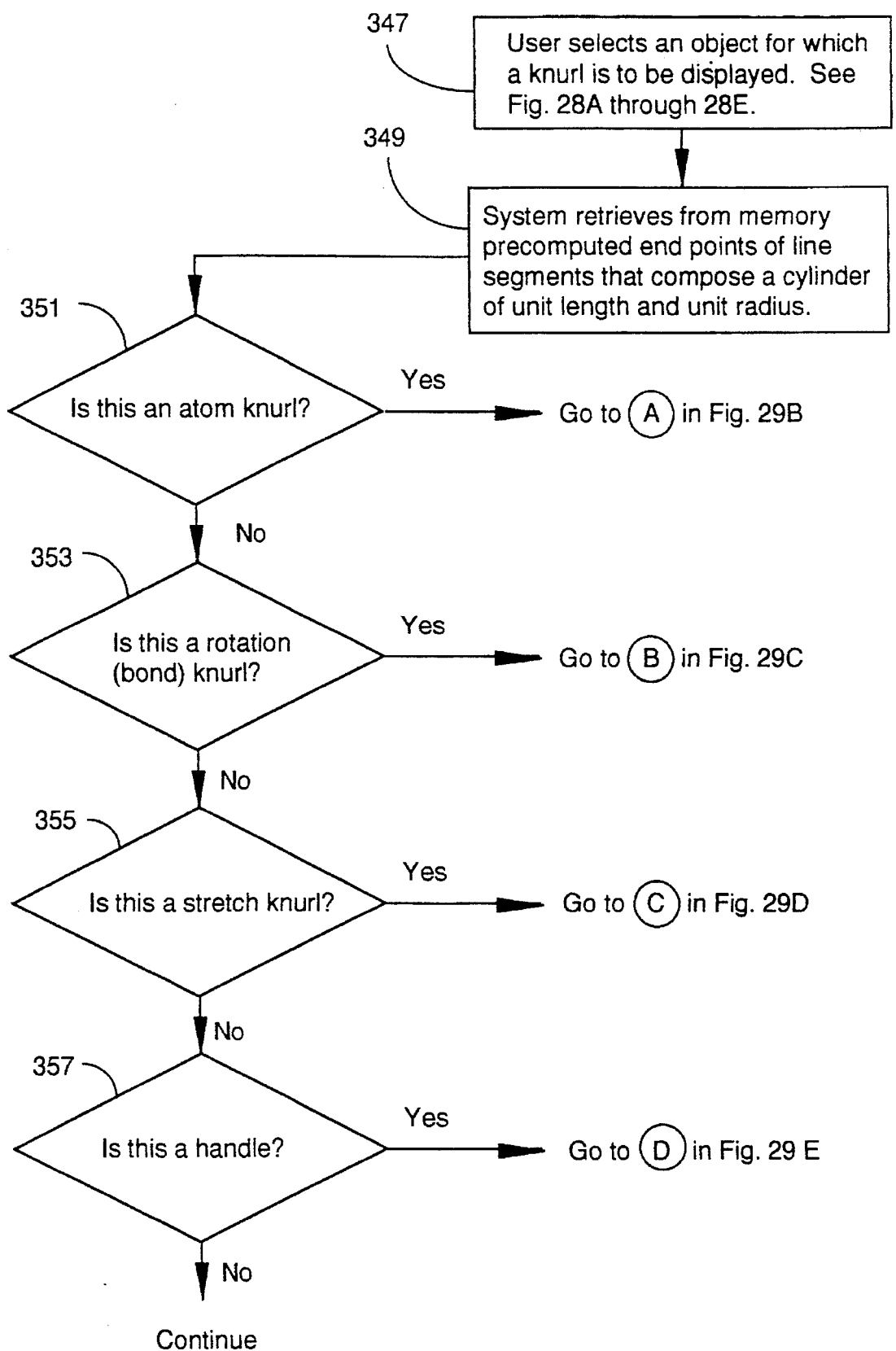
FIG. 29A is a flow diagram showing the mechanism by which the system scales and displays knurls.
Figure 29B:
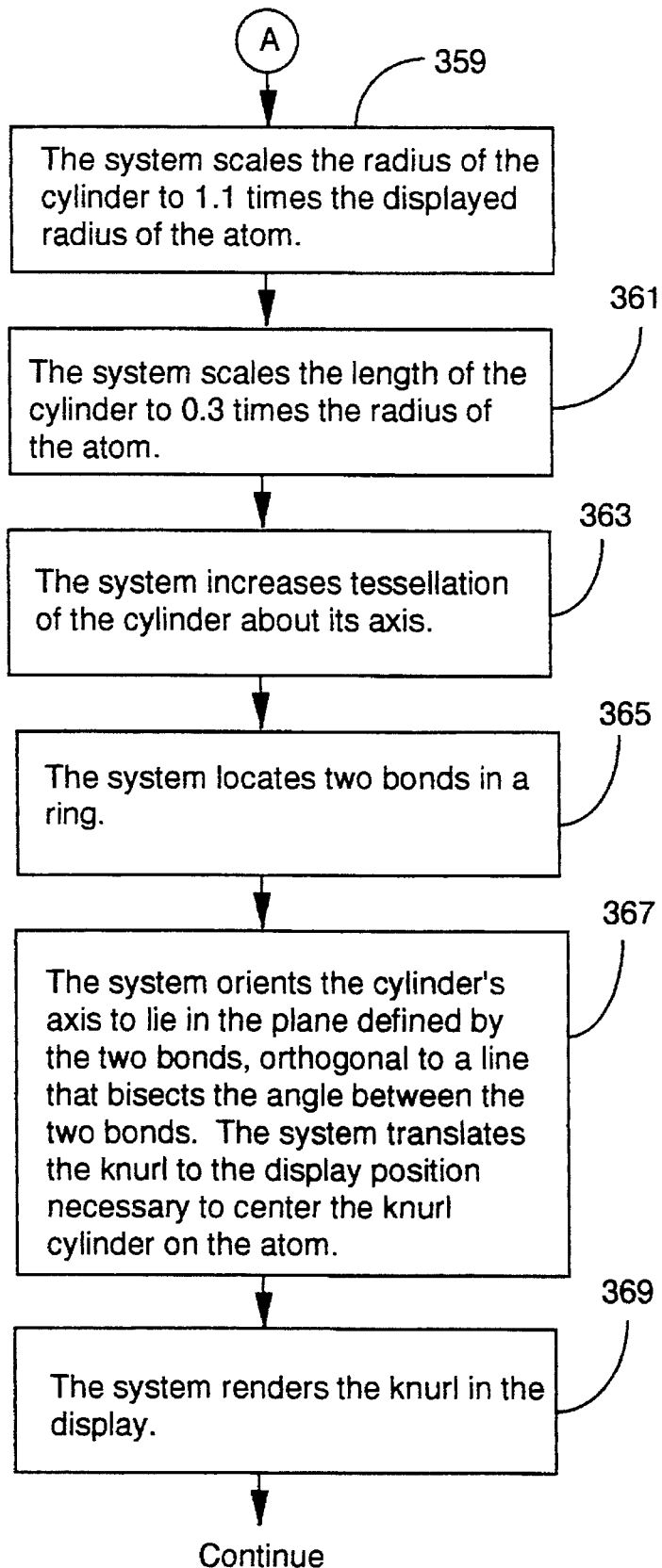
FIG. 29B is a flow diagram enlarging on FIG. 29A.
Figure 29C:
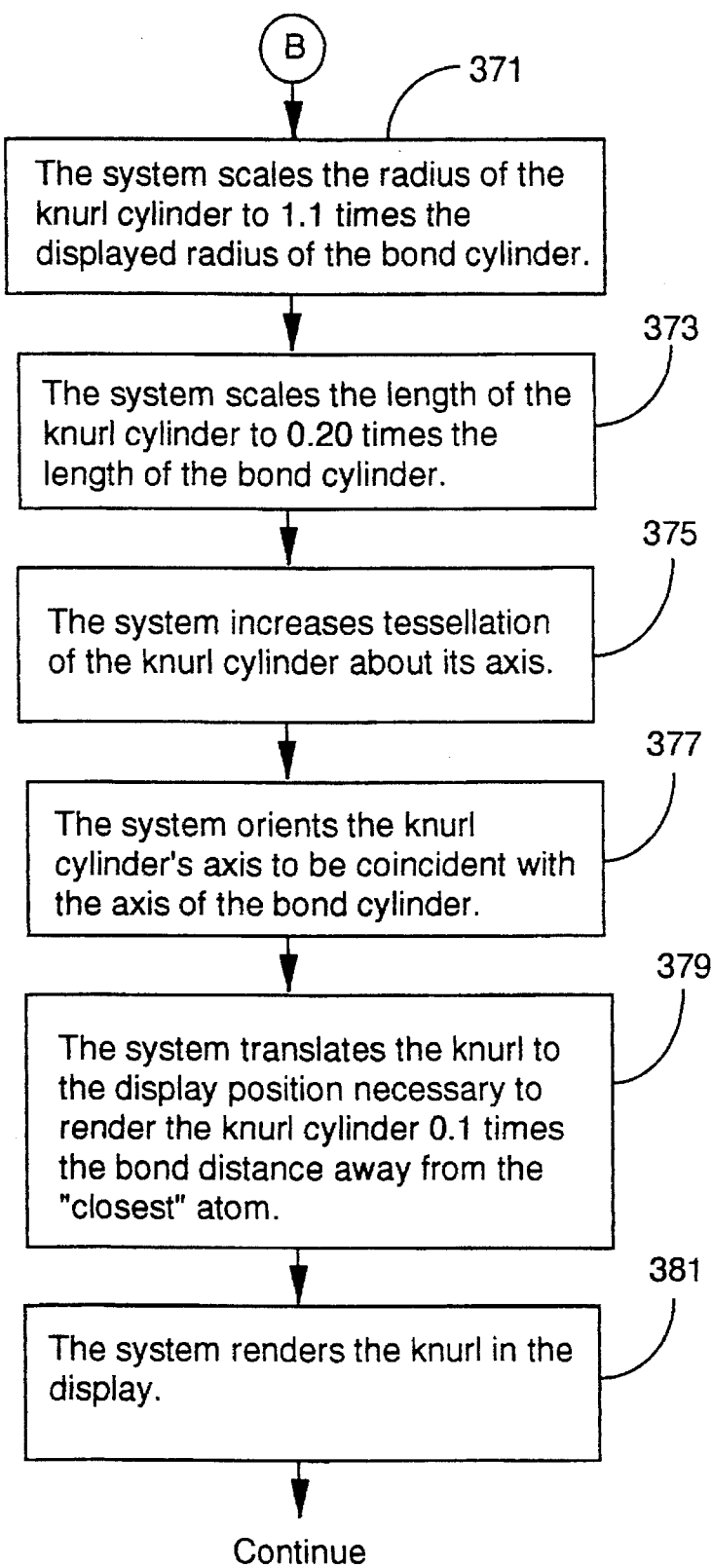
FIG. 29C is a flow diagram enlarging on FIG. 29A.
Figure 29D:
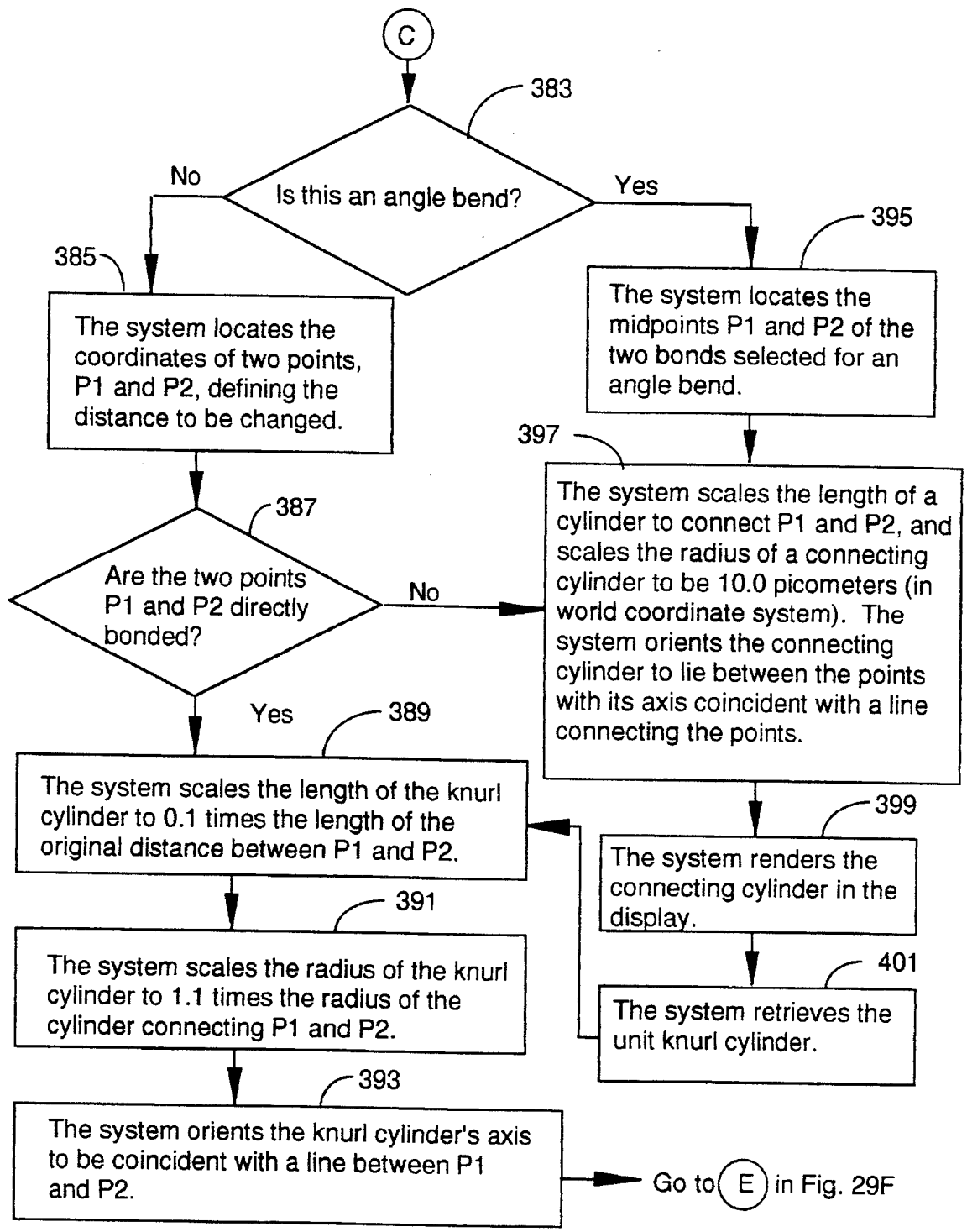
Figure 29E:
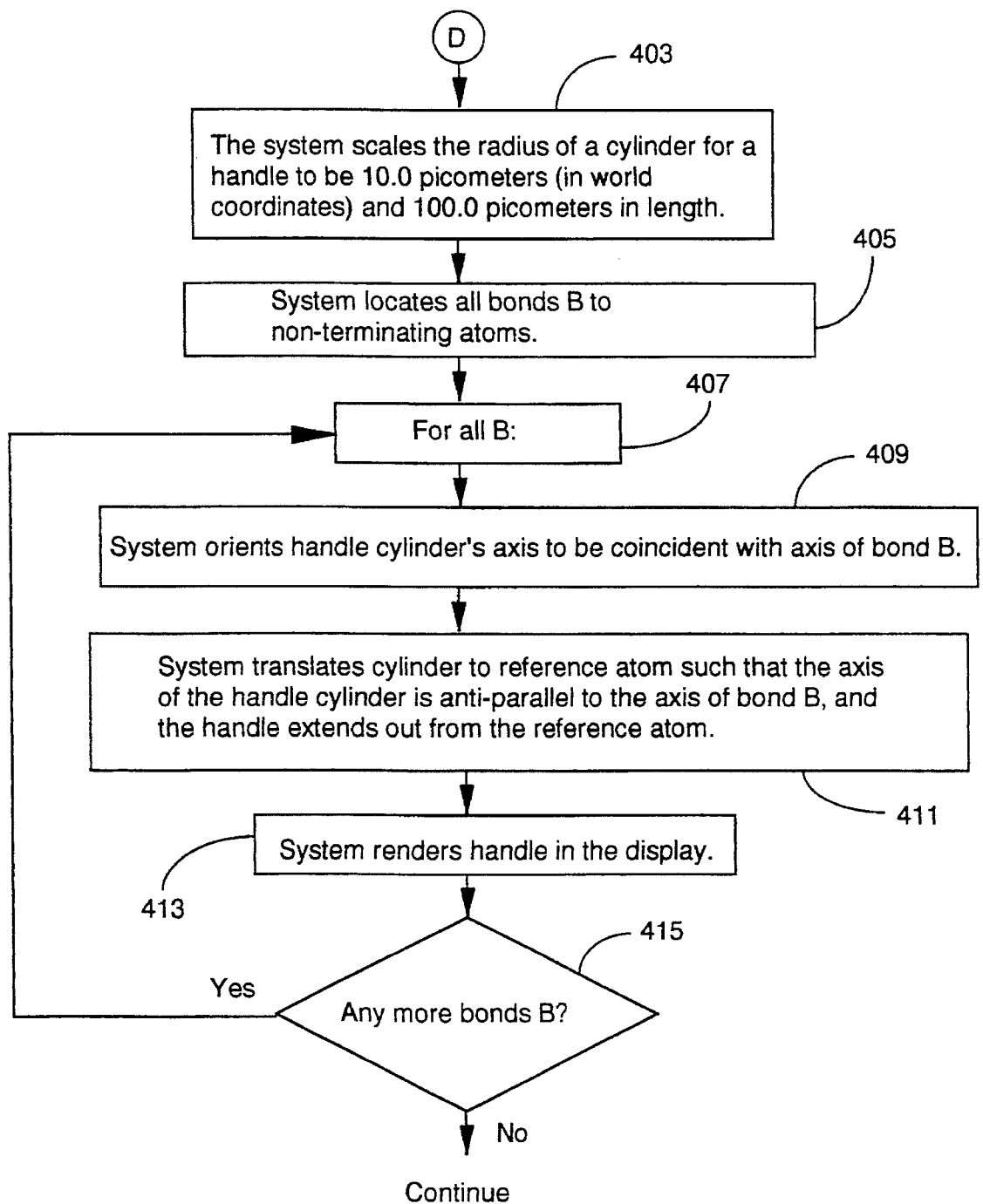
Figure 29F:
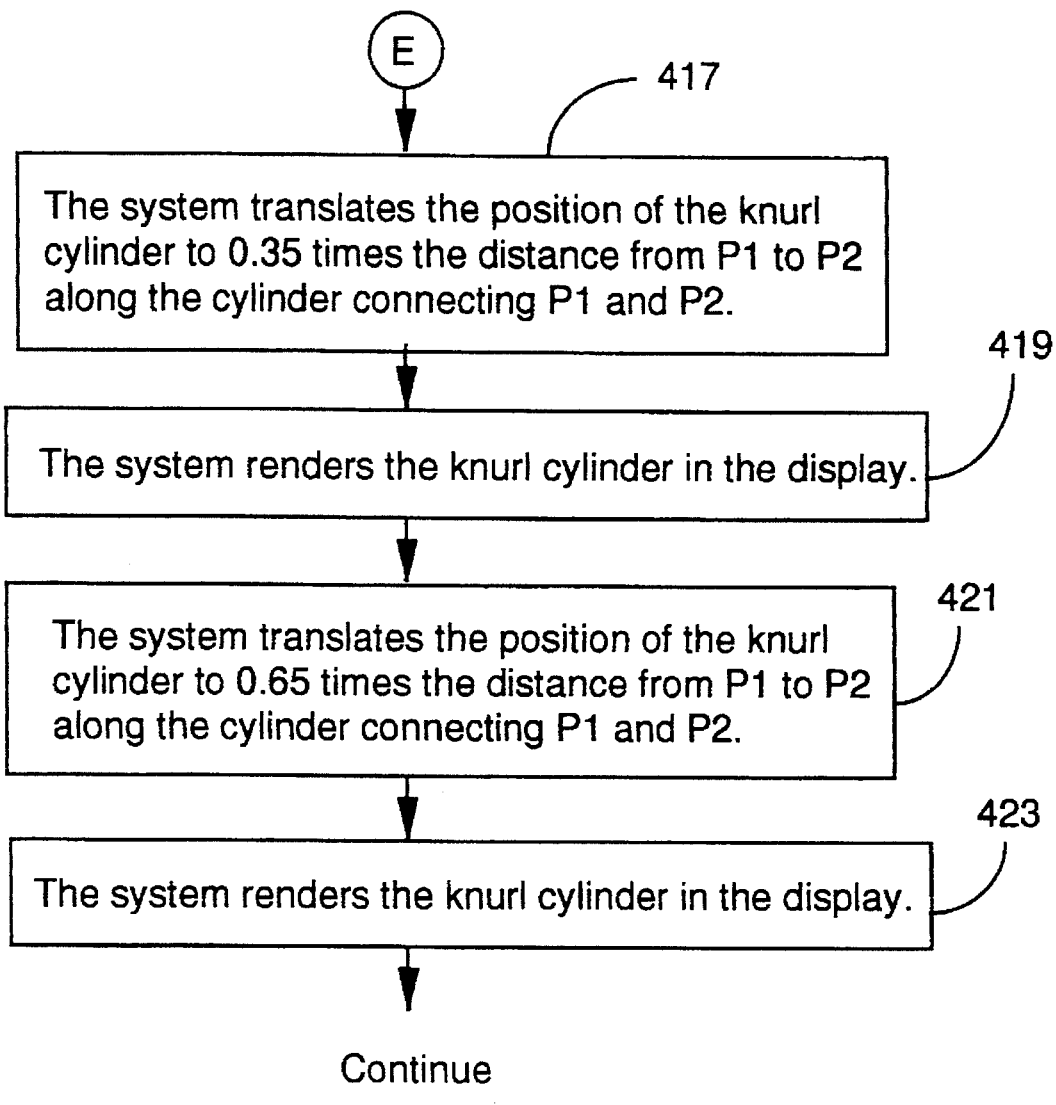

FIG. 29E is a flow diagram enlarging on FIG. 29A.
FIG. 29E is a flow diagram enlarging on FIG. 29A.
FIG. 29F is a flow diagram enlarging on FIG. 29A.

DESCRIPTION OF THE PREFERRED EMBODIMENTS

General Description

Figure 1A:
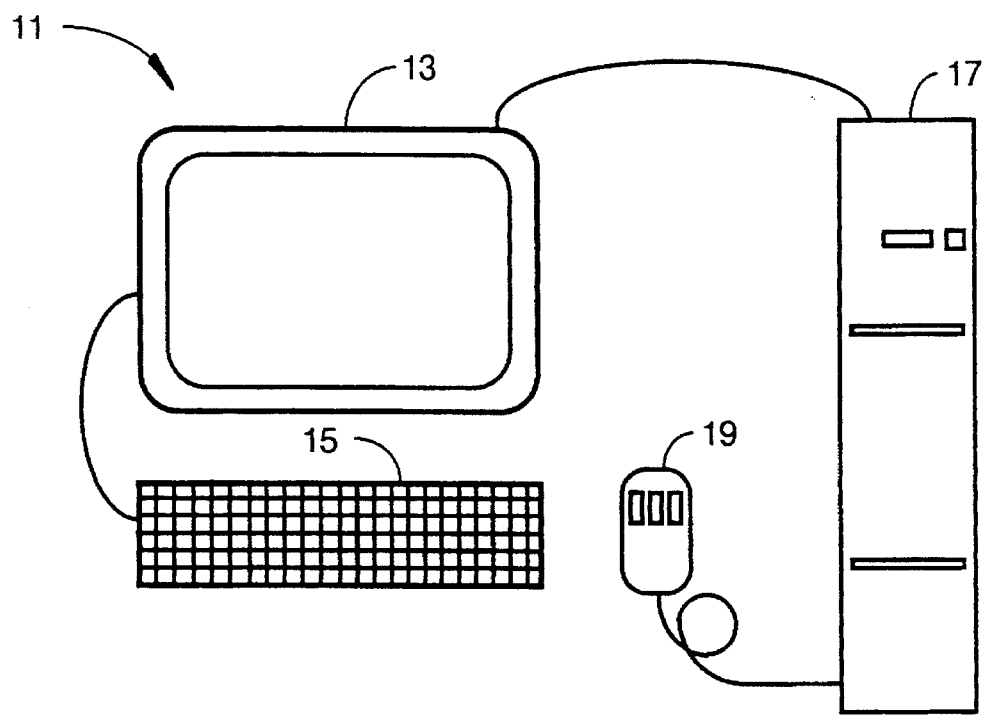
FIG. 1A is a diagram of a computer graphics system as used in the present invention.

FIG. 1A is a pictorial diagram of a computer graphics system 11 as used in an embodiment of the present invention, comprising a computer mainframe 17; which itself comprises disk storage devices, a CPU section, random access solid-state memory (RAM), read-only memory (ROM), and communication buses; a monitor 13, typically a CRT-based unit; a keyboard input unit 15, and a "mouse" input device 19. System 11 of the present invention comprises extensive control routines, usable in conjunction with the workstation, but not shown in FIG. 1A. In the preferred embodiment the workstation is a Silicon Graphics workstation, and the operating system is a version of UNIX. In other embodiments alternative hardware platforms may be used, including minicomputers, supercomputers, and systems based on local area networks (LANs) wherein control routines and data organization may be localized and operator interfaces are provided at a plurality of workstations connected to the LAN. Many other input devices other than the mouse device mentioned may also be used in alternative embodiments, such as spaceballs, trackballs, power gloves, and the like. Additionally the system may be implemented in operating systems other than UNIX.

Figure 1B:
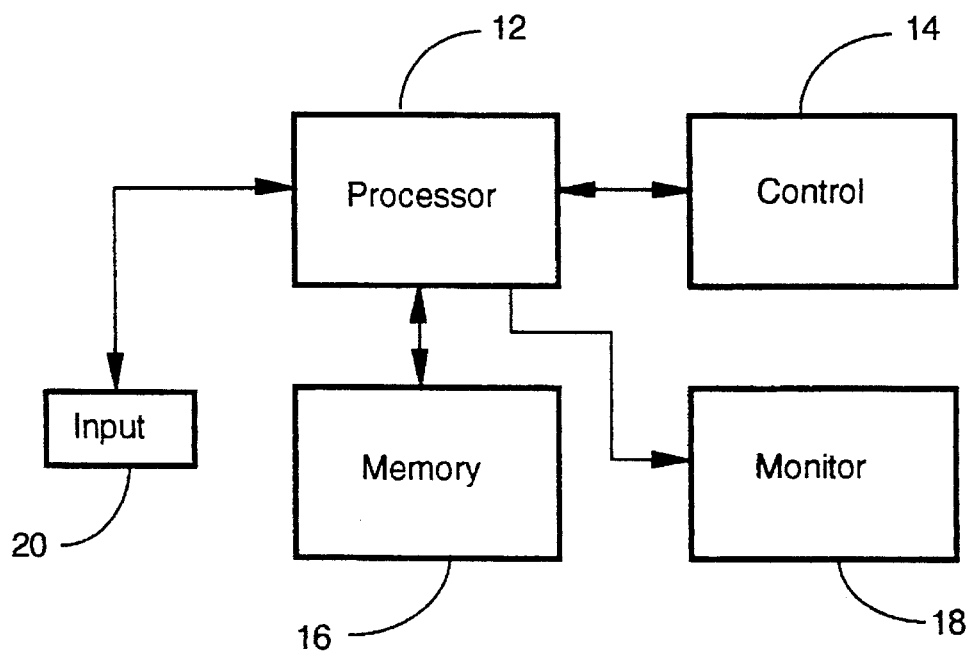
FIG. 1B is a block diagram of components of a computer graphics system according to the present invention.

FIG. 1B is a functional block diagram of elements of the computer graphics system of FIG. 1A. Processor 12 is the central processing unit for the system, and typically includes a microprocessor. Input block 20 is coupled to the processor and includes all of the input devices used with the system, including the mouse device and the keyboard. Lines and arrows between the system elements indicate communication between elements. Communication between input block 20 and the processor is shown as two-way, even though the units that comprise block 20 are known as "input" units, because in some embodiments of the present invention some characteristics of input devices, such as a mouse, are controlled in response to specific data.

Memory block 16 comprises storage devices for storage of relative to system operations. Monitor 18 coupled to the processor provides display of models and information relative to editing and selecting. Control block 14 provides the control direction for the system for all activities, which includes selecting "building blocks" for molecular models, selection of editing tools for altering the models, and more, described in detail below.

Figure 2:
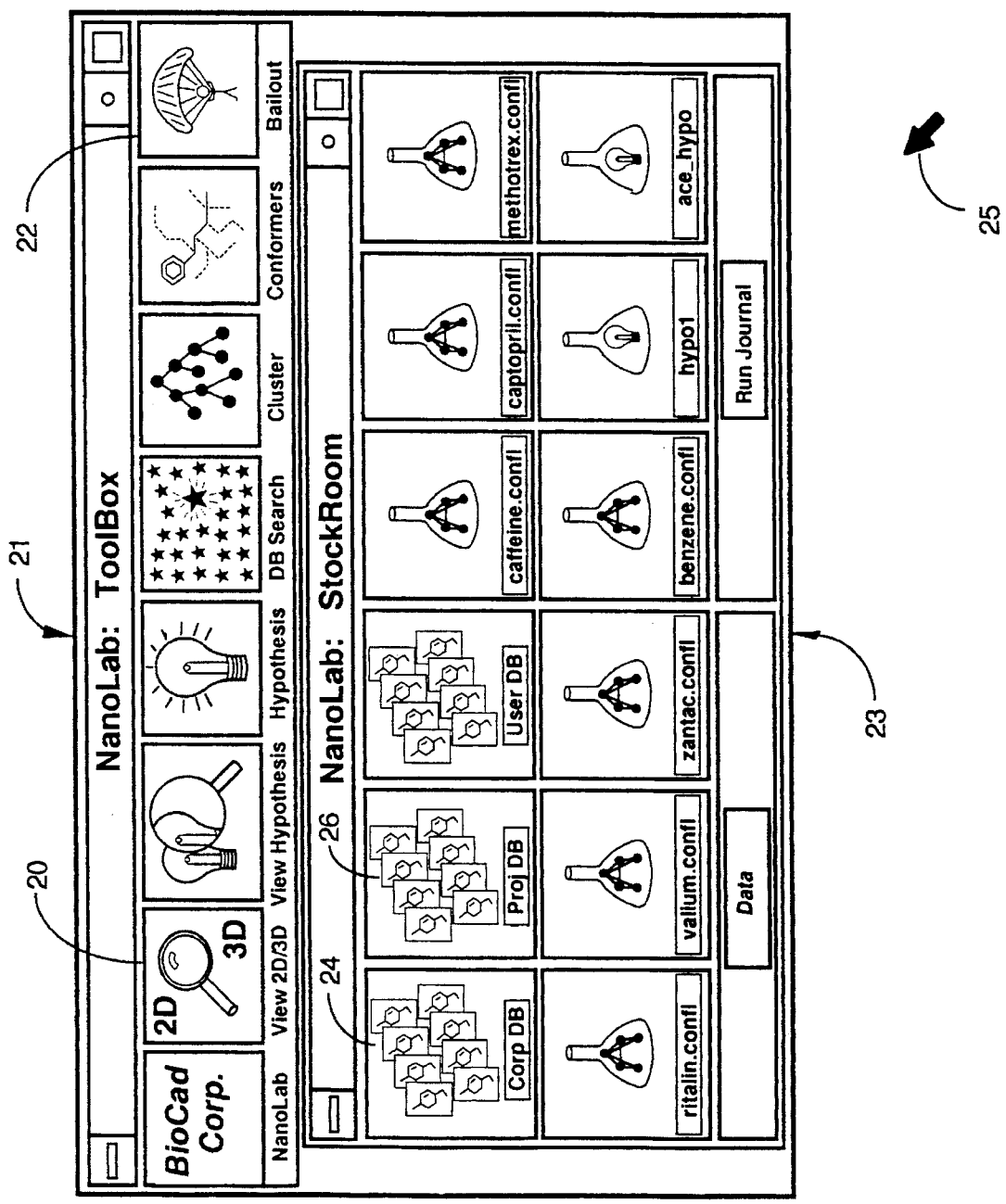
FIG. 2 is an annotated screen print of a display from the system showing a toolbox and a stockroom for selecting entities for use and display.

In the present invention a user-friendly operator interface is presented on the CRT screen of monitor 13, based on a "windows" format familiar to persons with everyday computer experience. An investigator operates the system by selecting options and initiating actions using input devices such as mouse 19 in conjunction with a cursor displayed on the screen. When an investigator first starts up the system, typically two windows are presented. FIG. 2 shows these two windows, Toolbox 21 and Stockroom 23. The system presents cursor 25 on the display as well, and the cursor is movable over the area of the screen in response to movements of mouse 19, as is known in the art. There are a number of equivalent methods of associating input devices with such a cursor, such as with joysticks or trackballs, among others.

Toolbox 21 is an iconic menu of tools presented for user selection. Several function icons are shown in FIG. 2, such as View 2D/3D icon 20, and Bailout icon 22. These icons represent tools available to a user, and tools can be added to or removed from the system.

Stockroom 23 presents an hierarchical organization for an investigator to select stored entities for further investigation or for use with other projects or procedures. A stored entity may be a compound that can be displayed and further edited and manipulated, a text file, a vector or bitmap drawing, or any of a number of other types. In FIG. 2 there are several bases shown, such as CorpDB 24 (for Corporate data base) and ProjDB 26 (for project data base). An investigator may construct other data bases with different names.

The system of the invention allows an investigator an ability to construct chemical models from more primitive elements, in a building block fashion, and to display, edit, and manipulate the resulting models in both two dimensions and three dimensions simultaneously.

Through specialized functions provided, an investigator using the system of the present invention can query energetics and molecular forces as a result of manipulations, providing critical insight into properties of modeled species. An important functionality provided by the system of the present invention for such investigation is the View 2D/3D function available from Toolbox 21.

2D/3D Simultaneous Display

Figure 3:
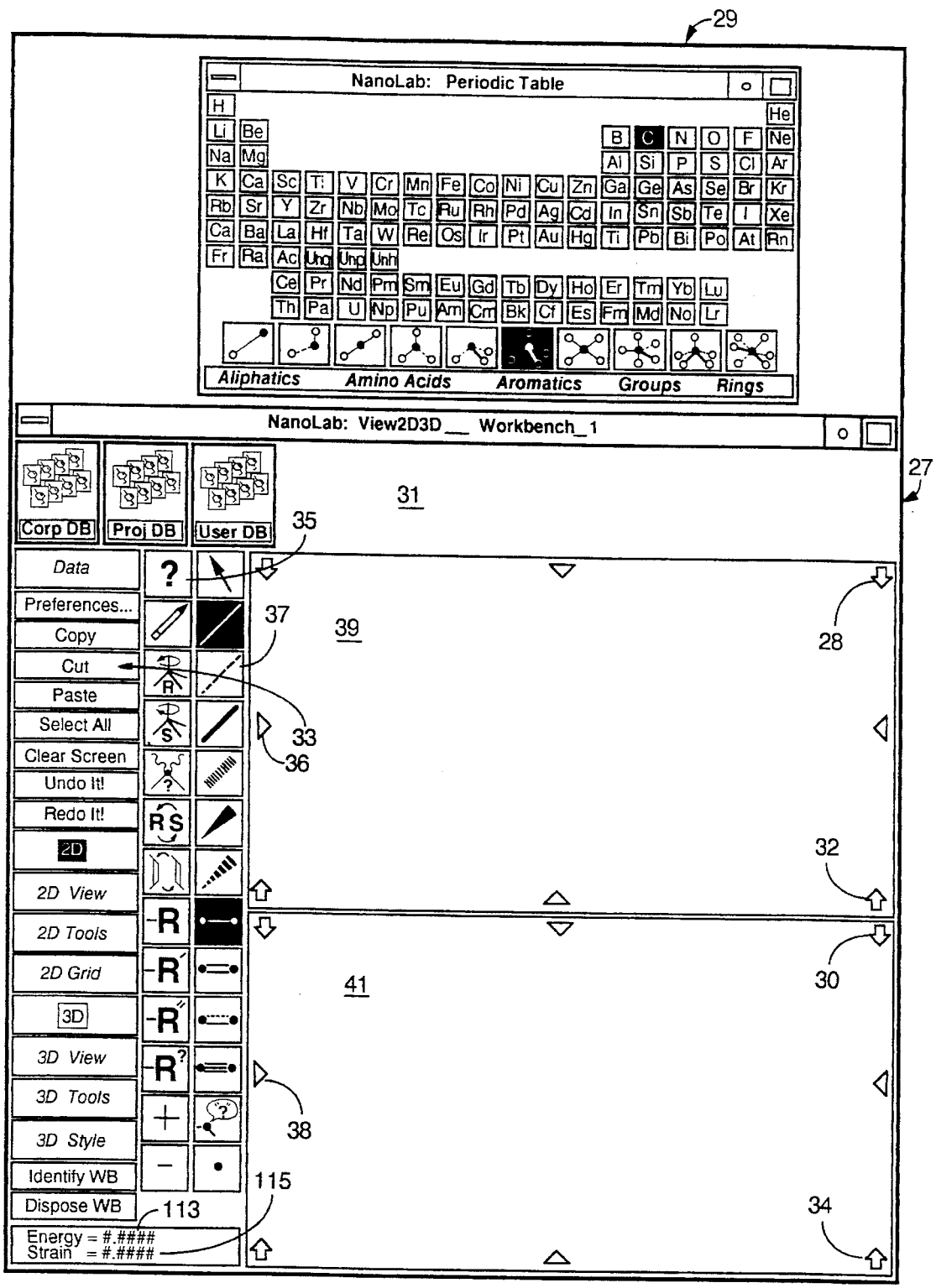
FIG. 3 is an annotated screen print of a display from the system showing the periodic table and a 2D/3D workbench.

To select 2D/3D an investigator moves cursor 25 by means of moving mouse 19 to place the cursor over 2D/3D icon 20 in the toolbox, and momentarily depresses a button assigned to the purpose on the mouse device. This is a familiar technique in the art, known as "clicking". The same procedure is used to select any other of the ToolBox functions and is also used to select objects in a display. When the 2D/3D function is selected thus, the system displays 2D/3D window 27 shown in FIG. 3. The 2D/3D window, along with other functions selectable from the toolbox, is called a workbench. Also shown in FIG. 3 is a periodic table 29, which, together with pull-down menus, serves as a palette for an investigator to select atoms and preassembled molecular moieties for adding to a structure in the display windows, and to select among various geometric coordinations in which a new entity may be added to an existing structure. In the preferred embodiment the periodic table opens when an investigator opens the 2D/3D workbench.

Area 31 across the top of the 2D/3D workbench is called a shelf, and objects may be moved from the stockroom to a workbench shelf, analogous to a work area that an investigator might use in "wet" chemistry. To move an object to the shelf of the 2D/3D workbench, an investigator can "drag and drop" an item from the stockroom to the shelf. A copy of the object is transferred to the shelf. "Drag and Drop" is a procedure familiar to computer operators. An object on the shelf is more readily accessible to the functions of the workbench, so less time is required for accessing the same items in the stockroom.

There are two separate display areas in the 2D/3D workbench. Display area 39 is for two-dimensional display of chemical structures, and display area 41 is for three-dimensional display of the same chemical structures. Each display may be used for editing structures, and there are certain advantages to the use of each display. For example, structures are represented in the two-dimensional display in the fashion that is most familiar to bench chemists and that appears in most chemistry texts and chemical literature in general. Chemical topology (connectivity) is thus easily recognizable. In the three-dimensional display, the same structures displayed and managed in two dimensions are shown in three dimensions, providing structural information not available in the two-dimensional representation. An investigator can choose to work in either format, depending on which format offers maximum advantage at the moment, and the system updates the "other" format in substantially "real" time. Both formats are current at all times, so if a change is made in the two-dimensional window, the same change is immediately reflected in the three-dimensional window. Moreover, the changes made in the two-dimensional and the three-dimensional windows are made from a single set of information. That is, topology for one chemical structure is never separately stored for two-dimensional and three-dimensional display. Topology for a structure is stored at one place, and both displays are updated at all times from the same set of. The advantage of this unique arrangement is that there is never an opportunity for error between the two-dimensional and the three-dimensional renditions. At all times, when one rendition, either two-dimensional or three-dimensional, is altered in any way, the other is updated at the same time.

Figure 12:
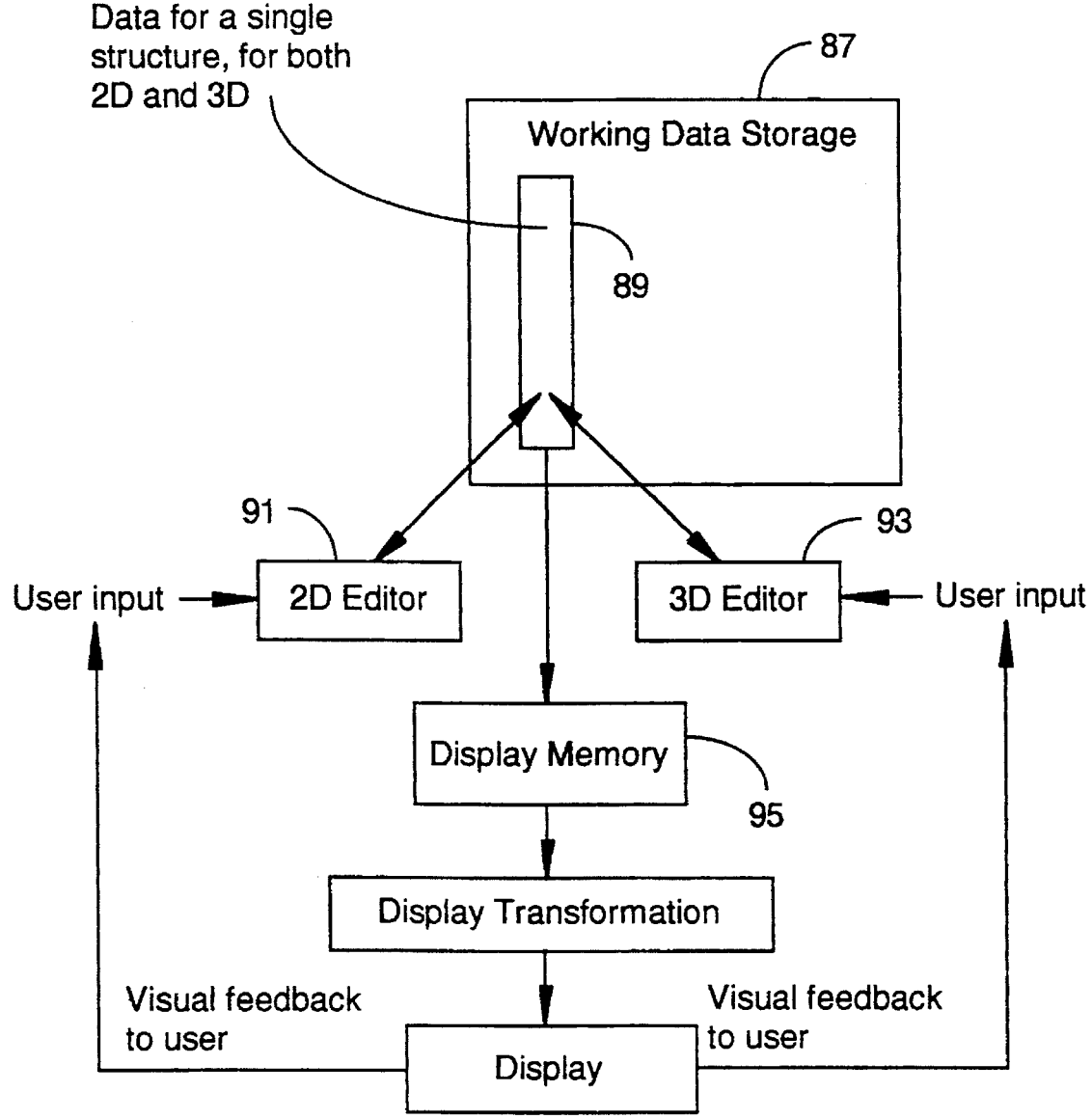
FIG. 12 is a flow diagram showing the data access and flow situation for the two editing portions of the system control.

In the present invention the portion of the control routines devoted to accepting input from an investigator and changing one display or the other is termed an "editor". There are thus two editors, one for the two-dimensional display and one for the three-dimensional display. FIG. 12 shows the access and flow situation for display by the two editors 91 and 93. Storage area 87 may be UserDb of FIG. 2, or a different data base altogether, but for both two-dimensional and three-dimensional renditions is associated with a single storage entity 89. Two-dimensional editor 91 and three-dimensional editor 93 both access information from entity 89 in storage area 87 and alter that as changes are made in either editor by an investigator. Both editors send back to storage, and display memory 95 for the hardware platform being used is updated directly from storage entity 89, keeping the display for both two-dimensional and three-dimensional models up to date in substantially real time.

In the preferred embodiment both two-dimensional and three-dimensional renditions are displayed simultaneously in the 2D/3D workbench window as described above. There may be cases, however, when an investigator wishes to devote his/her entire attention to, for example, the three-dimensional editor alone. In the preferred embodiment this contingency is provided by a feature which allows the user to set the relative size of one window compared to the other. The two-dimensional window can be made to encompass 90% of the screen, for example, and the three-dimensional window then encompasses 10%. One window may also be set to 100%, in which case the user does not see the other window.

In the 2D/3D workbench (FIG. 3), a number of selectable functions appear in a function column 33 down one side of the workbench, and a number of tools are accessible via icons arranged in two columns 35 and 37. "'" is a heading for a pull-down menu that presents selectable functions similar to a File menu in many graphics computer applications, such as Import, Export, and Save. "Preferences" enables input from an investigator to customize certain defaults relating to drawing tools, annotation, and in general all display characteristics. "Copy", "Cut", and "Paste" are drawing functions quite familiar to computer operators. "Select All" selects all individual elements on both editing displays. "Clear Screen" does just that, clearing both editing displays. "Undo it" cancels the previous editing action, and repeated selection of "Undo it" cancels editing actions in reverse chronology. "Redo it" is an Undo for the "Undo it" selection, and cancels "Undo it" commands in reverse chronology. "2D" in the function list explicitly sets the two-dimensional window as the input focus. The two-dimensional window is also enabled simply by clicking the mouse button in the area bounded by the two-dimensional display. This is true as well for the selection "3D".

Selecting "2D View" produces a pull-down menu with selections for defaults in the way two-dimensional representations are made. "2D Tools" provides a pull-down menu with tool selections for "cleaning up" the two-dimensional picture. "2D Grid" provides an ability to display a background grid overlying the two-dimensional display area as an aid in drawing. Selecting "3D View" produces a pull-down menu with selections for the way the three-dimensional display is presented. "3D Tools" produces a pull-down menu of tools for use with three-dimensional editing. "3D style" provides selections for alternative modes of three-dimensional display, such as Wireframe, Mesh, Dots, Tube, Ball-and-Tube, and Space Filling. The several display protocols are named by the way that they display a model, and each protocol has certain advantages under certain conditions. Wireframe, for example, provides a display as though the model were made of wire, with joints at atomic centers and straight sections of wire between representing bonds. Wireframe representation is a well-known format in computer graphic display of molecules, and in other three-dimensional applications. Dots, for another example, provides an indication of the Van der Waals radii of atoms in a molecular structure as "clouds" surrounding the atomic centers, the extent of the clouds indicating the relative extent of field effects. Space-Filling shows a molecular structure with atoms represented as Van der Waals spheres, providing a graphic display of molecular shape, which is of particular use in studies for which steric interactions are key, such as docking studies.

Columns 35 and 37 provide icons for selecting more tools essential to building, editing, and displaying chemical structures. The question mark invokes a context-sensitive "help" facility providing an investigator with on-screen explanations of functions and procedures. In general, the iconic selections operate by "attaching" a functionality to the cursor, a commonly used technique in computer applications. There are several tools selectable for altering the chirality of structures in the displays, for indicating the nature of a bond as single, double, triple, and so forth. One can also change the charge on an atom or structure by using the + and − icons. In the two-dimensional rendition there are conventional wedge symbols for indicating the direction, into or out of the screen, for bonds that do not lie in the plane of the two-dimensional display.

Panning and Zooming

In both the two-dimensional and the three-dimensional display areas there are facilities for panning and for zooming (magnifying and shrinking) the displayed structures. Arrows in the corners of each display area, such as arrows 28 and 30, are Zoom arrows. If one selects an upper arrow, pointing downward, and moves the cursor into the display area (down) while holding the mouse button depressed (dragging), the image is "zoomed out"; that is, the image becomes smaller, as if seen from a further distance. One can return to the original apparent size or anything in between by dragging the cursor "up" without releasing the button. Similarly, the lower corner arrows, such as arrows 32 and 34 pointing "up", are for zooming in on an image, the image becoming magnified in scope relative to the amount of upward vertical movement. With either zoom-in or zoom-out, the user can release the button, reposition the cursor, and then continue zooming in the same direction.

The arrowhead symbols in the centers of the sides of the bounding box for either the two-dimensional or the three-dimensional display area, such as arrows 36 and 38, are for panning the displayed image. The direction of the arrows indicates the direction the display moves relative to the user's viewpoint when one selects an arrow and drags, in the same way that one selects and drags for zooming.

Three Dimensional Rotation and Translation

An important feature of the 2D/3D display is an ability to rotate and translate structures so features may be seen from a variety of views. In the three-dimensional editor an investigator may rotate a three-dimensional structure on any axis and to any degree, and translate the molecule in three dimensions. This complements the above-mentioned ability to pan and zoom to be able to see the structure from a wide variety of vantage points.

Figure 9A:
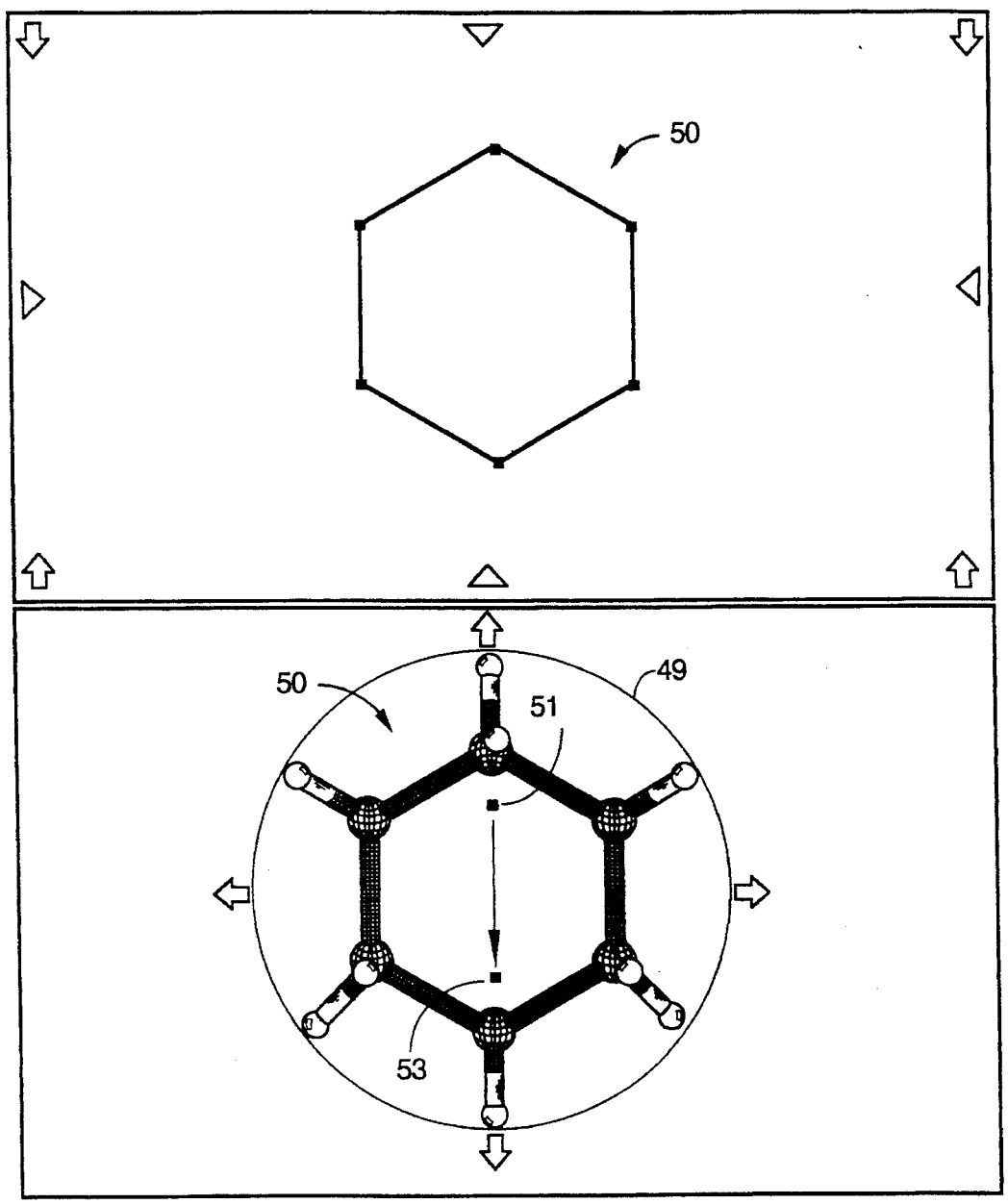
FIG. 9A is an annotated screen print of a display showing a rotation and translation sphere, which is a manipulation element for moving a model in the three-dimensional display.

Panning and zooming in the two-dimensional and three-dimensional displays have already been described above. In the three-dimensional window rotation and translation is enabled by depressing the control key on the keyboard. Other appropriate signals could easily be utilized instead. When rotation is enabled, a spherical boundary representation 49 appears on the three-dimensional display as shown in FIG. 9A. Boundary 49 represents a transparent ball with molecular structure 50 captured and held, such that if the ball is rotated, the structure is rotated as well. Rotation is accomplished by "grabbing" the ball and dragging the cursor in the direction one wishes to rotate the ball. This is a technique known in the art and described in the 1988 SIGGRAPH Conference Proceedings published in the journal Computer Graphics, vol. 22, No. 4. The relevant article is by Michael Chen, S. Joy Mountford, and Abegail Sellen, is on pages 121–129 and is titled: "A Study in Interactive 3-D Rotation using 2-D Control Devices".

Figure 9B:
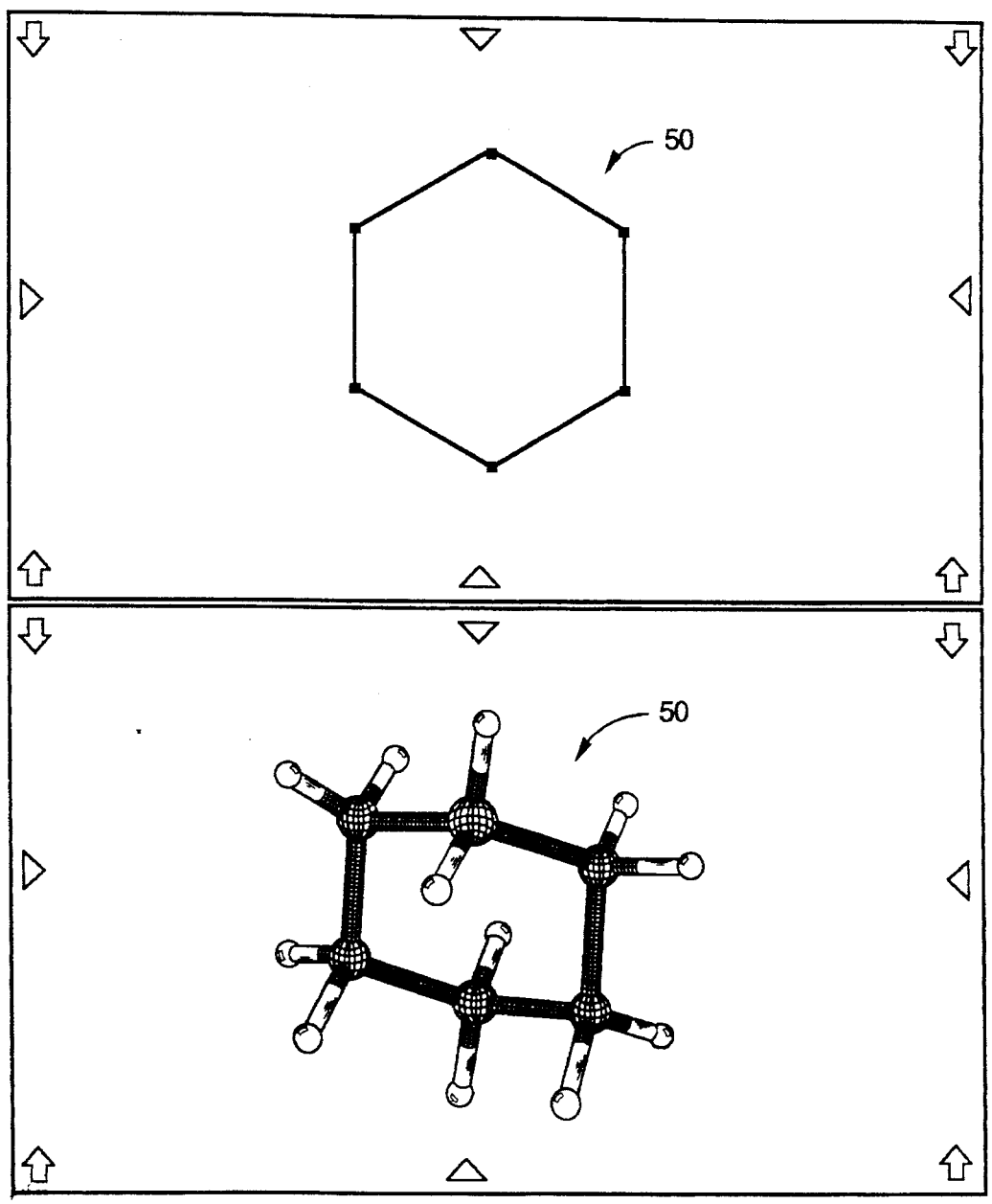
FIG. 9B is an annotated screen print of a display showing the same molecule shown in FIG. 9A, but rotated.

In FIG. 9A a cyclohexane ring structure 50 is shown in the virtual ball. If one wants to rotate the structure about a horizontal axis with rotation toward the user above the axis, one places the cursor over the structure (by moving the mouse) as though contacting the virtual ball, depresses the mouse button to "grab" the ball, and drags in a downward direction, as one would do with an input ball. The image rotates as though the ball were being rotated by the dragging action of the mouse. FIG. 9A illustrates placing the cursor at a point 51 on the virtual ball, and dragging to a new point 53 directly downward. The system rotates the image toward the user, and calculates the angular displacement by the apparent diameter of the virtual ball relative to the length of the drag line. The line length is taken to be a portion of the circumference of the virtual ball. Therefore, if one were to drag from the top of the ball to the bottom, the rotation would be 180 degrees. In the case of FIG. 9A, FIG. 9B shows approximately the newly rotated display, although it is not meant to suggest that the rotation occurs in a stepwise fashion after dragging. Rotation is rather continuously displayed in substantially real time as dragging occurs.

The axis of rotation is incrementally calculated according to the direction the cursor is dragged, and the rotation is displayed in real time, so compound rotations are displayed. That is, it is not necessary to move the cursor in a straight line. One can drag in a curved line, and the system will adjust the axis of rotation throughout the process until the user releases the mouse button.

The Periodic Table

Figure 4:
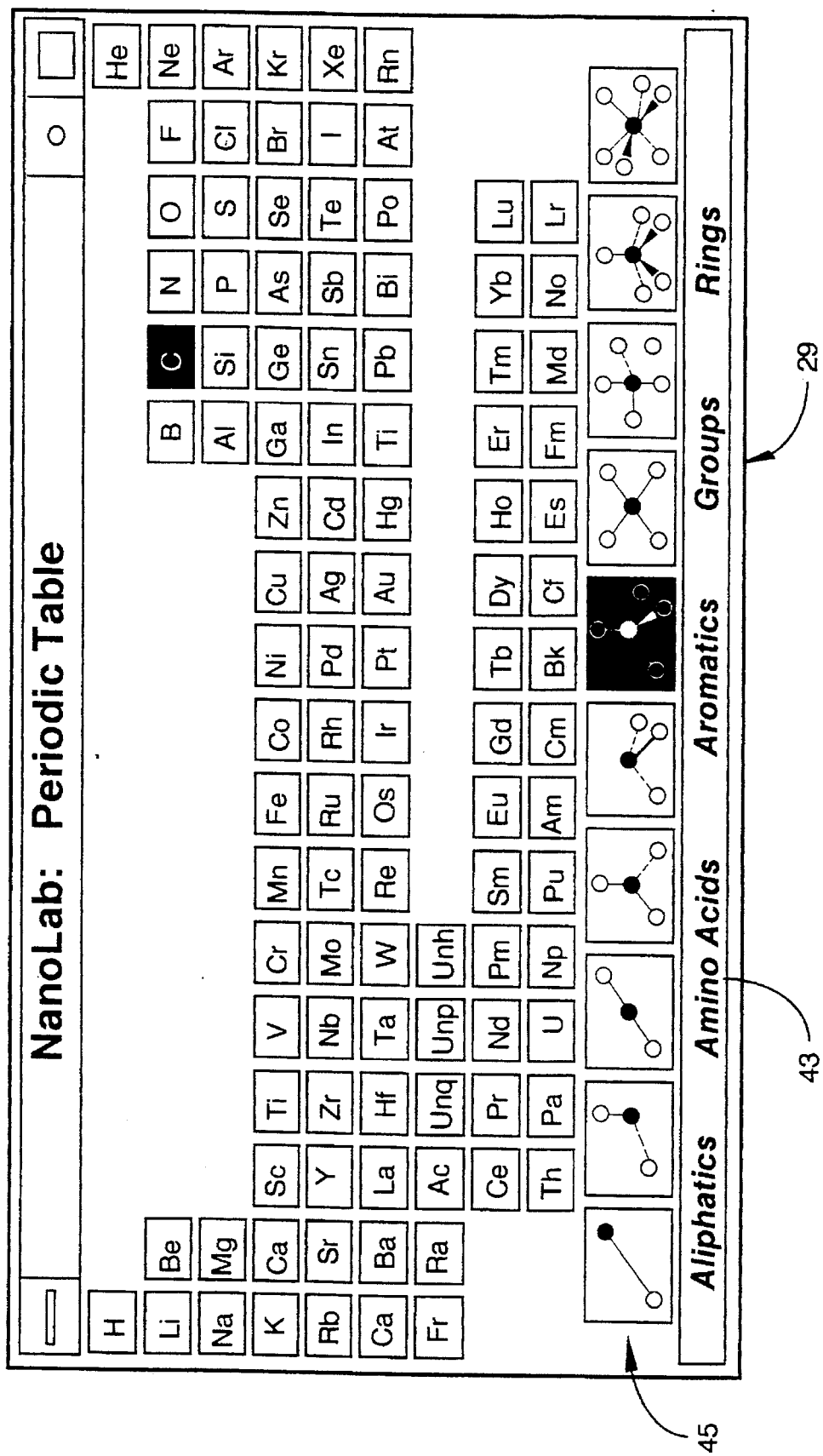
FIG. 4 is an annotated screen print of a display from the system showing the periodic table alone and magnified.

Periodic table 29 provides a palette for selecting primitives for building molecules for investigation. The periodic table, shown in additional detail in FIG. 4, has not only the atomic elements for selection, but a menu bar 43 providing pull-down menus with selections for common chemical groups such as the amino acids, aromatic groups, frequently encountered ring structures, and the like. This menu structure is customizable so that an investigator may develop lists of frequently used structures to suit his/her own needs in investigation.

To incorporate an elemental atom or a predefined structure in a displayed structure for investigation, an investigator need only select the primitive from the periodic table or one of the pull-down menus below the table, move the cursor to either the two-dimensional or the three-dimensional display area, and click the mouse button. If the displays are initially blank, the newly selected structure appears, both in the two-dimensional and the three-dimensional displays. Atoms are displayed in two dimensions in one standard protocol by the atomic symbol and in a pre-selected color. For example, in one protocol chlorine is displayed in the two-dimensional display by the symbol Cl in green, and oxygen by the symbol O in red. Carbon, the most common element encountered in most studies, is displayed in the two-dimensional editor as a dot, and in the three-dimensional editor as a black ball (in the ball-and-tube convention), just as is commonly done by chemists in drawing such structures without computer aids. Also, when a carbon atom is displayed, otherwise unused bonds are shown connected to hydrogen atoms as determined by the coordination geometry, which have white as the default color.

In the three-dimensional display chlorine is displayed in the same color, green, and oxygen red, but the atom symbol will depend on the user's choice of display protocol. For example, if the ball-and-tube convention is active (selected under the 3D Style menu), an oxygen will be a red ball and a chlorine atom a green ball, and bonds will be represented by tubes between atoms.

A coordination geometry selection group is displayed in a row 45 just below the elements of the periodic table and above the group menu bar. This selection is to set the coordination geometry for selected atomic elements. The table is a "smart" table. When a user selects an element, the system will automatically select the most reasonable coordination geometry consistent with valence and geometry, and that selection will be highlighted when an element is selected. If a user makes no alternate selection, the default scheme is used by the system to display the selected element and to add the element to an existing chemical structure displayed. The table allows unreasonable bonding schemes, however, and a user need only click on an alternative icon in the connective geometry selection table after selecting an element and before placing the element in the display to use a different scheme.

Figure 5:
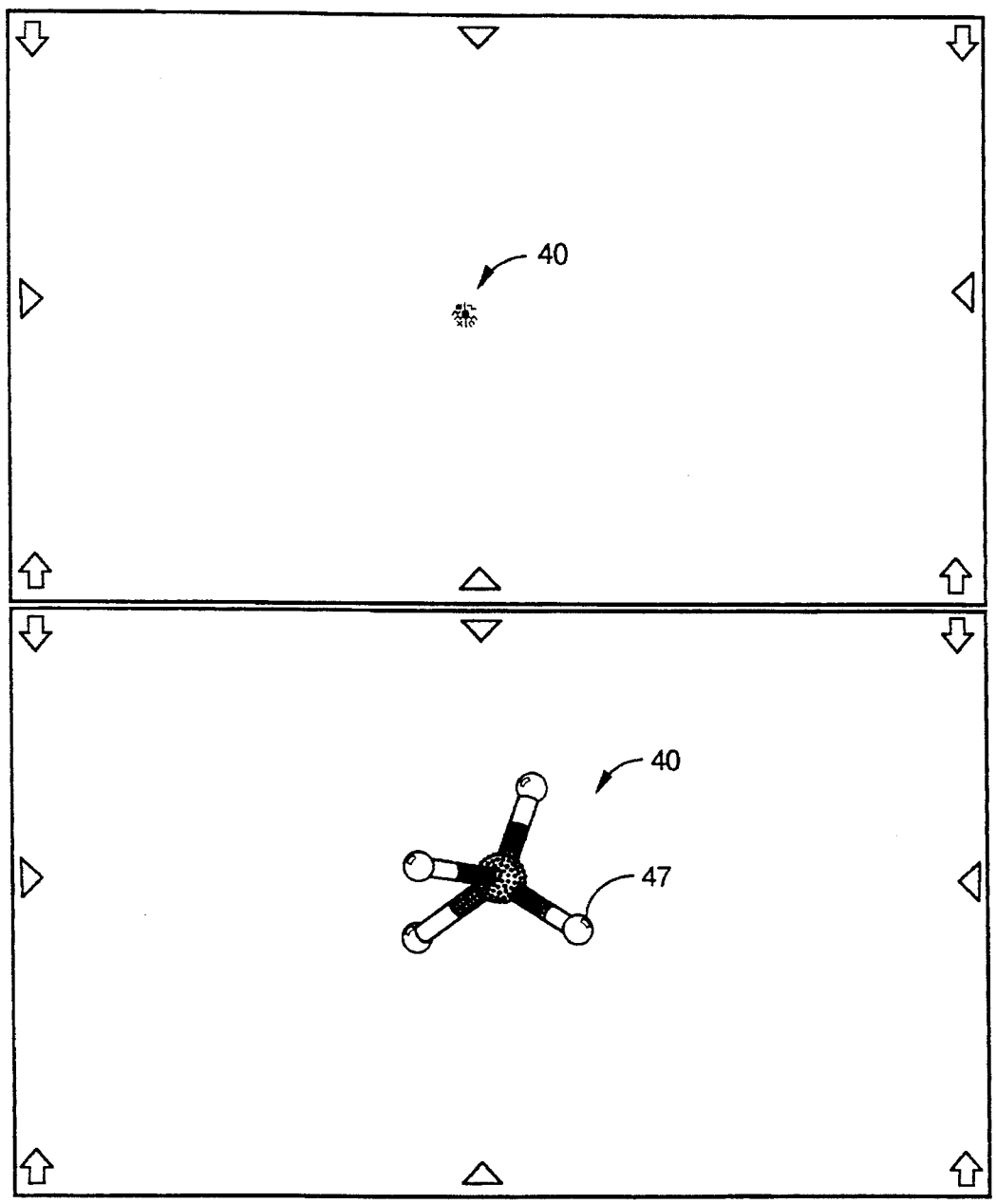
FIG. 5 is an annotated screen print of a display from the system showing a two-dimensional and a three-dimensional display of a single carbon atom.

If there is an existing structure in the two-dimensional and three-dimensional displays, it is necessary for the investigator to indicate, after selecting a primitive, where on the available bonding sites of the existing structure the new structure is to be appended. As an example, FIG. 5 shows a single carbon atom 40 in both the two-dimensional and three-dimensional displays. The display in two dimensions is a simple dot, while in three dimensions, the valence is shown as satisfied by 4 bonds to hydrogen atoms with the known bond angles. This completion of the chemical structure in the simplest stable manner is an automatic function of the system.

Figure 6:
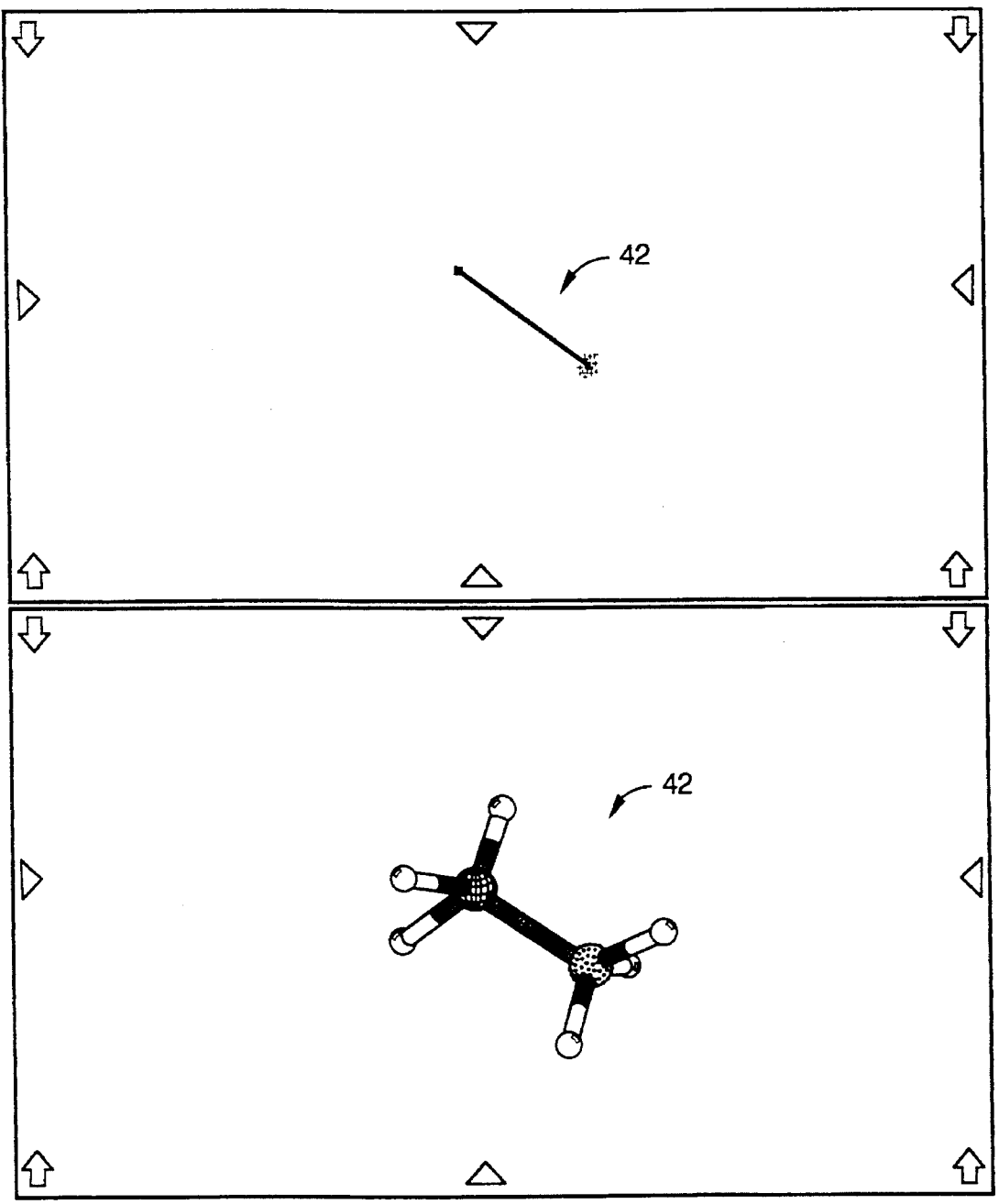
FIG. 6 is an annotated screen print of a display showing two carbon atoms joined to make $C_2H_6$.

If an investigator selects carbon from the periodic table and clicks on hydrogen atom 47 in the three-dimensional display in FIG. 5, the system removes the hydrogen atom and appends the new carbon to the selected point of the existing carbon as shown in FIG. 6, with the valence of the new structure satisfied again by hydrogen atoms. The new structure 42 is $C_2H_6$ in a stable conformation. New atoms and groups may be added after this fashion to create both simple and sophisticated molecules.

Not only may new primitives (atoms or substituent groups) be added, but a user can also connect "bondable" points in an existing structure. For example, after selecting six carbon atoms and connecting them in serial fashion, an investigator can select one of the carbon atoms at one end of the molecule, drag to a carbon atom at the other end of the molecule, and thereby connect the two carbon atoms, forming a ring structure. Another way the user may initiate bonds is to hold down the shift key, click on a bond (holding the mouse button down), drag to another bond, and release the mouse button (called "mouse up"). This procedure is called "bond fusion". Alternatively, the user may employ the same sequence, selecting atoms instead of bonds. Additionally, the user may select two atoms (by clicking with the mouse), and then select the Bond tool from the 3D Tools pull-down menu. In any case described, if a bond is allowable, the system will alter the displays to show the new bond in place.

The bonding editing procedure is available in either the three-dimensional display or the two-dimensional display, and, as with all other edits, a change made in one display is immediately shown in the other.

There is also facility for correcting an error or making a new choice. One can, for example, use the erasure tool to delete atoms and groups from an existing structure and add new atoms or groups in place of those removed.

As mentioned above, there is a data base common to both the two-dimensional and the three dimensional editors that represents a molecule's topology only once and associates it with both a two-dimensional geometry and a three-dimensional geometry. The common data base assures the consistency of the two representations by constructing both representations from the common topology. The data base makes the update of the "other" representation much faster than conventional and alternative methods, because it eliminates any need for translation or transposition of the common.

Two-dimensional Display Routines

The system generates two-dimensional geometry by one of three methods, depending on circumstances. The three methods and the conditions for each method are illustrated by flow diagram FIG. 7.

In each of the three methods, stereochemical choices in the three-dimensional representation are faithfully reproduced in the two-dimensional drawing with wedges, hashes, and Cahn-Ingold-Prelog R and S notations. These notations are common practice in the art of chemical representation in two-dimensional format.

Figure 7:
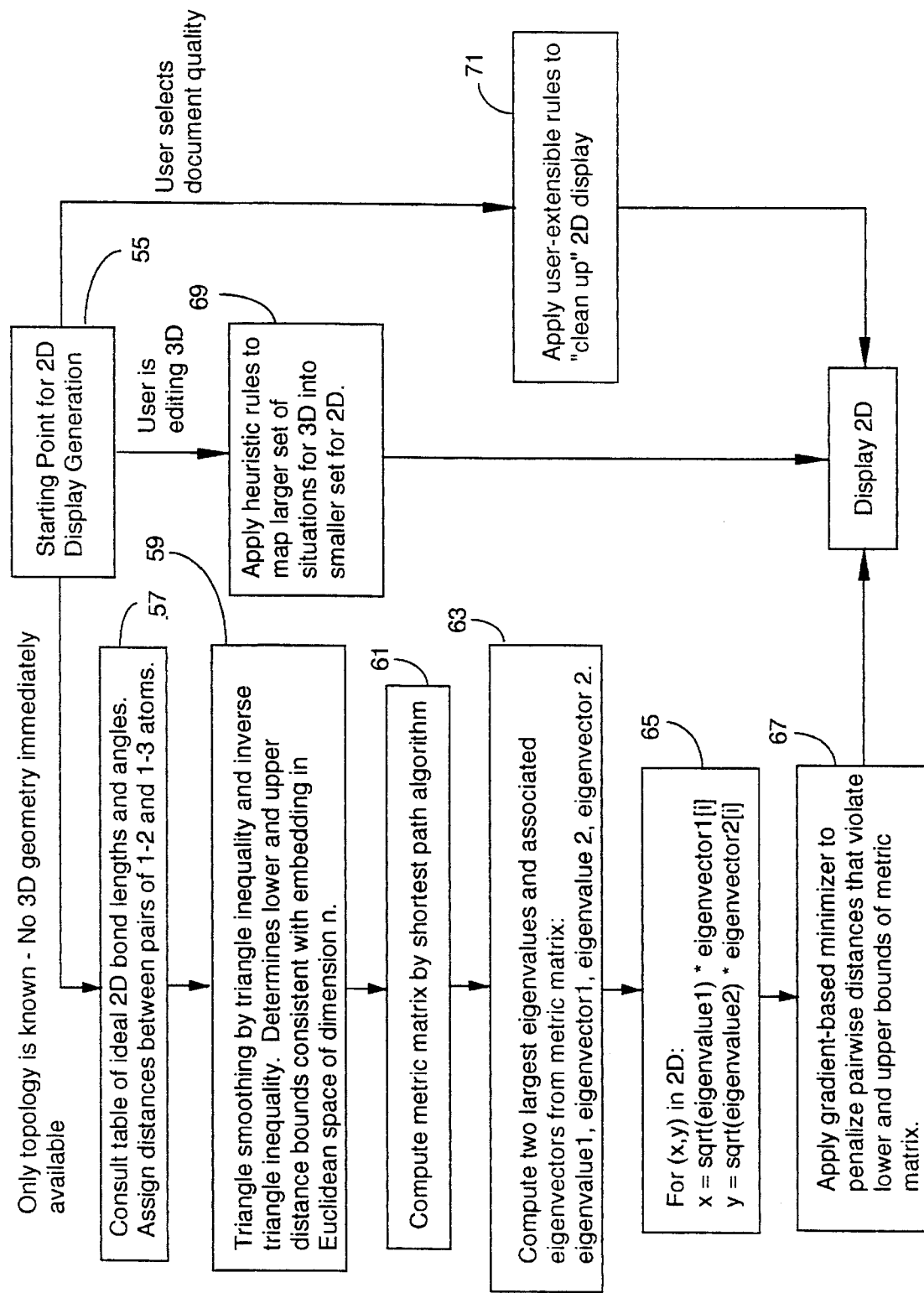
FIG. 7 is a flow diagram showing three methods by which the system generates two-dimensional display under different conditions.

The system makes a display decision among the three methods each time a change is made, such as by adding a new element, causing a rotation or translation, and so forth. This decision point is represented in FIG. 7 by block 55. If there is only topology to work from, and there is no three-dimensional geometry to copy, as when a molecule is first displayed, the system uses 2D-Distance geometry to generate the two-dimensional conformer. This method can also be used by the system to generate a two-dimensional display when an investigator changes topology in a "global" fashion, such as connecting the endpoints of an N-alkane to make a ring structure.

In two-dimensional distance geometry the system first uses a stored look-up table of ideal two-dimensional bond lengths and bond angles to assign distances between pairs of 1–2 and 1–3 atoms (block 57). By using the triangle inequality and inverse triangle inequality, the system accomplishes "triangle smoothing" to determine a lower and upper distance bound between every pair of atoms in a molecule to be displayed that would be consistent with an embedding in a Euclidean space of dimension n, where n is the number of atoms in the molecule (block 59). The system next computes the "metric matrix" by assigning to each atom pair in turn a distance between its lower and upper bounds and then propagating the ramifications of that distance to the other distance bounds (block 61). This propagation is accomplished by a shortest-path procedure that uses the triangle inequalities to compute distance.

The system next computes the two largest eigenvalues and their associated eigenvectors from the metric matrix, and assigns them eigenvalue1, eigenvector1, eigenvalue2, and eigenvector2 (block 63). Then (block 65) the x and y coordinates of each atom are computed as:

x[i]=sqrt(eigenvalue1)*eigenvector1[i];

and y[i]=sqrt(eigenvalue2)*eigenvector2[i]

This causes the molecule to have a two-dimensional geometry with minimal RMS error from the pairwise distances in the metric matrix. The system then uses a traditional gradient-based minimizer (block 67) such as conjugate gradient to minimize a function penalizing pairwise distances that violate the lower and upper bounds used in constructing the metric matrix.

A second method is used to update the two-dimensional representation while an investigator is editing the three-dimensional version. The system does this by applying a set of heuristic rules that map the larger set of situations that can occur in the three-dimensional display into the smaller set that can be meaningfully displayed in two dimensions. This method is represented by block 69 in FIG. 7. For example, if 2 atoms are s-cis in three dimensions they are also s-cis in two dimensions.

Following are four other rules stored and followed by the system to render two-dimensional displays while changes are made in the three-dimensional display:

1. The system maintains 120 degree angles between bonds wherever possible (in two dimensions).

2. If more than three bonds proceed from a single atom, the system places any new bond in two-dimensions to bisect one of the bonds related by a 120 degree angle. This will be correct 67 percent of the time, and the user has to manually edit the two-dimensional model when it is not correct.

3. If there is an arbitrary choice to be made regarding bond placement, the system preferably directs the new bond away from the apparent center of mass of the existing structure.

4. If the rule in step 3 above results in an incorrect structure, the user can correct the error by moving to the two-dimensional display and dragging the atom to the desired position.

A third method of two-dimensional representation applies when a user wants a "pretty" or optimally stylized two-dimensional drawing, such as for a hard copy printout for documentation purposes. Because chemists have individual and diverse preferences, the system has a user-extensible rule-based protocol for producing customized two-dimensional drawings. Each rule maps a topological substructure in a topological context to a collection of stylized two-dimensional geometric representations. For example, a cyclohexyl with only chains attached could be drawn as a hexagon, a chair conformer, or an edge-on hexagon with perspective. Another rule maps a phenyl ring either into the letters "Ph", a hexagon with a circle inside (to illustrate conjugation or aromaticity), or a hexagon with either of the two Kekule structures representing the conjugation of the ring being rendered. The system is able to choose a two-dimensional representation as a result of the three-dimensional geometry in some cases. For example, a cyclohexyl in the boat conformer in three dimensions can be represented by a two-dimensional stylized projection of the boat conformer, whereas a cyclohexyl in the chair conformer in three dimensions can be represented in two dimensions by a stylized projection of a chair conformer. This method is represented by block 71 in FIG. 7.

Three-Dimensional Display Routines

Figure 8:
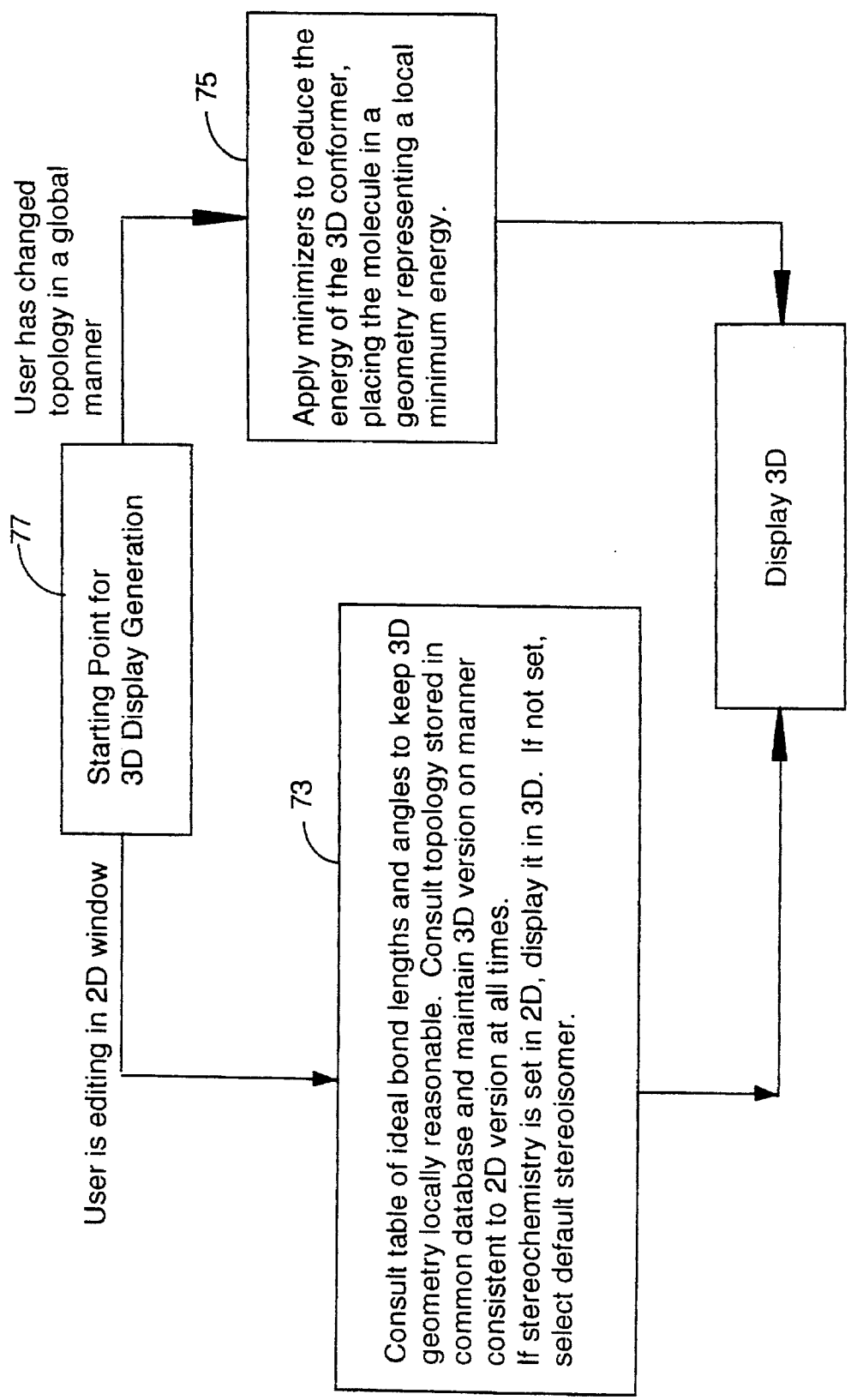
FIG. 8 is a flow diagram showing two methods by which the system generates three-dimensional display under differing conditions.

The system generates three-dimensional geometry by one of two methods, depending on circumstances, as shown in FIG. 8. As in two-dimensional display the decision point (block 77) is reached whenever a change is made.

While an investigator edits in the two-dimensional window, the system maintains the three-dimensional version in a manner that is consistent with the two-dimensional version at all times (block 73). The system has a pre-stored look-up table of ideal bond lengths, bond angles, and dihedral angles, and consults this table to make the geometry locally chemically reasonable while maintaining fidelity to the topology stored in the common data base. The set of heuristic rules that the system follows in updating the two-dimensional version while a user edits the three-dimensional version is also followed in this case. That is, if 2 atoms are connected by a cis double bond in one rendition (eg. two-dimensional), they are also cis in the other (eg. three-dimensional), and so forth. In this manner, both chain construction and ring construction are accurately modeled in both the two-dimensional and the three-dimensional windows. Stereochemistry that has been set in the two-dimensional editor is obeyed in displaying the three-dimensional conformer. If there are stereocenters with unspecified stereochemistry, the system by default assigns one of the possible stereoisomers and qualifies the stereochemical specification as "unknown" (for example, "R?").

There is a case (block 75) where a user has changed topology in a global manner. For example, the user might connect the endpoints of an n-alkane in the two-dimensional editor to form a ring. In this case the system has a method of generating the changed three-dimensional representation from a distant starting point. The method involves using minimizers to reduce the estimated energy of the three-dimensional conformer, such that the molecule is placed in a geometry representing a "local minimum" energy. The system can thus quickly repair a "bad" structure into one that is chemically reasonable.

Three-Dimensional Manipulation

It is well known in chemistry that many molecules can exist in a large variety of geometric conformations. For example, two atoms may be joined by a single bond, and the bond may be rotated, which provides a virtually infinite variety of intramolecular positional relationships. This situation may exist in the case of a molecule consisting of just the two atoms that are joined, as in the case of the $C_2H_6$ shown in FIG. 6. Also, each of the two atoms joined by the single bond may be also joined to other atoms in a more complex molecular structure. Bonds may also be stretched in many cases, changing the geometry of a molecule. Variations of geometry available through bond manipulation is a principal matter of investigation owing to the many possible three-dimensional shapes and concomitant varying chemical properties that result.

In the present invention, there are two distinct situations under which manipulation may be done. One is in the absence of interatomic (Van der Waals forces) and restoring forces, in which case manipulations may be made as though the ball-and-tube three-dimensional model is a simple construction of balls and sticks put together with rotary joints. The other situation for manipulation is with consideration given to the interatomic and restoring forces, which cause more complex geometric distortion (i.e. not local to the perturbation) than simple rotations and displacements. The term used in the preferred embodiment to the situation taking all the forces into account is "physically based modeling" (PBM). In the system of the preferred embodiment PBM can be turned off and on by user-initiated signal. In the present section, three-dimensional manipulation is described with PBM turned off. In a following section titled "Physically Based Modeling", manipulation is described with PBM turned on.

In the preferred embodiment a unique method providing intuitive feedback has been developed and is used during the distortion of geometry of a model in the three-dimensional editor. The method imitates situations familiar in many other activities. When a user selects an object in the editor, the system, referring to the topology in the data base, determines a set of local coordinates that the user may perturb using that object. For example, if the user selects a non-conjugated acyclic bond, the system "knows" that stretching of the bond and dihedral rotation are the only chemically reasonable motions. The system displays visible indications called "knurls" to indicate the available motions to the user.

Figure 10A:
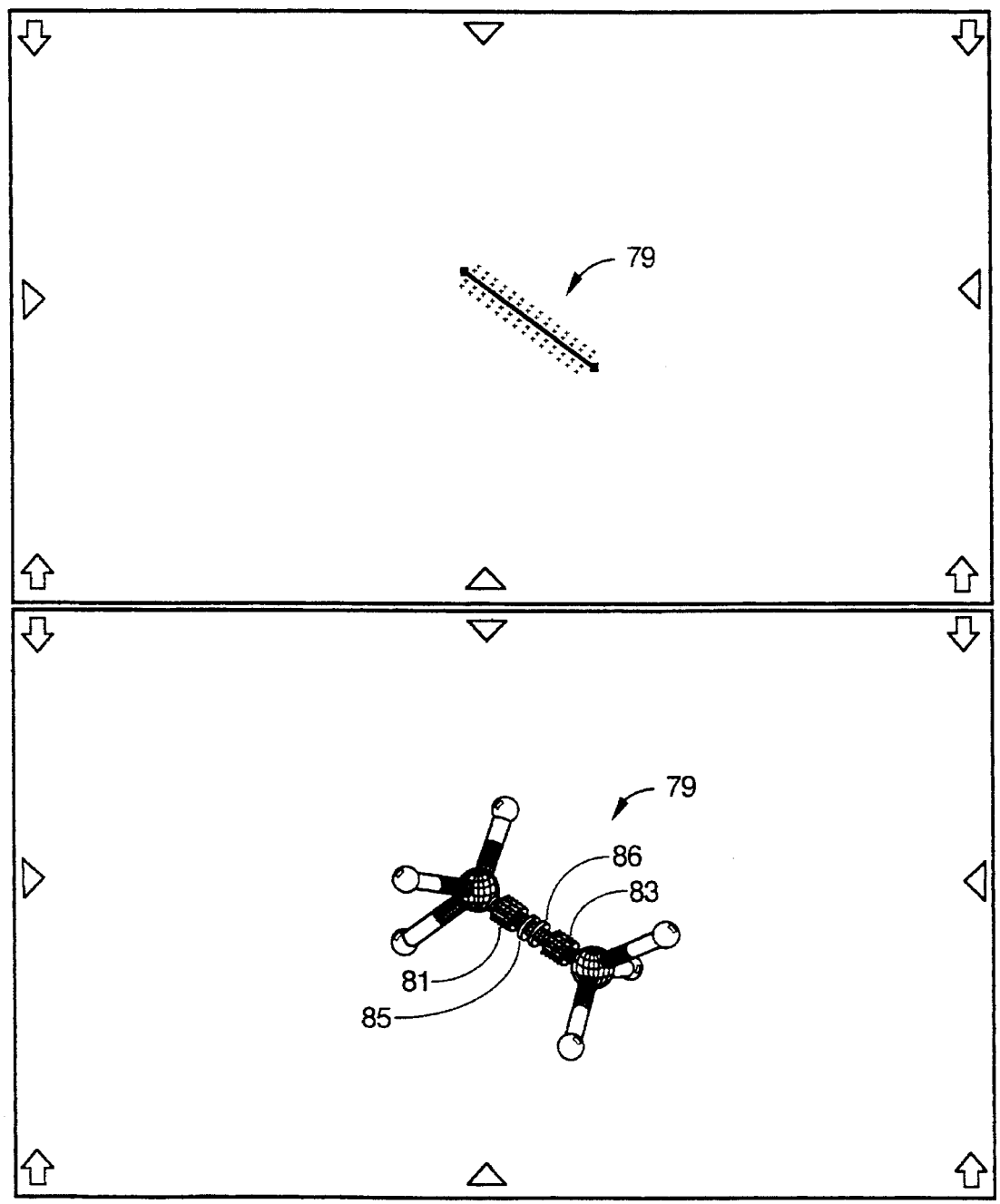
FIG. 10A is an annotated screen print of a display showing manipulation elements called knurls in conjunction with a bond in a model of a molecule.

FIG. 10A shows a bonded pair of carbon atoms forming our by now familiar $C_2H_6$, and bond 79 has been selected by the user for manipulation. The system responds by displaying knurls on the bond. Knurl 81, closer to the carbon-hydrogen complex on the left, indicates the left-side complex may be rotated about the bond, while the right-side complex remains stationary. Similar knurl 83, closer to the complex on the right, indicates the right-side complex may be rotated about the bond while the left side remains stationary. This is as if the user grabs one end or the other.

Figure 10B:
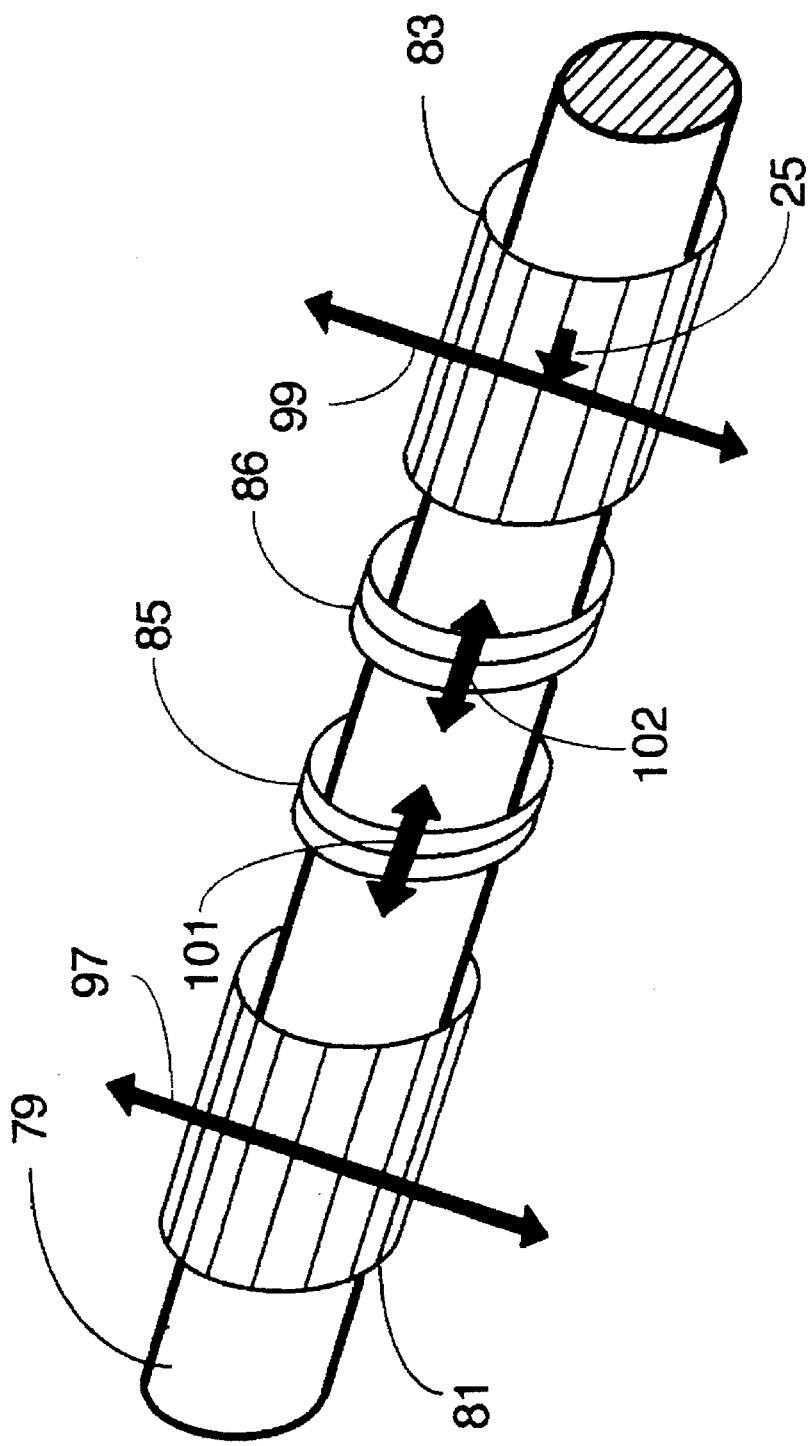
FIG. 10B is a drawing of the bond of the model from FIG. 10A, magnified to illustrate the knurls displayed in conjunction with the bond.

Although it is true that the two rotations just mentioned are equivalent, rather than being two distinct variations in geometry, the two knurls allow the user to control the viewpoint relative to different portions of the molecule, thus the rationale for two rotational knurls. Knurls 85 and 86 between knurls 83 and 81 indicate that the bond may be stretched. Knurls 85 and 86 are not typically displayed when the bond is selected, and require selection of the Stretch function from the 3D Tools pull-down menu. FIG. 10B is a magnified view of bond 79 showing the knurls. Knurls 81 and 83 are displayed on the bond as cylinders around the bond with knurl lines parallel to the bond. This apparent structure is to imitate the same kind of structure common to bottle caps, thumbwheels, and knobs, among other familiar objects people encounter every day, which are meant to be turned by grasping the knurled element. This imitative quality provides a uniquely intuitive signal to the user that the structure can be rotated around this point, and how it may be accomplished.

If the rotative knurl (either position) were, in fact, a cap or thumbwheel, the user would know intuitively to place a thumb or finger on the knurl and apply pressure while pushing or pulling to initiate rotation. This is the action a user takes in the preferred embodiment, in fact, with the cursor used in the display rather than a thumb or finger. The user moves the cursor to the knurl, presses the mouse button in the same action used for grabbing or dragging in the art, and moves the mouse at right angles to the knurl lines, just as one would move to rotate a bottle cap or thumbwheel. The chemical structure on the side closest to the knurl, as well as the knurl itself, rotates in response, just as though the knurl were being turned and the complex were attached to the knurl. In FIG. 10B arrow 97 on knurl 81 and arrow 99 on knurl 83 represent the placement of the cursor and the direction of drag to accomplish rotation by knurl manipulation.

In the preferred embodiment the amount of rotation when manipulating by a rotative knurl is relative to the length of the drag with the mouse. The length of drag is related to the knurl as a circumferential length, so a drag equal in length to the apparent circumference of the knurl causes the rotating complex to rotate a full circle; that is 360 degrees. In other embodiments the relationship can be changed to rotate either more or less relative to drag length.

Figure 11:
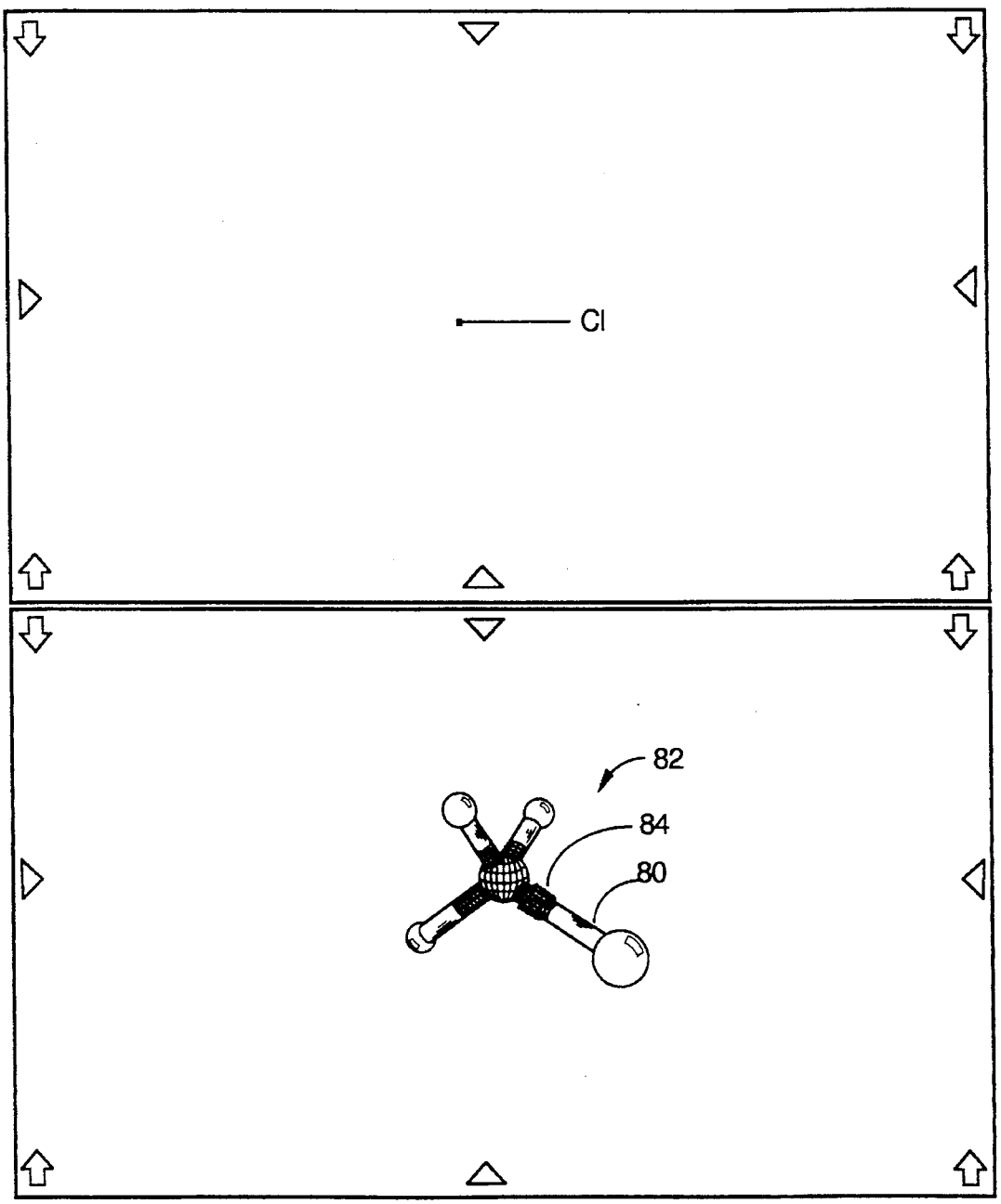
FIG. 11 is an annotated screen print of a display showing an atom with a bond that shows one rotation knurl.

If the structure on one side of a bond is cylindrically symmetric and no rotation would be perceived, then the system does not present a knurl. Further, if the rotation cannot take place without a high energy penalty, such as a double or triple bond, the system presents no knurl. An example of a bond with one rotative knurl is the carbon-to-chlorine bond 80 in the methyl chloride molecule 82 shown in FIG. 11. Rotation of the chlorine atom would not be perceived, so no knurl is located to that side of the bond. The methyl side, however, is structurally more complex, so a knurl 84 is located to the carbon side of the bond. Manipulating knurl 84 will rotate the methyl side of the molecule while the chlorine atom remains stationary.

Knurls 85 and 86 in FIG. 10A and FIG. 10B are for stretching or shortening the bond, and are presented in a graphical representation to approximate sliding collars, with closely spaced circles around the bond cylinder. The two stretch knurls are typically displayed together. To use this knurl to alter bond length, one places the cursor on one of the knurls, presses the mouse button, and drags the cursor along the bond in the direction one wishes to stretch or contract. The two knurls allow the user a choice of which part of the structure to move while stretching or contracting the bond.

The portion of the molecule connected to the bond at the end closer to the knurl will move when the bond is stretched or contracted. The portion to the other side of the bond will remain stationary to the user's view. In the preferred embodiment this action is 1:1; that is, the bond is stretched or shortened by the length of the drag of the cursor in the direction of the bond axis. Cursor movement away from the "stationary" structure will lengthen a bond, and cursor movement toward the stationary structure will shorten the bond. The drag can be "off-line" and the system will calculate the component along the bond axis. In other embodiments other rules may be made to apply. Arrows 101 and 102 in FIG. 10B represents placement of the cursor and drag direction to accomplish stretching or shortening of the bond.

In the preferred embodiment stretch knurls are not typically displayed with bond selection, simply because displaying two rotation knurls and a pair of stretch knurls on a single bond are congested and often too confusing. After one selects a bond, to access the stretch knurl pair, a selection from the 3D Tools pull-down menu is required (See FIG. 2).

With PBM modeling switched off the system computes placement of atomic coordinates as follows: Once an object is selected the system presents the appropriate knurls as described above. When a user selects a knurl and drags, the system computes the displacement of the cursor from the "center" of the knurl. The system projects the x-y-z coordinates of the cursor into the x-y plane and also projects the knurl into the x-y plane. The linear displacement in world coordinates of the projected cursor position from the center of the projected knurl is then used to compute the size of the associated local coordinate transformation by a method depending on what type of local coordinate is mapped to the knurl.

In the case of dihedral rotation, for example, the displacement from the knurl's axis of rotation is mapped by a linear transformation into the angular displacement of the dihedral. Displacement to one side of the axis causes clockwise rotation, and displacement to the other side causes counterclockwise rotation. The system rotates all of the atoms on the appropriate side of the dihedral about the dihedral's axis by the computed angular displacement.

There is another mode of manipulation of displayed structures in three dimensions, which involves moving atoms in a structure in a way that changes the geometry of the structure. This mode of manipulation is available only with PBM, which is described in detail below, but the simple geometry of the manipulation is described here.

Figure 13A:
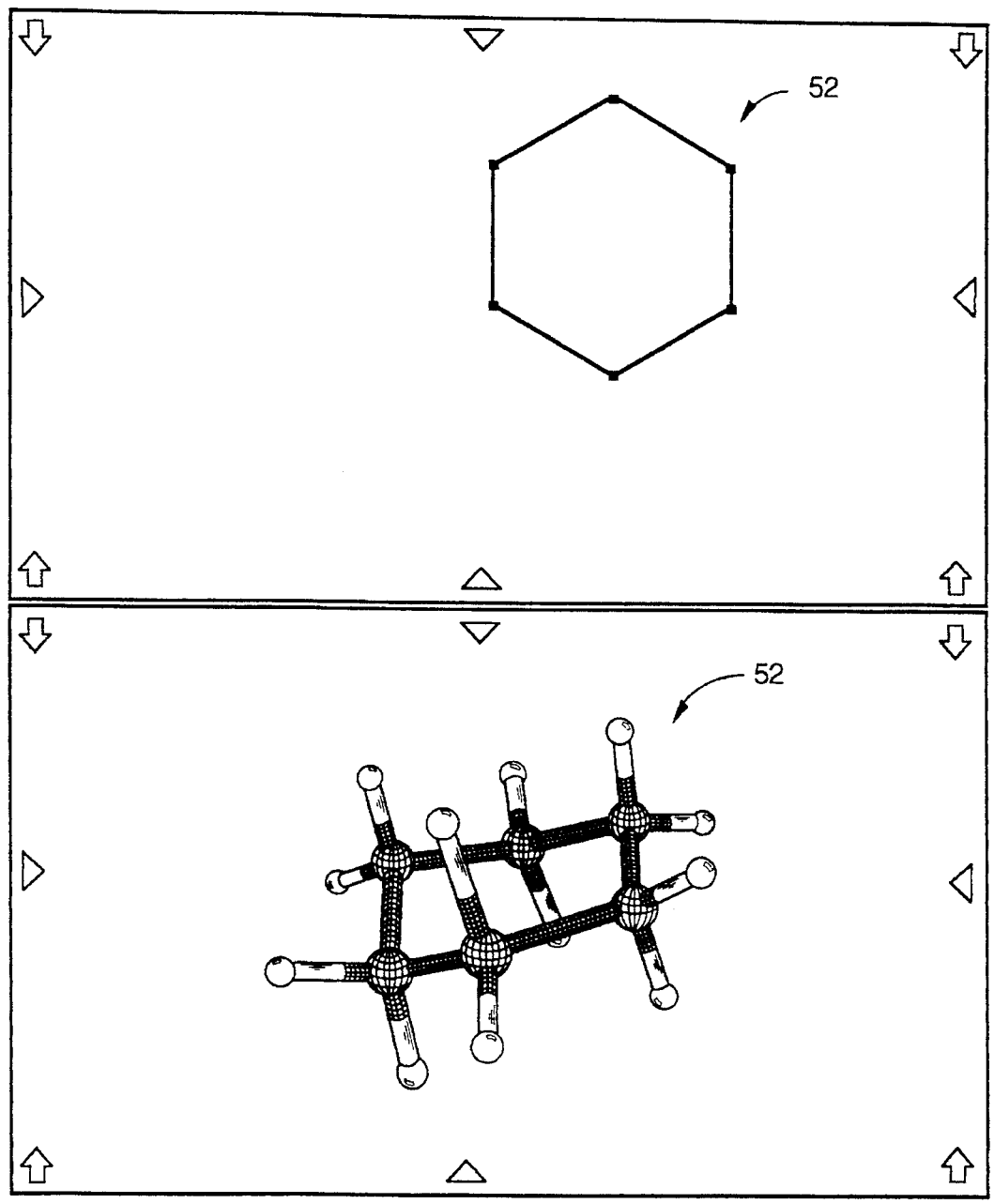
FIG. 13A is an annotated screen print of a display showing a model of a cyclohexane ring in a chair conformer.
Figure 13B:
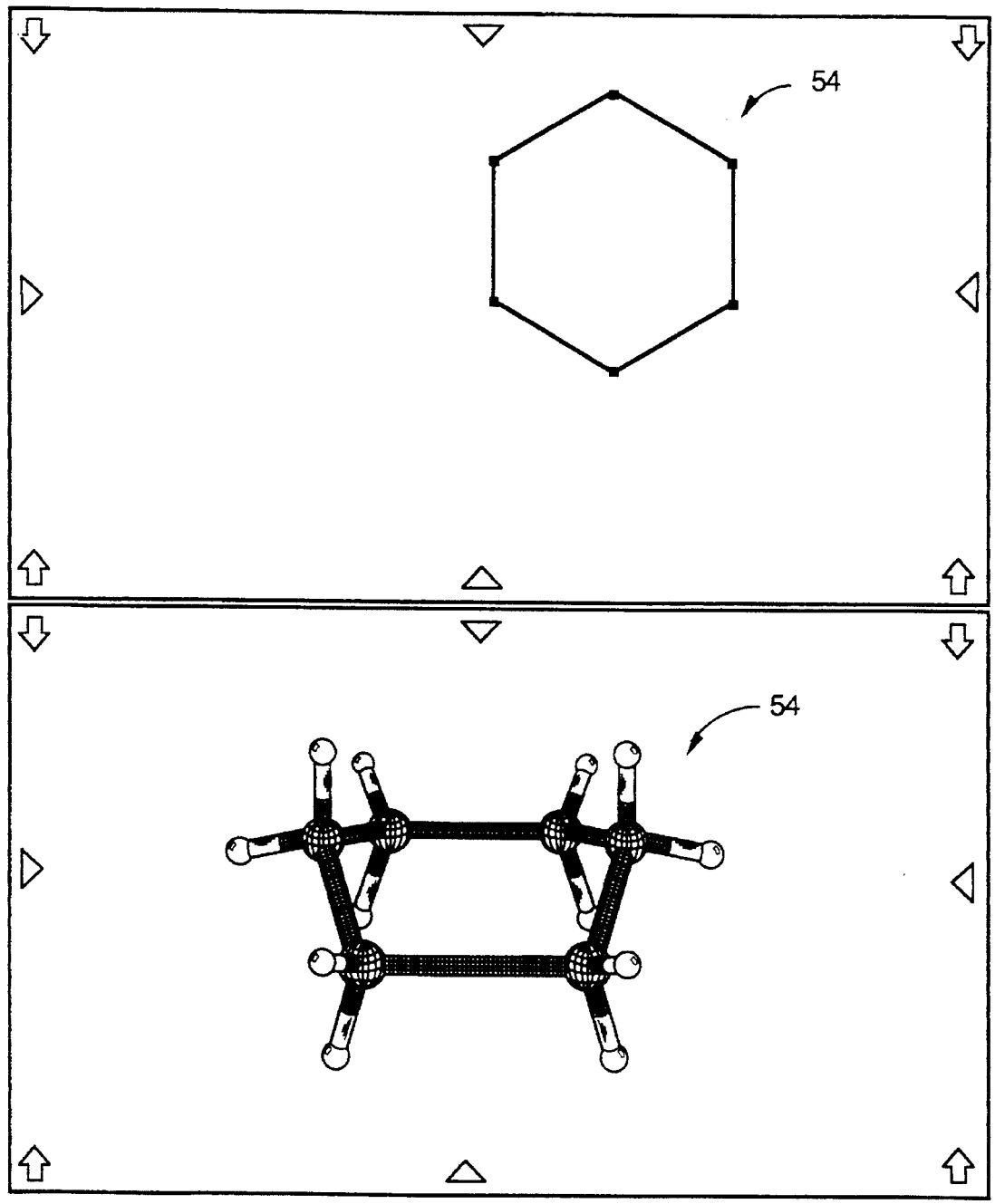
FIG. 13B is an annotated screen print of a display showing a cyclohexane ring in a boat conformer.

A familiar example of molecular deformation concerns the several forms that a ring structure may assume. Many ring structures, such as a cyclohexane ring (i.e. six carbon atoms), have several distinct conformers, and may be converted from one to another without breaking a bond. FIG. 13A shows a carbon cyclohexane ring 52 in a "chair" conformer, for example, and FIG. 13B shows the same ring in a "boat" conformer 54.

Figure 14:
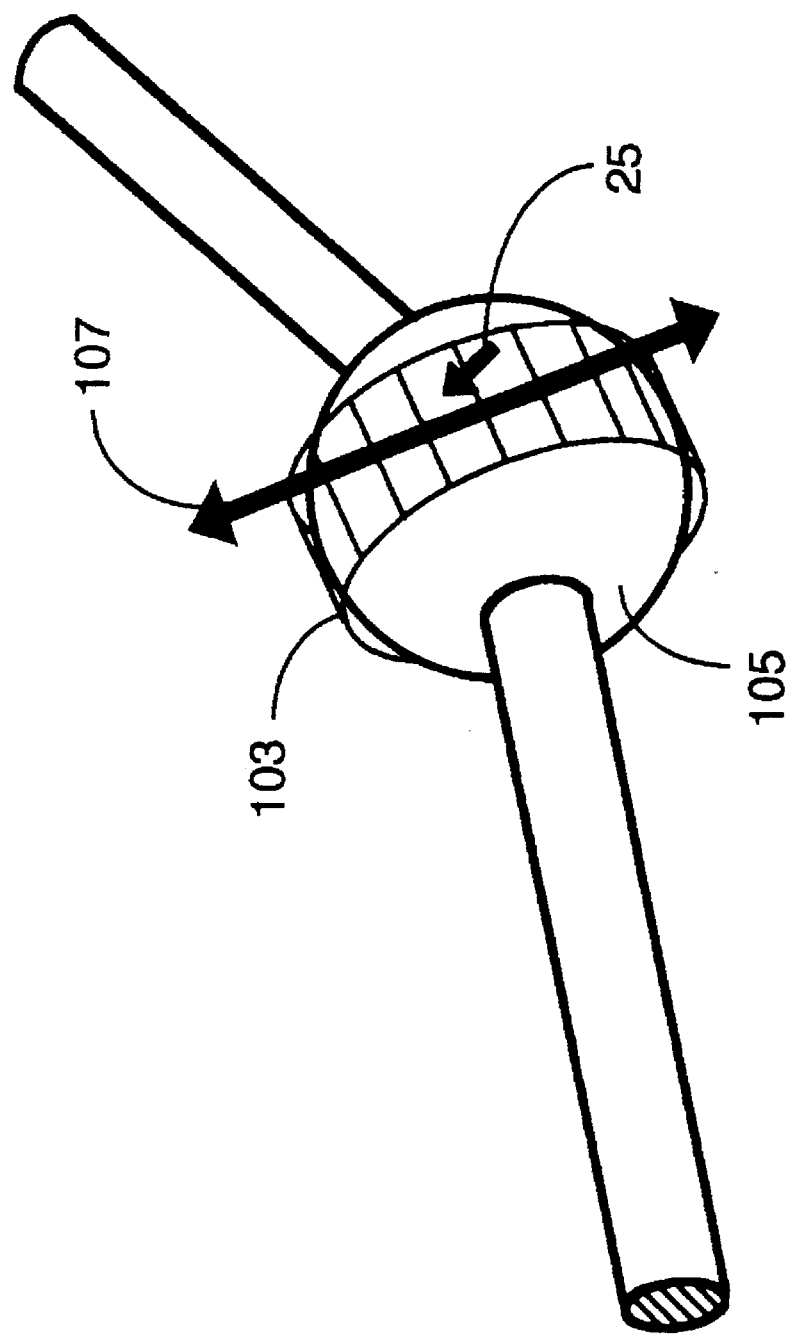
FIG. 14 shows a knurl manipulation element for moving an atom in a model.

In the preferred embodiment a ring atom may be selected, and if the system recognizes that movement of the atom is allowable in the particular structure, altering the geometry of the cyclic array, the system presents a knurl on the atom, much like the knurl the system presents on a bond. FIG. 14 shows a knurl 103 on a ring atom 105. The action of perturbing the geometry by use of an atomic knurl is similar to using a rotational knurl. One moves cursor 25 to the center of the atom with the knurl, depresses the mouse button, and drags in a direction (indicated by arrow 107) substantially at a right angle to the knurl "grooves". It is not necessary that the cursor movement be exactly at a right angle to the grooves, but the movement has to have a component at right angles to the grooves, and it is this component that the system senses to manipulate the knurl.

In the instance of manipulation of a model using an atom knurl, the change in the model is not the same as with bond rotation. Rather the shape of the matrix in the locality of the atom is changed, with some bonds being deflected and others distorted. Again, an example is in changing a ring structure from one form to another; chair to chair, chair to boat, boat to chair, boat to boat, and so forth. The method by which distortion is calculated and displayed is described in more detail below with reference to FIG. 19.

There are instances in investigation when an investigator might want to make a two-handed manipulation of a structure, "grasping" and moving two atoms at the same time. A two-handed manipulation for the purpose of the present description is a manipulation that results in changing the conformation of the molecule by deforming two different parts simultaneously, and typically, the two movements are complementary. An operation that uses both hands but results in a molecule being rotated without perturbing the conformation does not qualify. The difference will become clearer with the following example.

Figure 15A:
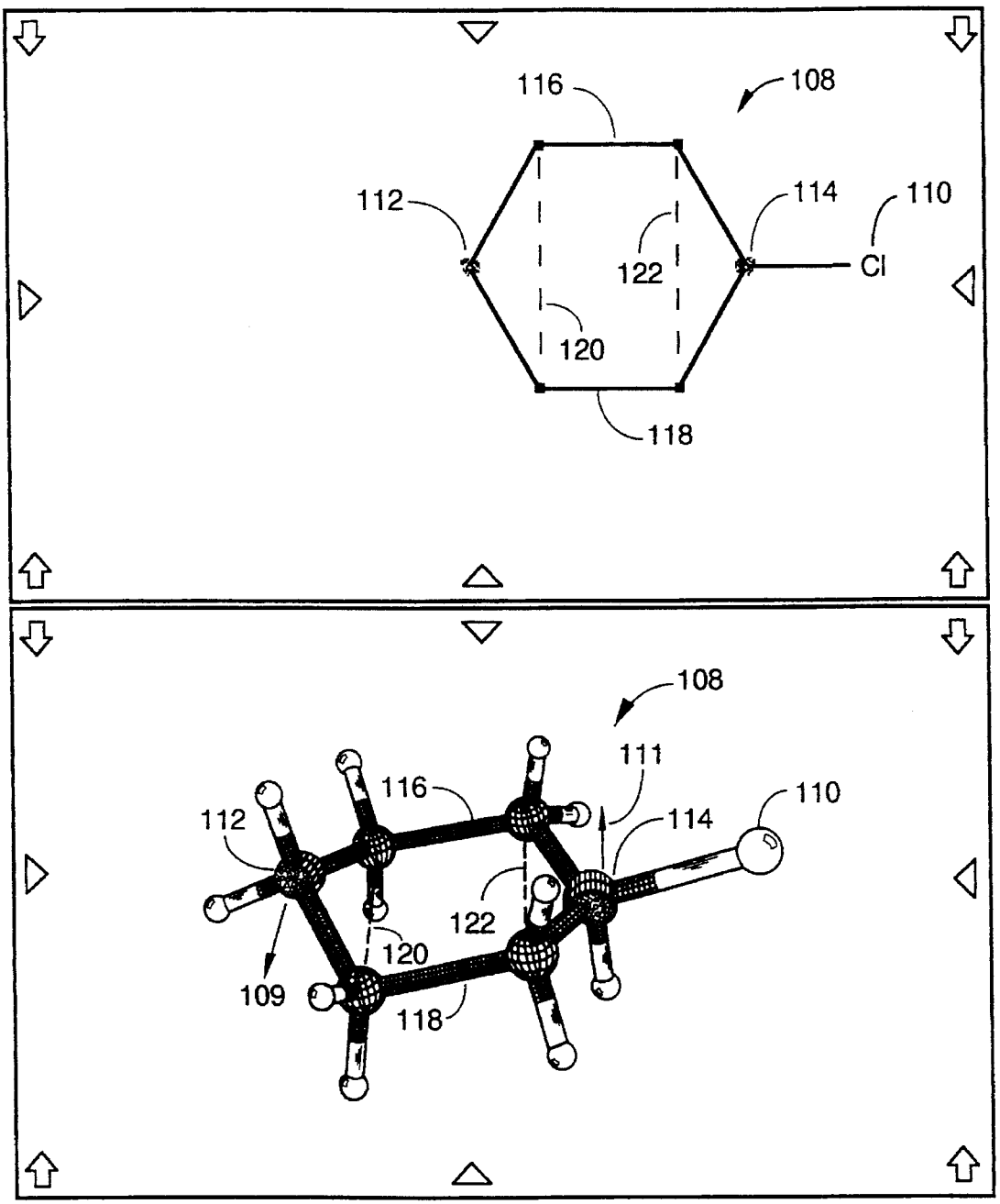
FIG. 15A is an annotated screen print of a display showing a ring molecule in a chair conformer.

FIG. 15A shows a cyclohexane ring 108 bearing a chlorine atom 110 with the ring in a chair conformation in which the chlorine atom is directed toward the periphery of the ring (called an equatorial conformation), with two ring atoms 112 and 114 showing a knurl, indicating that both may be moved. To understand the two-handed manipulation, it is important to visualize the shape of the ring correctly. Bond 116 and bond 118 are parallel and describe a plane. Atoms 112 and 114 do not lie in this plane. Atom 112 is "above" the plane in the view of FIG. 15A, and atom 114 is "below" the plane. This is the source of the "chair" designation. Arrows 109 and 111 indicate the allowable directions of movement. Atom 112, above the plane of the ring, may be rotated downward, and atom 114, below the plane of the ring, may be rotated upward.

The default for the two-handed movement is to hold the portion of the ring stationary that defined the principal plane of the ring. So bonds 116 and 118 will not move. When one manipulates atom 112, a rotation is enforced by the constraints imposed by the ring system around an axis 120, and when one moves atom 114, the rotation is similarly around axis 122.

Figure 15B:
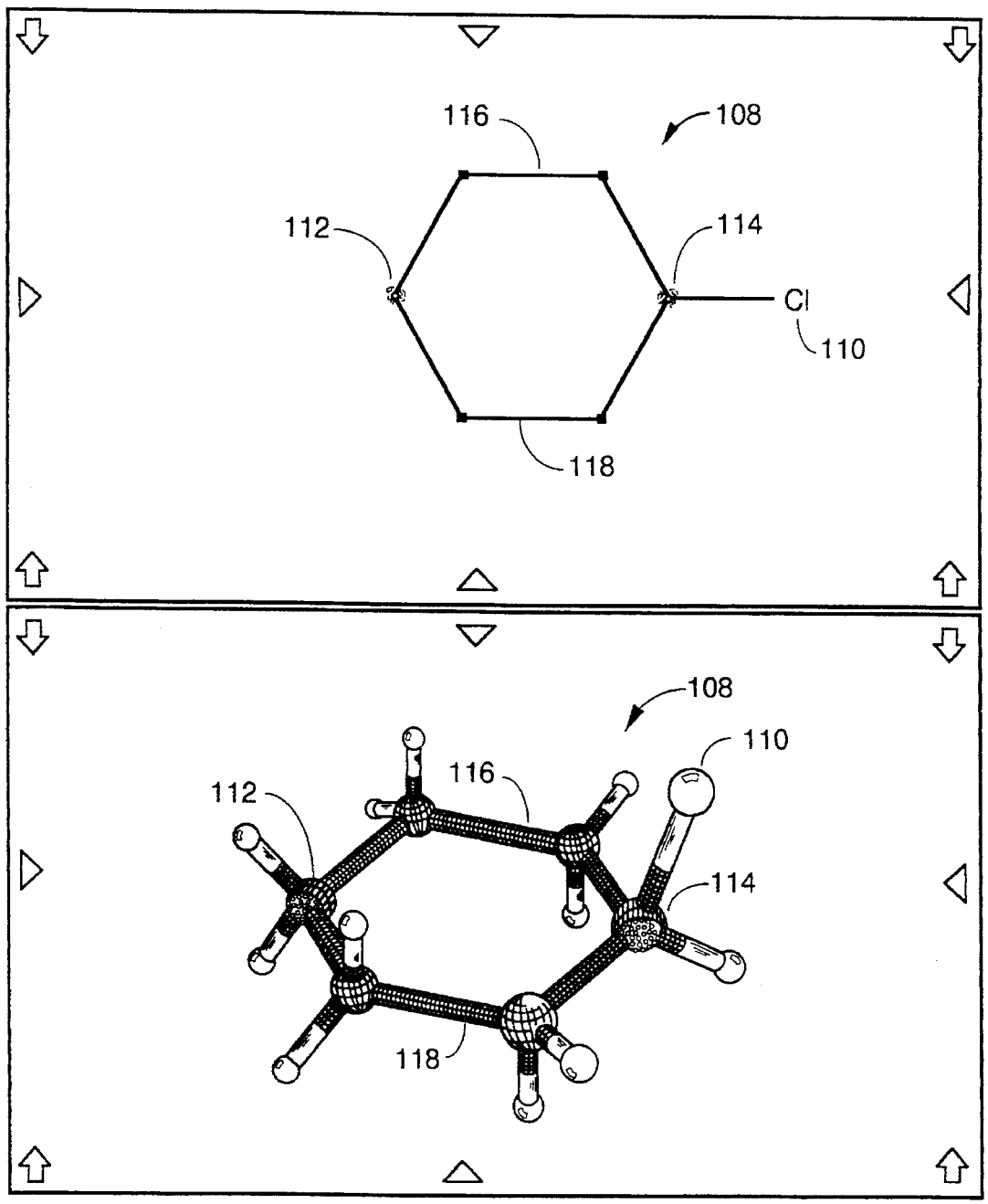
FIG. 15B is an annotated screen print of a display showing the ring molecule of FIG. 15A, but in a boat conformer.

FIG. 15B shows the ring of FIG. 15A (from a slightly different angle) after the two-handed perturbation described above has been applied. Now atom 112 is below the plane of bonds 116 and 118, and atom 114 is above the same plane. The ring is now in the "opposite" chair conformer than in FIG. 15A, and chlorine atom 110 is in what is known in the art as the "axial" position.

With one input device, such as the mouse device so far described, an investigator could conceivably move first one (either one), and then the other atom to accomplish the two-handed movement. This is not the preferred method however, because the two atoms do not move together, and one cannot then investigate the intermediate forms and energy and strain associated with the intermediate forms.

In the preferred embodiment, using a single input device, one holds a "modifier" key depressed on the system keyboard (such as the shift key, although another may be designated and used), and the system makes use of the complementarity of the motions of the atomic centers, noting that atom 112 moves in a "mirror image" of the motion of atom 114. As one moves either atom while both are selected, the system moves the other as well.

In alternative preferred embodiments, to facilitate two-handed manipulations, two input devices are provided, such as two "mouse" devices, two track balls, or other devices, and an investigator may then manipulate with a more natural motion and feel than by using one input device twice. The idea is to provide a computer model and a manipulation paradigm that is as close as possible to a metal or plastic "hands-on" model.

Figure 23A:
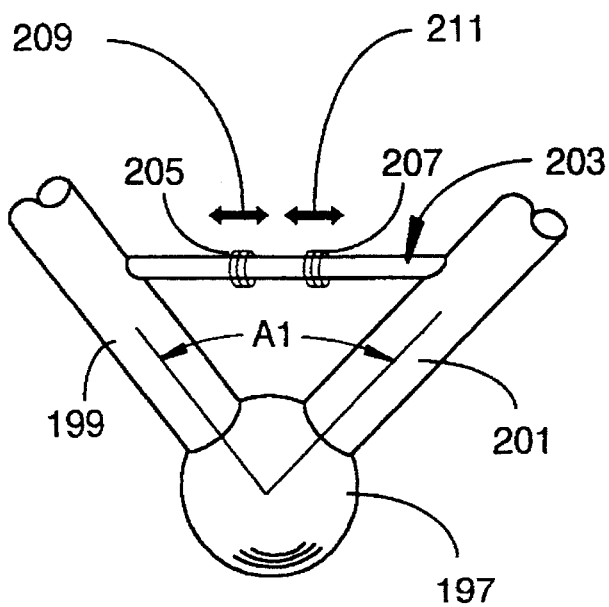
FIG. 23A shows two bonds connected to a single atom in a model of a molecule and an angle bending manipulation element for perturbing the bond angle.
Figure 23B:
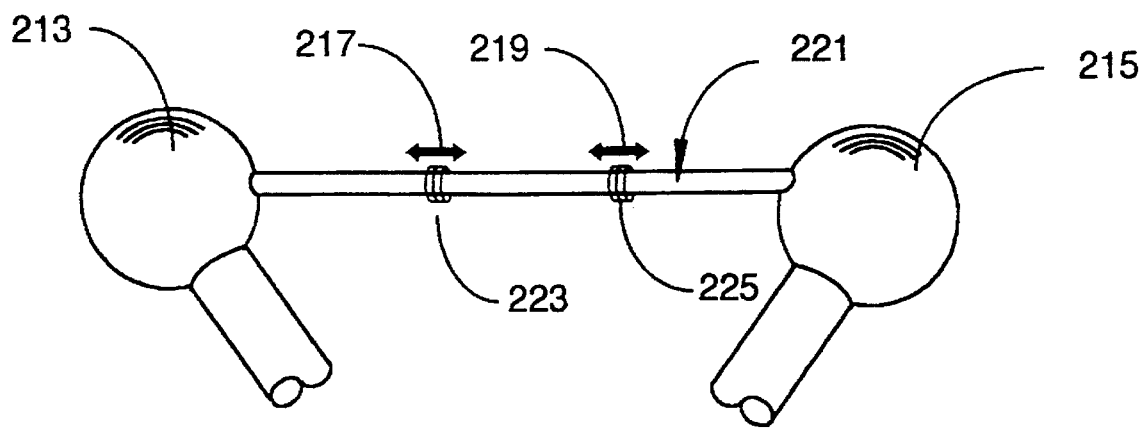
FIG. 23B shows two atoms not directly bonded in a model of a molecule and a manipulation element for changing the interatomic spacing of the two atoms.

Two additional modes of manipulation available for use with PBM modeling (described below) are illustrated in FIG. 23A and FIG. 23B, and are for changing the angle formed by two bonds to a single atom, and for moving two atoms that are not directly bonded either closer together or further apart.

FIG. 23A shows an atom 197 of a molecular structure with two bonds 199 and 201 connecting to the atom and forming an angle A1. A user may select each of the two bonds and an Angle Bend tool from a pull-down menu, and the system will respond by displaying a temporary manipulator 203 for bending the angle between the bonds. Manipulator 203 is a temporary connection between the bonds and has two knurls 205 and 207 that are like the stretch knurls described above with reference to FIG. 10A and FIG. 10B. The user may use the mouse to drag either knurl to bend the angle.

If a user drags knurl 205 toward knurl 207, the effect is to move the knurls closer together, and manipulator 203 is shortened by the magnitude of the drag. This causes the angle between the bonds to become more acute. Exactly the same result is obtained if knurl 207 is dragged toward knurl 205. With either action, both knurls move, and the angle is lessened.

To expand tool 203 and make the angle between the bond greater, a user drags one of the knurls away from the other. The action and result is the same whichever knurl is dragged. Arrows 209 and 211 indicate the drag directions available for each knurl.

FIG. 23B illustrates a manipulation element 221 for pushing two atoms 213 and 215 apart or pulling the same two atoms together. The two atoms are not directly connected by a bond in the molecular model. As in angle bending, a user first selects two atoms, and then an Atomic Distance Tool from a pull-down menu. The system displays manipulator 221 with two knurls 223 and 225. This manipulation mode works just as described above for angle bending. A user may drag either knurl, either toward the other knurl or away from it, and the effect is to shorten or lengthen the manipulator, causing the atoms to be further apart or closer together. Arrows 217 and 219 indicate the direction that the knurls may be moved.

FIGS. 24A and 24B show another way that perturbations may be made in a model by using a manipulator illustrated on a graphical element of the model. This mode is called the Translation manipulation mode, and requires selection via a pull-down menu.

The Translation manipulation mode is designed principally to bend long-chain molecules (or chained portions of more complex molecules) into differing conformers. With the Translation mode enabled, one may select an atom in the molecule, and the system in response displays a handle on the molecule that the user may move to perturb the molecular geometry. As with a knurl, the operation mode is with the cursor. One moves the cursor to the handle, depresses the mouse button, and "drags") the handle in the direction that one wishes to distort the geometry.

The Translation mode is operable only with PBM turned on, and distortion is displayed according to constraints imposed by forces due to bonds and intermolecular interactions. FIG. 24A shows a chain-type molecule 227 with an atom 229 selected and displaying a handle 231. Molecule 227 is shown without any of the ancillary bonds to simplify the illustration. Typically the chain structure will be more complex than that shown.

With PBM turned on and the Translation mode selected, the system displays a handle when the user selects an atom in the chain. To perturb the geometry of the molecule with the handle, the user moves the cursor 25 to the handle, depresses the mouse button, and drags the handle.

FIG. 24B shows the same molecule 227 with atom 229 selected and handle 231 displayed, and the chain molecule has been folded nearly into a ring.

In the atom perturbation described above for ring structures, in the angle bending and the atomic distance modes, and in the translation mode using "handle" manipulators the system accounts for forces and energy due to the perturbations and provides feedback to the investigator as described below in the section titled "Physically Based Modeling".

Figure 28A:
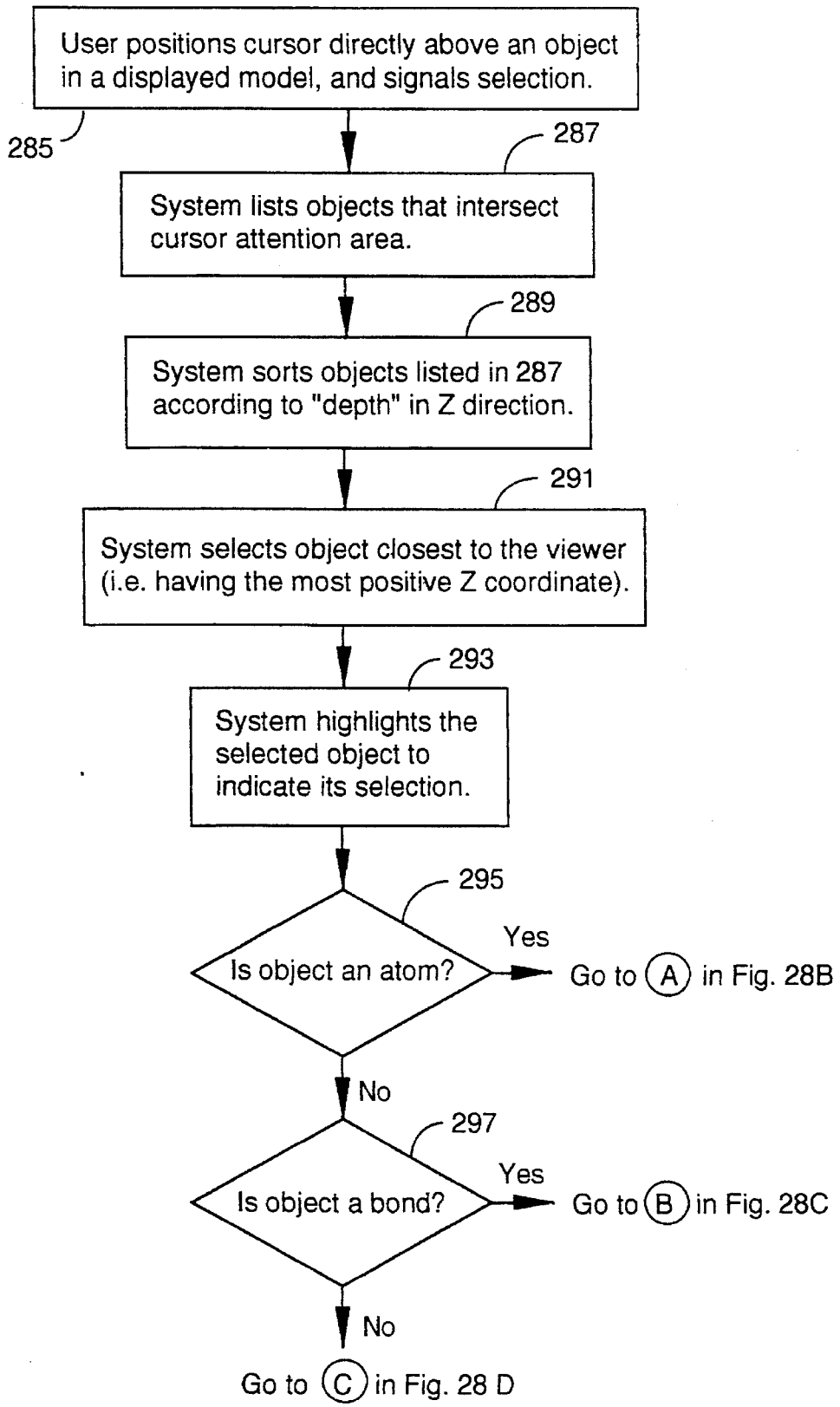
FIG. 28A is a flow diagram showing system operations in selecting graphics objects and displaying knurls.

FIG. 28A through FIG. 28E show the procedures available to the user and the system responses for selecting graphical elements in a model and displaying intuitive knurls for perturbing geometry of a model. The three dimensional editor of the system of the invention is organized as an object oriented system, a type known in the art, and the graphical elements are stored by the system as "objects". In FIG. 28A the procedure of selection and display of knurls begins at step 285 with the user positioning the cursor over an object in the model, such as a bond or an atom, and signalling selection, typically by momentary depression of a button on the mouse device.

In the selection process, the cursor is associated with a small display area that moves with the cursor, rather than the point coordinate of the cursor. This small area, which may be configured by the user when setting up the system, is called the cursor attention area. When the user selects, the system lists all objects in the model that intersect the cursor attention area (step 287). At step 289 the system sorts the list of intersecting objects according to depth in the Z direction. At step 291 the system selects from the list the object closest to the user, that is, the object with most positive Z coordinate, as the Z direction is more negative into the screen. In step 293 the system highlights the selected object to indicate the fact of selection by the user. Highlighting is a technique well known in the art.

Having selected and highlighted a particular object, the system queries the type of object from information stored in the object oriented memory. At step 295 the system queries "is the object an atom?". If the answer is Yes, control goes to (A) in FIG. 28B.

Figure 28B:
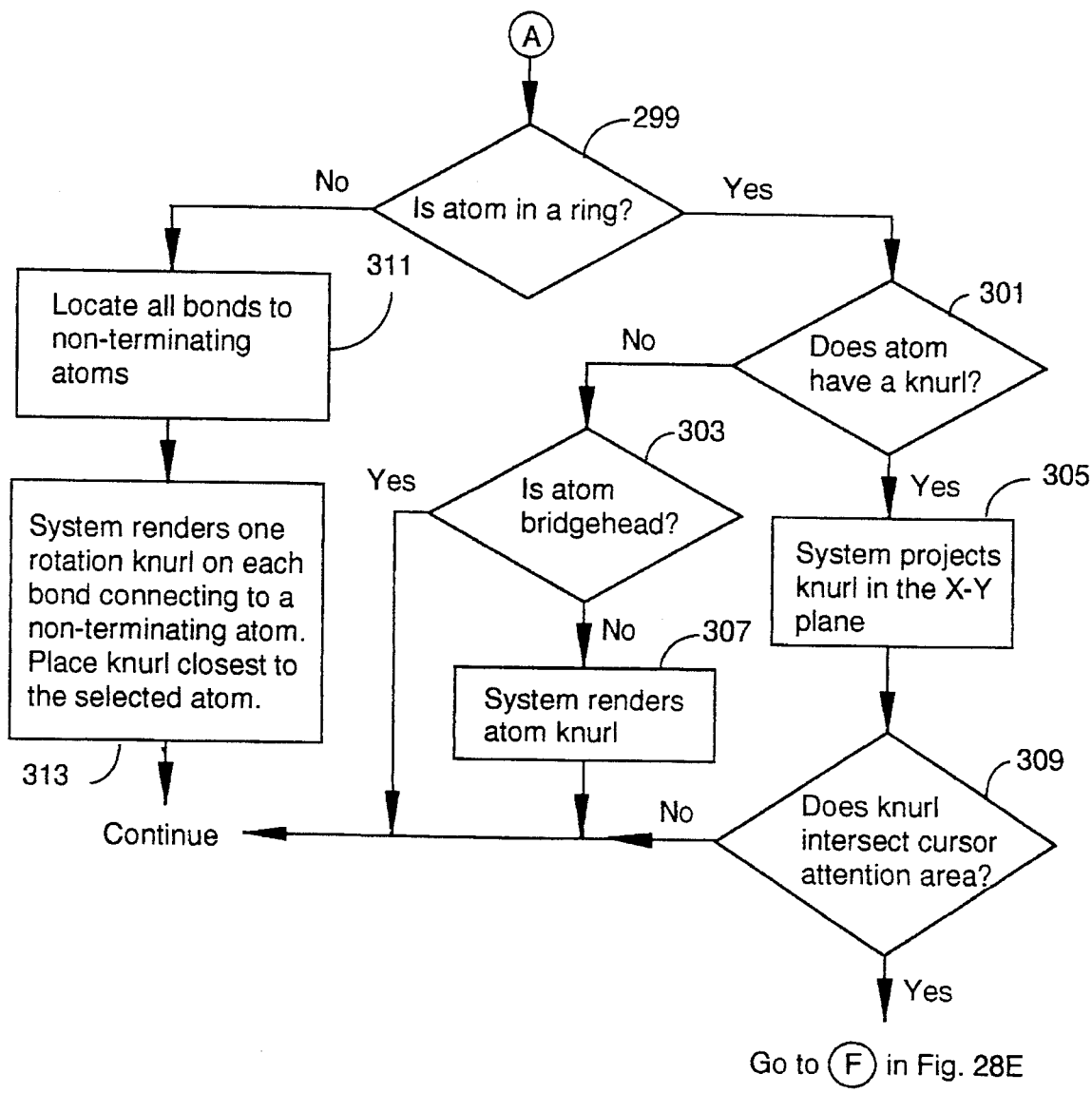
FIG. 28B is a flow diagram enlarging on FIG. 28A.

In FIG. 28B the system asks in step 299 if the selected atom is in a ring structure. If it is not, control goes to step 311, and the system locates all bonds to non-terminating atoms. After locating all the bonds from the selected atom to non-terminating atoms, the system renders (displays) a rotational knurl on each such bond, and places the rotation knurl closer to the selected atom than to the atom connected by the bond.

Returning to step 299, if the answer is yes, the atom is an atom in a ring structure, control goes to step 301 to query if the atom selected already displays a knurl. This determination is necessary, because in the selection process, a user may select an object without a knurl, in which case the system response is to display a knurl (if a knurl is appropriate), or the user may select an object for which the system already displays a knurl, in which case the system response is to track cursor movement on the knurl while the mouse button is depressed (dragging), and use that movement to perturb the geometry of the model.

In step 301 then, the system determines which response is appropriate. If the atom is in a ring and has no knurl, the system queries in step 303 if the atom is "bridgehead". Bridgehead is a term common in chemistry, and indicates the atom is bonded such that it may not be moved to perturb the geometry. If the atom is bridgehead (Yes), the system renders no knurl, and control goes back to waiting for additional user input (Continue).

If at step 303 the atom is determined not to be bridgehead, the system renders an atom knurl in step 307 and then control goes back to waiting for input.

If in step 301 the system determines the atom already has a knurl displayed, then the appropriate response is perturbation. Control goes to step 305. The system projects the knurl into the X-Y plane, and in step 309 determines if the projected knurl intersects the cursor attention area. If so, control goes to (F) in FIG. 28E.

Figure 28C:
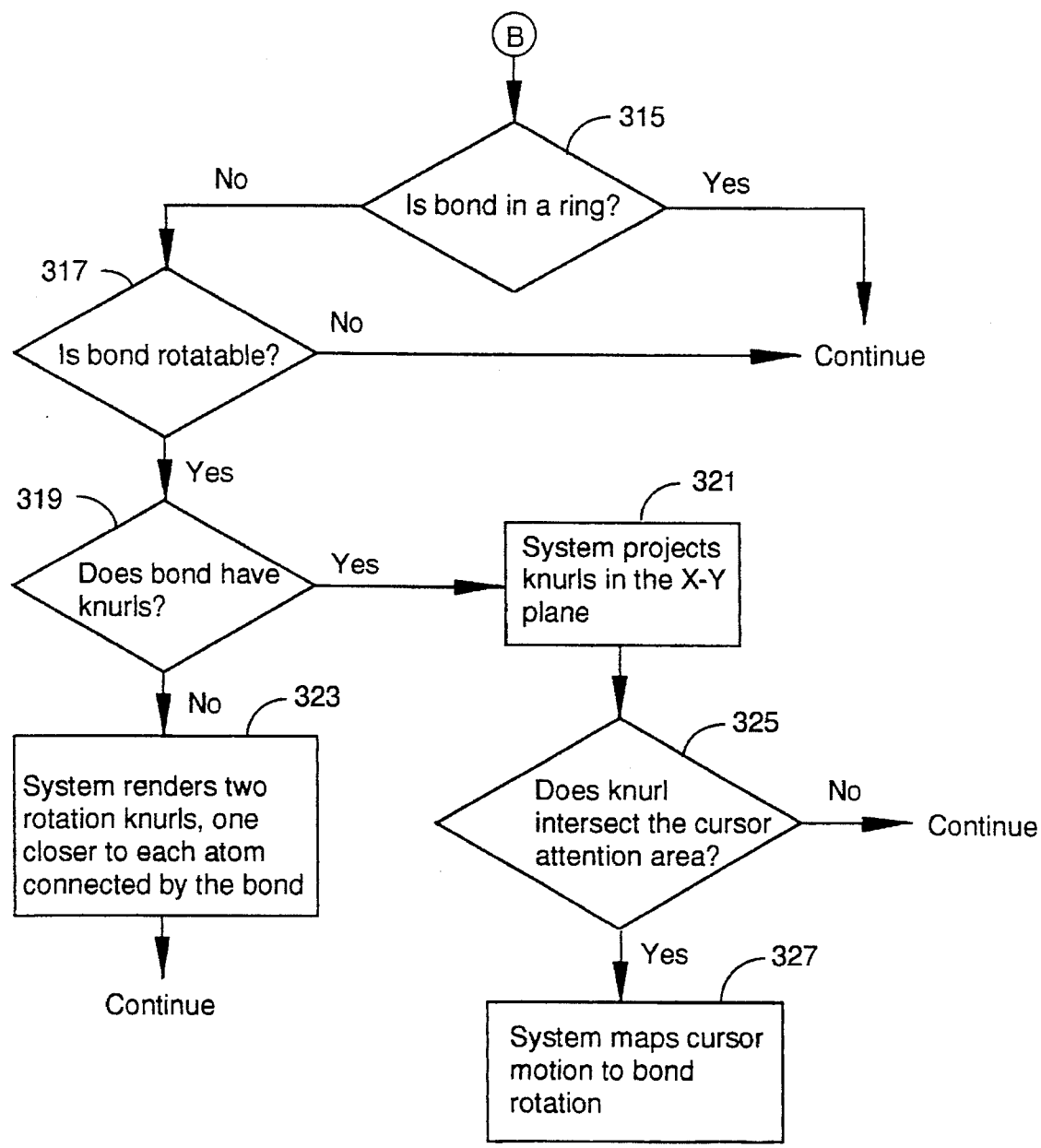
FIG. 28C is a flow diagram enlarging on FIG. 28A.
Figure 28D:
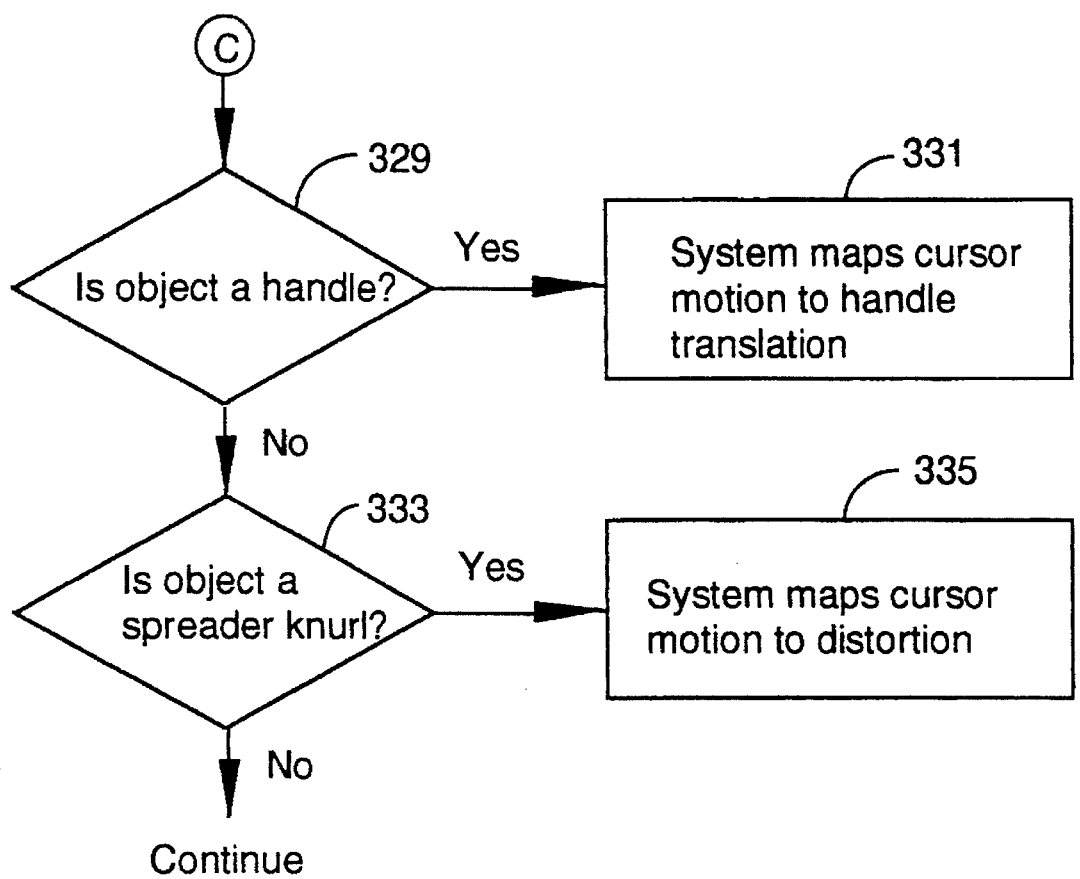
FIG. 28D is a flow diagram enlarging on FIG. 28A.
Figure 28E:
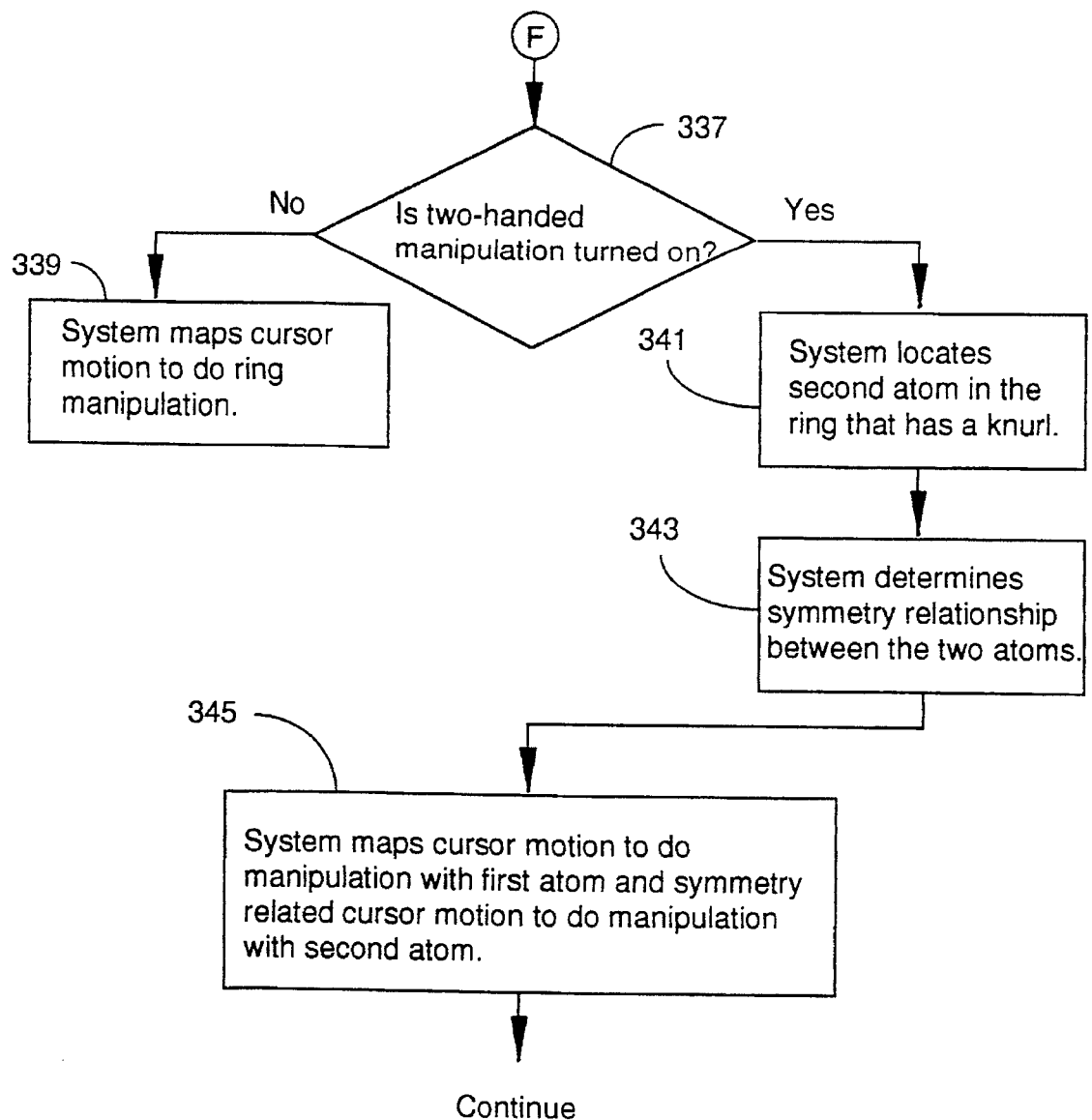
FIG. 28E is a flow diagram enlarging on FIG. 28A.

In FIG. 28E, at step 337, the system queries if the Two-Handed Manipulation function is turned on. If so, control goes to step 341 and the system locates the second atom in the ring structure that has a knurl. In step 243 the system determines the symmetry relationship between the two atoms from the data base, and in step 345 tracks the cursor motion to do manipulation with the first atom and symmetry related cursor motion to do manipulation with the second atom. The process of tracking and applying increments of cursor movement is described in detail below with reference to FIG. 18.

If at step 337 the system determines that Two-Handed Manipulation is turned off, the system maps the cursor motion to do ring manipulation one-handed (step 339). Again, the process of tracking and perturbation is explained below with reference to FIG. 18.

Returning to step 295 in FIG. 28A, if the object is not an atom, control passes to step 297, and the system queries whether the selected object is a bond. If so, control goes to (B) in FIG. 28C.

In FIG. 28C, at step 315, the system queries whether the selected bond is in a ring structure. If it is, control returns to waiting for further user input, as bonds in ring structures are not rotatable. If the bond is not in a ring, control goes to step 317, and the system queries whether the bond is rotatable, which information is available from structural information stored in the object oriented data base. If the bond is not rotatable (it might be, for example, a double bond), control goes back to waiting for additional user input.

If the bond is found to be rotatable, the system queries at step 319 whether the bond already has knurls displayed. If it does, control goes to step 321 and the system projects the knurls into the X-Y plane. In step 325 the cursor questions whether the projected knurl intersects the cursor attention area. If not, control goes to waiting for additional user input, and if so, the system maps the cursor motion to bond rotation.

If at step 319 the bond has no knurls, the system renders two rotation knurls (step 323), one closer to each atom connected by the bond. Then control goes to waiting for further user input.

Returning to FIG. 28A, at step 297, if the selected object is determined not to be a bond, control goes to (C) in FIG. 28D. In step 329 the system queries whether the selected object is a handle. If so, the system maps cursor motion to handle translation (step 331). If the object is not a handle the system questions in step 333 whether it is a spreader knurl (the last of the object possibilities). If not, control returns to waiting for further input. If the selected object is a spreader knurl, the system maps the cursor motion to distortion at step 335.

FIG. 29A through FIG. 29F show in detail how the system displays knurls in response to user selection of objects in models of molecules. The process begins when the user selects an object for which a knurl is to be displayed (step 347). The procedure the system follows to determine whether a knurl is to be displayed is described above relative to FIG. 28A through FIG. 28E. After the selection, in step 349, the system retrieves from memory precomputed end points of line segments that compose a cylinder of unit length and unit radius. This is the "generic" cylinder for scaling and displaying knurls.

After retrieving the data for a generic knurl, the system questions in step 351 whether the knurl to be displayed is an atom knurl. If it is, control goes to (A) in FIG. 29B. At step 359 in FIG. 29B the system scales the knurl cylinder to 1.1 times the displayed radius of the atom. In step 361 the system scales the length of the knurl cylinder to 0.3 times the radius of the selected atom. In step 363 the system increases the tessellation of the knurl cylinder about its axis. This provides the intuitive "grooves" previously described for the knurl.

In step 365 the system locates two bonds extending from the atom. In step 367 the system orients the knurl cylinder's axis to lie in the plane defined by the axes of the two bonds, and orthogonal to a line that bisects the angle between the two bonds. The system determines the display position necessary within these constraints to center the knurl cylinder on the atom. In step 369 the system renders the knurl on the atom.

Returning to FIG. 29A at step 351, if the knurl to display is not an atom knurl, the system queries at step 353 whether the knurl is a rotation knurl for a bond. If it is, control goes to (B) in FIG. 29C.

In FIG. 29C, at step 371, the system scales the radius of the knurl cylinder to be 1.1 times the displayed radius of the bond cylinder. In step 373 the system scales the length of the knurl cylinder to be 0.2 times the length of the bond cylinder. In step 375 the system increases the tessellation of the knurl cylinder about its axis. In step 377 the system orients the knurl cylinder's axis to be coincident with the axis of the bond cylinder. The system then determines the display position necessary to render the knurl cylinder 0.1 times the bond distance away from the closest atom in step 379. Then in step 381 the system renders the knurl in the display. After rendering the knurl, the system waits for further user input (continue).

Returning to step 353 in FIG. 29A, if the knurl to be rendered is not a bond knurl the system questions in step 355 whether it is a stretch knurl. If so, control goes to (C) in FIG. 29D. In FIG. 29D, at step 383, the system questions whether the knurl is to be an angle bend knurl. If it is, the system locates the midpoints P1 and P2 of the two bonds selected for the angle bend in step 395. At step 397 the system scales the length of the knurl cylinder to connect P1 and P2, scales the radius of the connecting cylinder to be 10.0 picometers (in world coordinate system), then orients the connecting cylinder to lie between the two points with its axis coincident with a line connecting the points.

At step 399 the system renders the connecting cylinder. At step 401 the system retrieves the unit knurl cylinder. At step 389 the system scales the length of the knurl cylinder to be 0.1 times the original distance between P1 and P2. In step 391 the system scales the radius of the knurl cylinder to 1.1 times the radius of the connecting cylinder. In step 393 the system orients the knurl cylinder's axis to be coincident with a line between P1 and P2. Then control passes to (E) in FIG. 29F.

If in step 383 in FIG. 29D the system determines the knurl is not an angle bend, the system locates the coordinates of the two points defining the distance to be changed as P1 and P2. In step 387 the system questions if P1 and P2 are directly connected. If they are not, control passes to step 397 described above. This is the case for a spreader bar between two atoms not directly connected. The system then follows steps 397, 399, 401, 389, 391, and 393, rendering a connecting cylinder and preparing the knurl cylinder for display.

If in step 387 the system determines the two points defining the distance to be changed are directly bonded, control goes then directly to step 389 and the unit knurl cylinder is scaled to be displayed on the bond between P1 and P2. At the end of each path control passes to (E) in FIG. 29F.

In each case of a spreader bar or of stretch knurls as described in FIG. 29D there are to be two knurls rendered on the bond or spreader bar, for manipulation to lengthen or shorten the distance between the points. In FIG. 29F, at step 417, the system determines the position of the knurl cylinder to be 0.35 times the distance along the length of the connecting cylinder or bond. At step 419 the system renders the knurl in the display. The system then determines the position to be 0.65 times the length of the connecting bar or bond in step 421, and renders the knurl in the display again in step 423. The result is two knurls displayed on the spreader bar or bond.

Returning to FIG. 29A, if the system determines in step 355 that the knurl to be displayed is not a stretch knurl, the system questions in step 357 if the knurl is to be a handle. If not, the system waits for further input (continue). If the knurl is to be a handle, control goes to (D) in FIG. 29E.

At step 403 in FIG. 29E the system scales the radius of a cylinder for a handle to be 10.0 picometers (in world coordinates and 100.0 picometers in length. The system then locates the geometry of all bonds extending from the selected atom to non-terminating atoms. At step 407 for all bonds the system goes to step 409 and orients the axis of a handle to be coincident with the axis of the particular bond. The system then translates the handle cylinder to the referenced atom such that the axis of the handle cylinder is anti-parallel to the axis of the bond (step 411). That is, the handle extends from the referenced atom opposite the bond extension and in line with the bond axis. The system then renders the handle for that bond in step 413. At step 415 the system asks if there are other bonds extending from the referenced atom. If there are, the system loops back to step 407 and goes through the process of preparing and displaying a handle for each of the other bonds. After the last handle displayed the system waits for additional user input (continue).

Physically Based Modeling

In the preferred embodiment, a user can turn PBM on or off by a keystroke or by selection from a pull down menu. PBM comprises the accounting of interatomic and restoring forces during manipulation, and the variations in both energy and geometry that result from the perturbation. It is well known, for example, that molecular structures do not behave as the benign ball-and-tube models described thus far. Rather, there are forces involved with the bonds and between atoms in a chemical structure. When one rotates a bond or displaces an atom in the structure, stresses result, and the various molecular components exert restoring forces. Moreover, the relative energy of a molecule is changed from the non-perturbed condition. It is also well known that many chemical structures may exist in a stable fashion (local energy minima) in more than one geometry. A good example is the familiar cyclohexane ring, which has several conformers with the ring arranged in "chair" and "boat" forms. Chain-type molecules may also exist in different conformers. In an investigation of a chemical structure and its properties, these forces and relative energy levels provide clues to such objects of investigation as function, reactivity, and selectivity.

The idea of PBM is to provide a tool to simulate molecules in as "real" a manner as possible, so an investigator may study all of the characteristics that determine molecular properties. With PBM enabled, the system allows an investigator to select structural elements and perturb the geometry by action on the knurls that the system displays, much as described above for the case with PBM disabled. PBM, however, accounts for all of the energy and force components involved in the molecular structure, and provides feedback to an investigator in a number of ways.

One way the system feeds information back to an investigator is by simulating changes in geometry that result from the intermolecular and bond forces when one moves a part of the molecule. For example, when one rotates a bond by action on a knurl, if there is a structural component that rotates, and the rotation would cause that structural component to interfere with a part of the non-rotating structure, the system accounts for the forces and calculates the resulting deflection and/or deformation of both the rotating and non-rotating structural components to avoid the interference. The two groups may be seen to perform a coordinated rotation to relieve the steric congestion as it occurs. As another example, when one moves a molecule in a ring structure, the system accounts for all the internal forces, and displays the deformation of the entire structure as a result of the induced perturbation. The method the system uses to calculate and display the deformation is described in detail below with reference to FIG. 18.

Another feature of PBM is an ability to display force feedback to indicate an energy barrier being explored. For example, an investigator selects an atom which then displays a knurl, and manipulates the structure by using the mouse to "push" the atom out of its stable position. With PBM on, the system provides visual feedback. All stressed internal coordinates, which includes stressed atoms and bonds, are displayed in color to indicate the stressed condition. Typically the colors change relative to the magnitude of stress. The stressed condition is also reported as strain in field 115 in the 2D/3D display as shown in FIG. 3 and described in further detail below. In an alternative embodiment audio feedback is provided as well as the visual representation. In the case of audio feedback, typically the pitch is keyed to rise relative to greater force, providing an intuitive feedback to the investigator. If the pitch rises very rapidly, then the energy gradient is recognized by the investigator to be steep. In yet another embodiment, the distance the mouse device has to be pushed to provide unit deflection is keyed to the magnitude of the restoring force. A user has to move the mouse device further for a stronger resistance to accomplish the same deflection that can be accomplished with a shorter movement for a lesser restoring force.

When a chemical structure is displayed, either by retrieval from storage, by editing of an existing molecule, or by construction, the energy of the molecule, calculated as the energy of formation, is displayed in the 2D/3D window near the lower left corner in display field 113 (FIG. 3). The units are KJoule·mol$^{-1}$ in the preferred embodiment, but could be in any of several other convenient units. Field 115, directly below the energy term in the 2D/3D window displays the "strain" on a structure as a result of perturbation in PBM. The strain is displayed in the same units as the energy of formation, and varies as the magnitude of perturbation varies, but not necessarily linearly. For example, if one selects an atom knurl and distorts a structure by that knurl, the energy change (addition) caused by the distortion is displayed as strain. The energy of formation term does not change during distortion, and thus the strain is a "delta" energy term. The methods the system uses to calculate strain are described more fully below.

The energy term and the strain term are relative to the starting point; that is, the time that one selects a manipulation element to move to alter the conformation. The default operation is that one may select a mode for perturbing a molecular model, displace movable elements, for which the system calculates and displays the strain, and stop, then move some more, and so forth. The system continues to calculate and display. This procedure allows contemplation and interaction as the investigation proceeds. At any time during perturbation one may also select a minimization function called Optimize from the 3D Tools menu (FIG. 3). In response to the Optimize signal, the system calculates the "nearest" local minima conformation without moving to a higher energy conformation and displays the molecule in that local energy minimum conformation.

Figure 22:
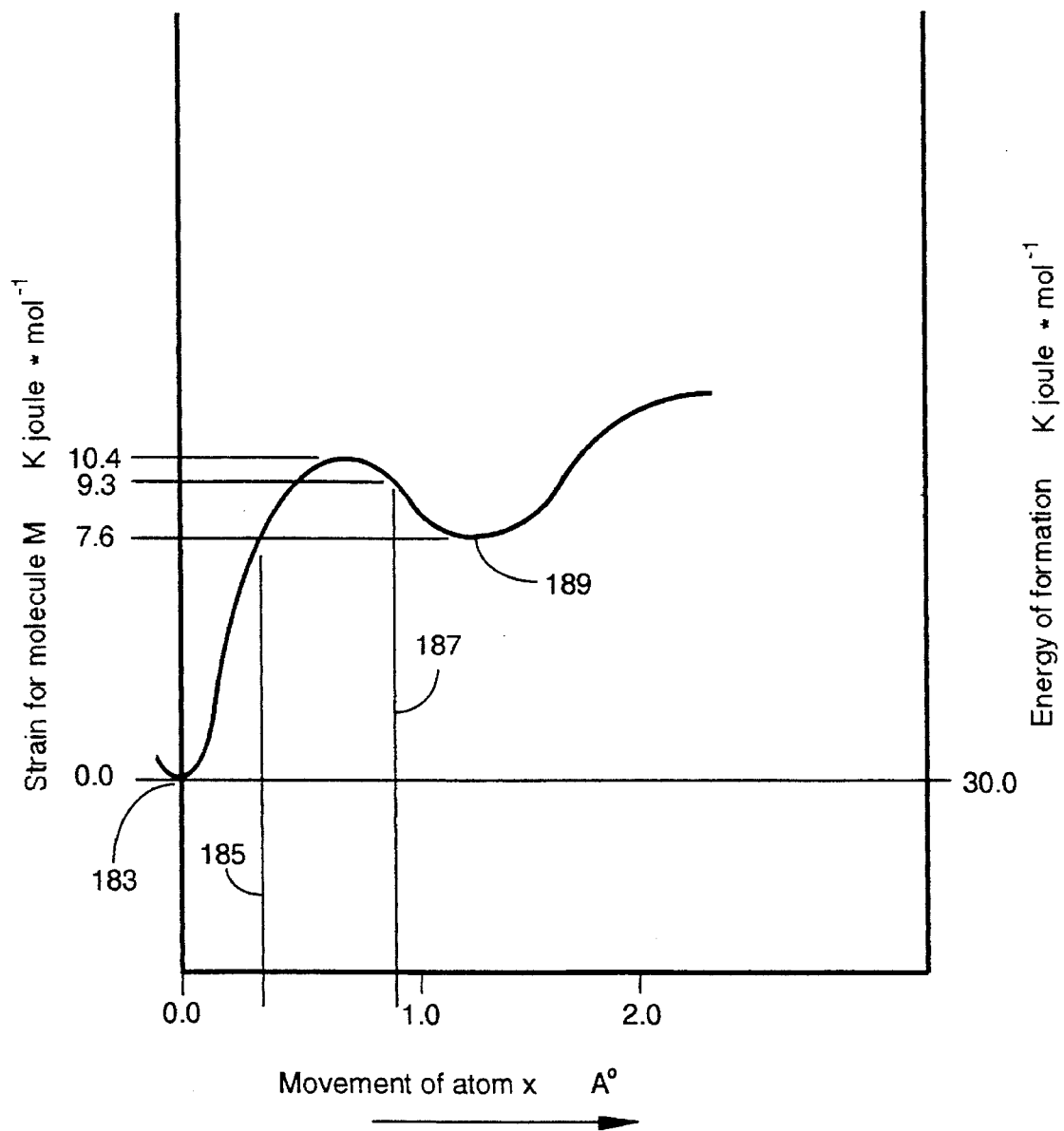
FIG. 22 is a graph of movement of a theoretical atom in a model to illustrate the nature of changes in energy of formation and strain.

FIG. 22 is a graph of energy vs. movement of a molecule in a purely hypothetical situation to illustrate the system operation. In FIG. 22 one has selected an atom "x" in a molecule "M", and the graph shows the strain as one moves atom "x". When atom "x" is selected the energy is the energy of formation of the conformer at that time, shown as 30.0 KJoule·mol$^{-1}$, and the strain is 0.0 (point 183). When atom "x" has been moved to the extent of line 185, the strain is 7.6 KJoule·mol$^{-1}$. As the atom is moved, the system calculates the strain and also changes in the positions of atomic centers for all the atoms of the molecule. If one stops moving atom "x" the conformation remains static, and the strain term stays constant, until one moves atom "x" again, or selects to minimize the conformation (Optimize). If one selects to Optimize, the conformation and strain go back to what was displayed at point 183.

If one moves atom "x" to the extent of line 187, the strain moves through a local maximum at 10.4 KJoule·mol$^{-1}$ and back down to 9.3 KJoule·mol$^{-1}$. If one selects to Optimize from this position the conformation and strain move down the energy slope to point 189, with strain of 7.6 KJoules·mol$^{-1}$. Point 189 is a local minimum representing a stable conformation of molecule "M". If one exits PBM with molecule "M" in the conformer represented by point 189, and returns at another time to again perturb the molecule by atom "x", the new total energy will be the sum of the original (30.0) and the strain at point 189 (7.6) or 37.6 KJoule·mol$^{-1}$. This is the new starting point.

The local minimizer in the invention uses the Polak-Ribiere conjugate gradient method, which is explained in detail in: W. H. Press, B. P. Flannery, S. A. Teutolsky, and W. T. Vetterling, "Numerical Recipes in C", Cambridge University Press, 1988, pp. 317–323.

With PBM enabled, computation of displacement of atoms by the system is based on energy gradients with respect to position in addition to cursor displacement. Displacement from the center of the selected knurl is computed just as described above for the case without PBM, and this displacement is used to move those atoms in the model that are directly controlled by the knurl. All atoms are then moved by computing the gradient of an energy function with respect to the coordinates of the atoms and applying that gradient with a scaled step size to each atom.

There are several methods that may be used to compute the step size, and all have been used in alternative embodiments of the invention. The simplest is heuristic, in which a small displacement (step size) is selected as an arbitrary function of the size of the gradient components and the associated energetic contribution. This is rapid, but not completely accurate. Another method uses normal coordinates to resolve the effects on the energy of perturbing the geometry of a molecule. The normal coordinates represent an orthonormal basis for the motions of the molecule computed from the eigenspectrum of an arbitrary spanning subspace. The square root of an eigenvalue associated with an eigenvector indicates the effect on the energy of a unit perturbation along a normal coordinate represented by that eigenvector. The system can then compute the stepsize as a function of the energy change the user introduced by moving the atoms attached to the knurl. This is a highly accurate method, but since the normal coordinates are conformationally dependent, the computation is relatively slow.

Another method, which is the preferred method in the invention, consists of integrating the differential equation represented by the incremental gradients to anticipate the user's next move as a function of a sequence of recent gradient calculations. This is a technique that has been used in flight simulation equipment in the absence of more powerful computers. Well known integration techniques such as Bulirsch-Stoer and predictor-corrector techniques are used. These are among the fastest integrators known, and produce highly accurate results, especially for systems with well-behaved higher-order derivatives, which is true of the force field used in the present invention. A good discussion of these techniques, including step size selection, can be found in the book referenced above: W. H. Press, B. P. Flannery, S. A. Teutolsky, and W. T. Vetterling, "Numerical Recipes in C", Cambridge University Press, 1988, pp. 574–597. Predictor-corrector techniques are on pp 589–592.

The system evaluates the energy, restoring forces, and the deformation of a molecular model by use of a force field. Published force fields known in the art include Discover, CHARMm, Dreiding, AMBER, and MM3. The function used in the present invention is based mostly on the CHARMm function, but has been customized for the invention. References for force fields including the CHARMm force field follow:

1. B. R. Brooks, R. E. Bruccoleri, B. D. Olafson, D. J. States, S. Swaminathan, and M. Karplus, "CHARMm: A Program for Macromolecular Energy, Minimization, and Dynamics Calculations." J. Comp. Chem. vol. 4, 187–217 (1983).
2. S. Lifson and A. Warshel, "Consistent Force Field for Calculations of Conformations, Vibrational Spectra, and Enthalpies of Cycloalkane and n-Alkane Molecules." J. Chem. Phys. vol. 49, 5116–5129 (1968).
3. A. Warshel, M. Levitt, and S. Lifson, "Consistent Force Field for Calculation of Vibrational Spectra and Conformations of some Amides and Lactum Rings." J. Molecular Spectrosc. vol 33, 84–99 (1970).
4. N. Allinger, J. Am. Chem. Soc. vol 99, 8127 (1977).
5. S. J. Weiner, P. A. Kollman, D. A. Case, U. C. Singh, C. Ghio, G. Alagona, S. Profeta Jr., and P. Weiner, "A New Force Field for Molecular Mechanical Simulation of Nucleic Acids and Proteins." J. Am. Chem. Soc. vol 106, 765–784 (1984).
6. S. J. Weiner, P. A. Kollman, D. T. Nguyen, and D. A. Case, "An All Atom Force Field for Simulations of Proteins and Nucleic Acids." J. Comp. Chem. vol. 7, 230–252 (1986).
7. L. Nilsson and M. Karplus, "Emperical Energy Functions for Energy Minimization and Dynamics of Nucleic Acids." J. Comp. Chem. vol 7, 591–616 (1986).

A force field is a mapping from a vector of coordinates that unambiguously describe a conformer into the real numbers. The coordinates may be cartesian, internal, local symmetry, normal, and so forth. A force field function as used in the present invention is a function describing energy as a function of positions of atomic centers of a molecular model with respect to one another. Energy is measured by a sum of harmonic and anharmonic terms that include bond stretching, angle bending, linear deformation, out-of-plane deformation, dihedral torsion, Van der Waals interactions, electrostatic (Coulomb) interactions, hydrogen bonding interactions, and user/application constraints.

The implementation in the present invention is as follows:

(a) Bond Stretching:

$E_B = K \cdot (r - r_0)^2$ $E_B$ is the energy due to bond stretching or compression. K is the force constant. The equilibrium bond length is $r_0$ and the current actual bond length is r.

(b) Angle Bending:

$E_A = H \cdot (a - a_0)^2$ $E_A$ is the energy due to bending a bond angle. The equilibrium angle is $a_0$, and the current angle is a.

(c) Linear Deformation:

$E_{LB} = L \cdot (b - \pi)^2$ $E_{LB}$ is the energy due to bending a bond. L is the force constant. The actual deformation is b in angular units.

(d) Out-Of-Plane Deformation:

$E_{OOP} = W \cdot (W - W_0)^2$ $E_{OOP}$ is the energy due to out-of-plane deformation. W is the force constant the current out-of-plane angle is $w_0$. The equilibrium out-of-plane angle is w.

(e) Dihedral Torsion:

$E_{DH} = Y(1 - \cos(n \cdot t - d))$ $E_{DH}$ is the energy due to dihedral torsion. Y is the force constant. The periodicity of the dihedral torsional motion is n. The position of the first minimum is d. The current actual dihedral angle is t.

(f) Van der Waals interactions:

$E_{VDW} = 4 \cdot e_{AB} \cdot ((S_{AB}/r_{AB})^{12} - (S_{AB}/r_{AB})^6)$ $E_{VDW}$ is the energy due to Van der Waals effects. $e_{AB}$ is the energy of the minimum (deepest) point on the Van der Waals curve for the atom pair AB. $S_{AB}$ is the separation distance between the atom pair AB at the energy minima. $r_{AB}$ is the current actual distance between atom A and atom B.

(g) Electrostatic Interactions:

$E_{ELECTRO} = (q_A \cdot q_B)/(4 \cdot \pi eps_0 \cdot diel \cdot r_{AB})$ $E_{ELECTRO}$ is the energy due to electrostatic interaction. $q_A$ is the charge on atom A. $q_B$ is the charge on atom B. $eps_0$ is the dielectric permittivity of a vacuum. Diel is the relative dielectric of the system. $r_{AB}$ is the distance between atoms A and B.

(h) Hydrogen Bonding Interactions:

$E_{Hbond} = (C_{ij}/(r_{ij})^{12} - D_{ij}/(r_{ij})^{10})$ $E_{Hbond}$ is the energy due to hydrogen bonding interaction. $C_{ij}$ is the attraction consent for the atom pair ij. $D_{ij}$ is the repulsion constant for the atom pair ij. $r_{ij}$ is the distance between the donor atom i and the acceptor atom j. The donor atom i is the heavy atom that typically has the hydrogen being used in the H-bond, and the acceptor atom j is the atom (usually an electronegative atom) that is attracting the donated hydrogen.

(i) Constraints:

Constraints are most conveniently introduced by defining a duplicate internal coordinate and assigning it a very large force consent. This has the advantage that the derivatives of the function are well behaved and no new machinery/code needs to be developed. Since the force constant and equilibrium geometries are not determined by the topology, the atoms that make up the constraint coordinate need not be topologically connected. For example, one could constrain three atoms to have a more-or-less constant relationship in space by defining two constraint "bonds" and one constraint "angle" by an arbitrary pairing of the triplet of atoms.

The overall energy function is the sum over all internal coordinates of the relevant energy terms listed above. That is, the sum over all bonds of the bond stretch term, plus the sum over all angles of the angle bending term, and so forth.

Each term in the force field is analytically differentiable with respect to atom coordinates. Since the derivative of a sum is the sum of the derivatives, the gradient of the force field with respect to an atom's coordinate (for example the x coordinate of atom 7) is the sum of the derivative of each term in the force field with respect to that coordinate.

The functional form and the coefficients and exponents used in the force field are determined by fitting curves to empirically determined energies of molecular conformations.

The force field function must be continuous and everywhere differentiable to be suitable for PBM. Gradients can be computed from analytical derivatives of the force field function or by numerical differentiation. To optimize the numerical stability of the method, and to improve response time, analytical gradients are used wherever possible.

If N is the number of atoms in a molecule, any coordinate representation of a rank greater than or equal to 3N−6 will suffice to describe a conformer of the molecule. Any such coordinate system can be converted into any other by a linear transformation. The strains on a molecule are displayed in terms of the molecule's "internal coordinates", which (again) consist of bond stretches, angle bends, dihedral rotations, out-of-plane bends, hydrogen bonds, Van der Waals interactions, and electrostatic interactions. The gradient of the energy, as computed from the force field, is a vector in terms of the coordinates of a basis. Since the system "knows" the relative contribution of each coordinate in one basis, and since a linear transformation suffices to convert the force field's coordinate system into an internal coordinate system, the system can compute the relative magnitude of the gradient component of each internal coordinate to represent its strain.

The number of non-bonded interactions, such as Van der Waals and electrostatic interactions, rises as a quadratic function of the number of atoms in a molecular model, while the number of other internal coordinates, such as bonds and dihedral rotations, rises only linearly with the number of atoms. For this reason often 90% or more of the time spent in energy and force evaluation is concerned with evaluation of non-bonded contributions. This is particularly true for molecules with fewer than about 100 atoms, which includes most pharmaceuticals, because "cutoff" methods practiced in the art are not usable. Cutoff methods ignore non-bonded interactions between atoms that are far enough apart that their contribution to the non-bonded component of energy may be considered negligible. For molecules with fewer than about 100 atoms, all are typically within such a threshold range.

To minimize computation time in accounting for non-bonded contributions, fast non-bonded calculations are essential, and are an important feature of the present invention. This is done by a method called "Fast Van der Waals" calculations in this specification.

A Morse potential, which takes the form:

$$A^*e^{-Br} - [C/r^6]$$

where A, B, and C are consents dependent on the particular atoms and r is the distance between a pair of atoms, is a physically justifiable functional form of the Van der Waals potential. Most force fields approximate the Morse potential by using a so-called 5–10, 6–9, or 6–12 potential. The 6–12 (or Lennard-Jones) potential is of the form:

$$A/r^{12} - B/r^6$$

The 6–12 potential is the function used in the preferred embodiment and models the Morse potential (and hence the Van der Waals potential) quite well throughout its range. With this form, one may exploit the fact that $r^{12}$ is $(r^6)^2$ to speed the calculation as well. The system in the preferred embodiment improves on the straightforward 6–12 potential calculation by unique table look-up methods.

Table lookups for the Fast Van der Waals evaluations are based on a three-dimensional table indexed by the atom type of one atom in a pair, the atom type of the other atom of the pair, and bins based on the squared interatomic distance. With one atom at position i and the other at position j, the squared interatomic distance is quick to compute as:

$$r^2 = (x[i] - x[j])^2 + (y[i] - y[j])^2 + (z[i] - z[j])^2$$

Since Van der Waals energy may be considered insignificant beyond some cutoff, about 8 Angstrom units, interesting squared distances between 0 and the squared cutoff distance of 64 Angstroms are calculated and stored in narrow bins without too much computer memory. The three-dimensional table is indexed by the atom type of atom 1, the atom type of atom 2, and the squared interatomic distance, and the Van der Waals contribution to overall energy (with reasonable resolution) of any pair of atoms within the threshold distance is thus computed and stored.

Alternatively the third dimension for the three-dimensional table for Fast Van der Waals evaluations is based on interatomic distance alone, as each bin for squared interatomic distance is associated with a specific interatomic distance.

Figure 16:
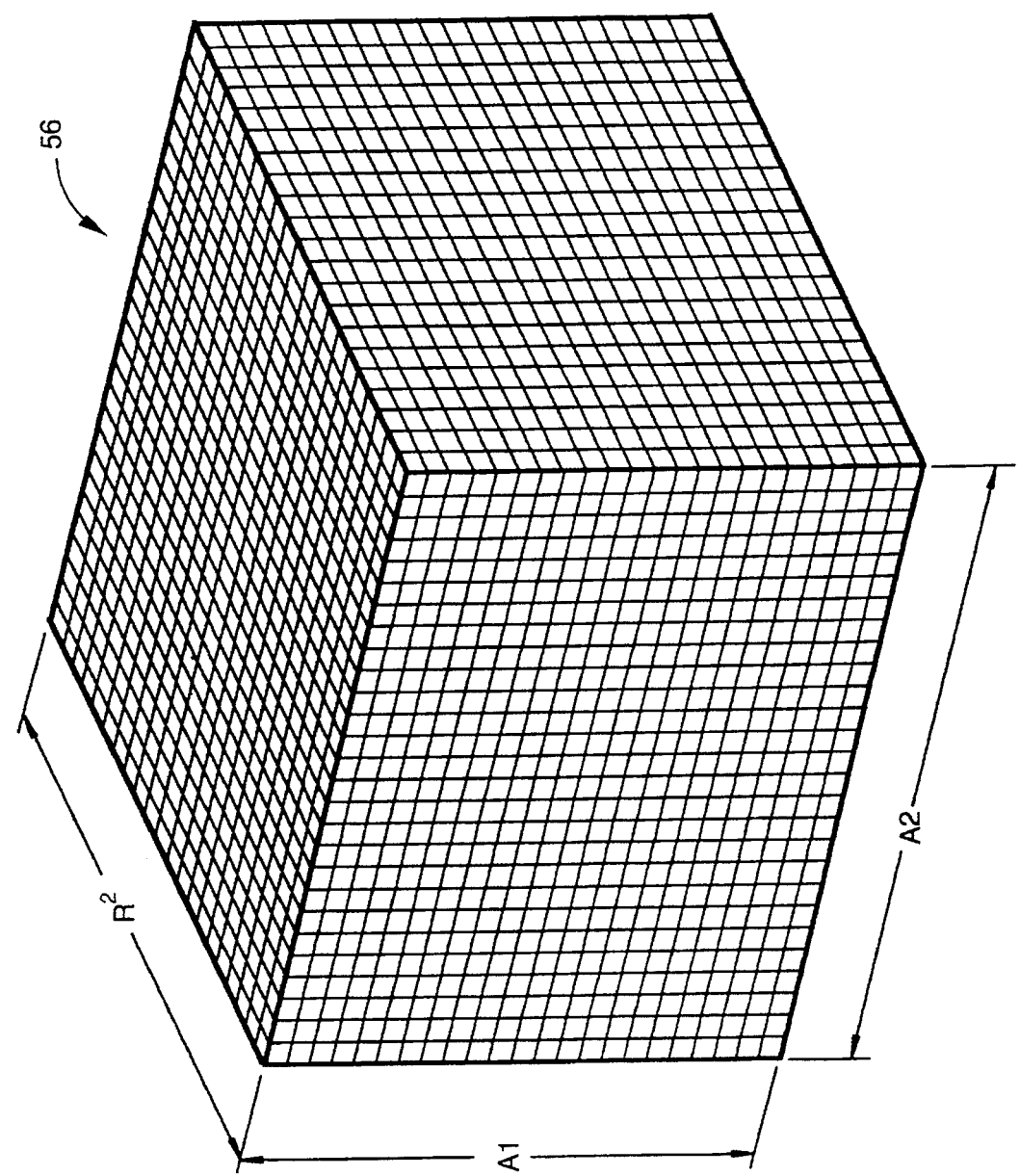
FIG. 16 is a representation of a table in three dimensions.

FIG. 16 is an illustration of a three-dimensional table 56 indexed by the atom type of one atom (A1), the atom type of the second atom of a pair (A2), and squared interatomic distance (R2). On the two-dimensional A1–A2 face of the three-dimensional table, there is a "square" for each possible combination of two atoms (although only representative squares are shown in FIG. 16), so every possible combination of two atoms is represented. Then, in the $R^2$ direction, there are bins representing squared interatomic distance, from zero to 64 angstroms$^2$, in (for example) increments of 0.0001. Associated with each "cube" in the three-dimensional array is a pre-calculated value based on (for example) the Van der Waals function. In evaluating the Van der Waals contribution to energy for a simulated molecule the system must calculate for each atom the Van der Waals component with every other atom.

A three-dimensional table for a computer system is not the same as the array shown in FIG. 16, but involves a series of memory tables with fixed addresses. Given an atom, the system must go to the address beginning the memory array for that atom type, and index to the address assigned for the second atom type. The entry at that location is the beginning address for a one-dimension array of pre-stored Van der Waals energy values indexed by squared interatomic distance. The system then goes to that array, and given the index value, fetches the unique pre-stored energy value for that particular atom pair and squared interatomic distance. Typically, for a three-dimensional table look-up in a computer memory system there are two integer multiplications and an integer addition.

The system in the preferred embodiment improves on the three-dimensional table look-up based on the fact that the calculations are performed for relatively fixed composition simulated molecules. In the course of an investigation, it is typical for an investigator to build (or import) a molecular model, and then to spend some time perturbing the molecule to investigate the effects of changing conformation. For a particular molecular model, which may have only a few atom types of all the possible choices from the periodic table, there are a fixed number of atom pair and type combinations, and this is a small number compared to all the possible pairs.

The system takes advantage of this typical procedure and builds a table of the atom pairs for a molecular model and associates with each a flag pointing to the one-dimensional array of energy values indexed by interatomic distance unique to that pair. Two integer multiply instructions that are otherwise required to look up an entry in a three dimensional table in an addressed computer memory space are thus avoided. The combination of the table of atomic pairs and the stored pointer speeds up the Van der Waals energy evaluation by about a factor of five compared to straight calculation without table look-ups. This shortcut helps to make "on-the-fly" energy evaluation practical for PBM modeling.

Figure 17:
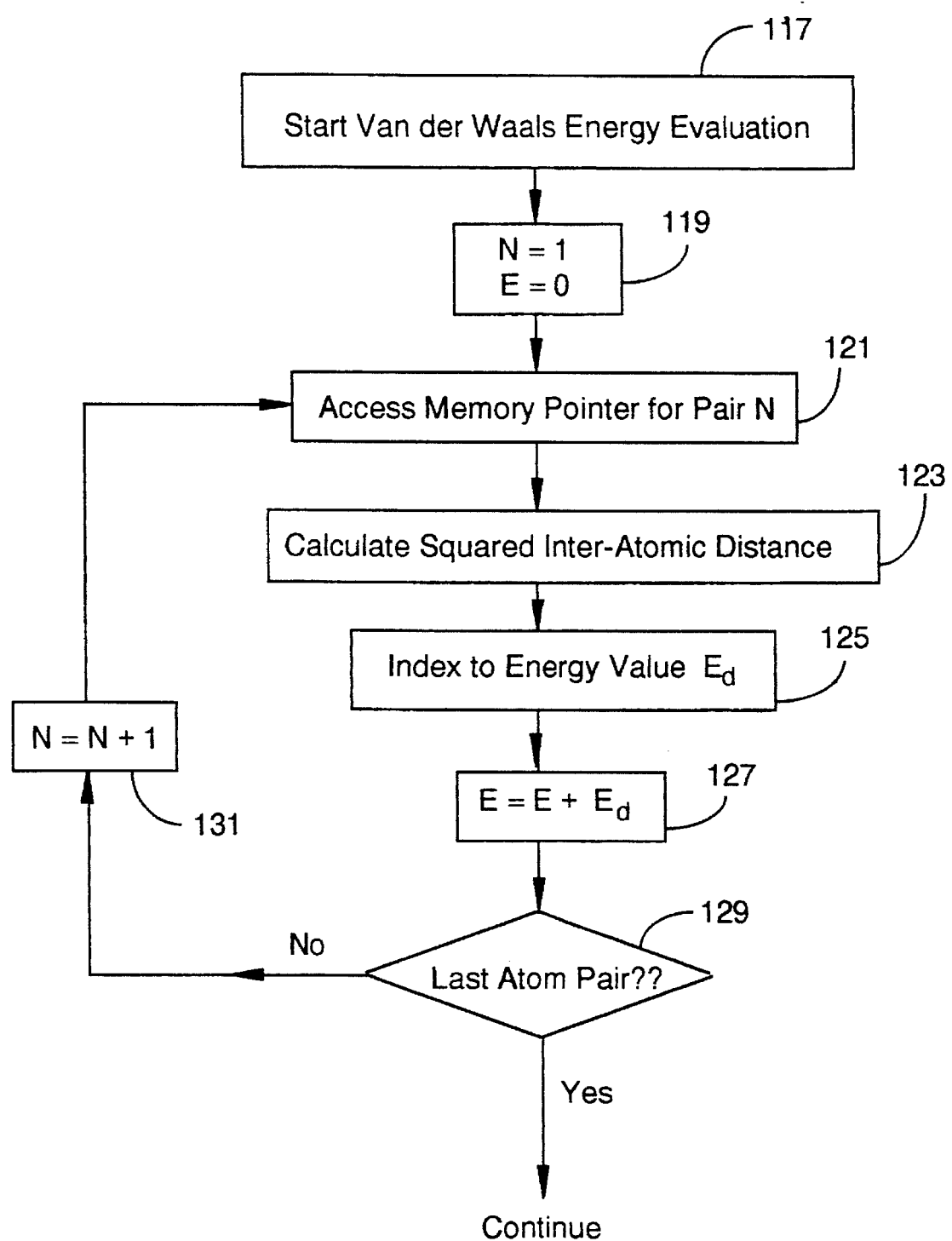
FIG. 17 is a flow diagram illustrating a method for the system controller to perform evaluations of a Van der Waals function.

FIG. 17 is a flow diagram showing the computational flow for the system evaluating Van der Waals energy components for the atom pairs of a simulated molecule of N atoms. The routine starts at 117 and sets N=1 at operation 119. The system accesses the pointer for pair N (121), calculates the square of the interatomic distance (123), and indexes to the stored energy value for that squared distance (125). The system adds that value to the total energy term being calculated at operation 127, then checks in operation 129 if the routine has been performed for the last pair. If so, the total energy is stored and the operation continues. If not, N is indexed by 1 in operation 131 and the look-up is done for the next atom pair in order in the table of atom pairs.

The Van der Waals gradient evaluation and electrostatic energy and gradient evaluations are similar to the method described above for the Van der Waals energy evaluation, but are somewhat more intricate. If f represents the 6–12 Van der Waals potential, the derivative of f with respect to r is:

$$df/dr=(-6/r)*(f+Ar^{-12})$$

The system uses three tables to evaluate the Van der Waals energy gradient: a table of $-6/r$; a table of $Ar^{-12}$; and the f table described for the Van der Waals contribution to total energy described above. Since $Ar^{-12}$ rises rapidly for small r, that table is binned relatively finely. Since $-6/r$ remains significant even for fairly large values of r, this table is made larger than the others. With these three tables, the 6–12 potential and its derivative can be evaluated in three table lookups, one multiplication, and one addition. In practice, the error introduced by the "binning" system is less than 1% throughout the range covered by the tables.

In an alternative embodiment two lookup tables are used: $r^{-6}$ and $-6/r$. With these two tables the function and the gradient can be evaluated in two lookups, two adds, and four multiplies. In yet another embodiment, one table based on the 6–12 potential is used, and the evaluation needs one lookup, two adds, and eight multiplies, and this is still significantly faster than direct calculation.

In PBM, there is a unique problem associated with how to display the geometric alterations to a molecular model as a result of a user-induced perturbation. The problem is what to hold stationary with respect to the user's viewpoint, and what to move. If a simulated molecule is treated as a rigid whole, for example, and one selects an atom and moves it by the knurl presented, the whole molecule will move as a unit without alteration in geometry. Something must be held stationary for PBM to work. The same reasoning holds for molecular manipulation with PBM turned off, and the rules developed for what to hold stationary to the user's viewpoint and what to allow to move apply to both situations.

There are a very large number of choices. A center for the molecule could be defined, for example, and movement of all atoms could be calculated relative to that defined center held immobile. Also, one or another of the atoms in the molecule might be selected to be the fixed point around which relative movement is displayed.

In the preferred embodiment, user-induced perturbation is displayed in a manner that mimics what would be expected for a physical model that follows known physical laws. To build a physical model that even approximates such a state with springs and such is prohibitively difficult and expensive, and once done, cannot easily be changed, for example, into even a closely related molecule, without considerable difficulty. With the aid of computers and three-dimensional display, such a model can be readily available for investigation, and moreover, can be instantly changed as investigation warrants. The problem is to account for all of the physical laws in a manner that allows the use of a "reasonable" computer platform, and does so with sufficient rapidity to simulate "real time" perturbation.

Figure 18:
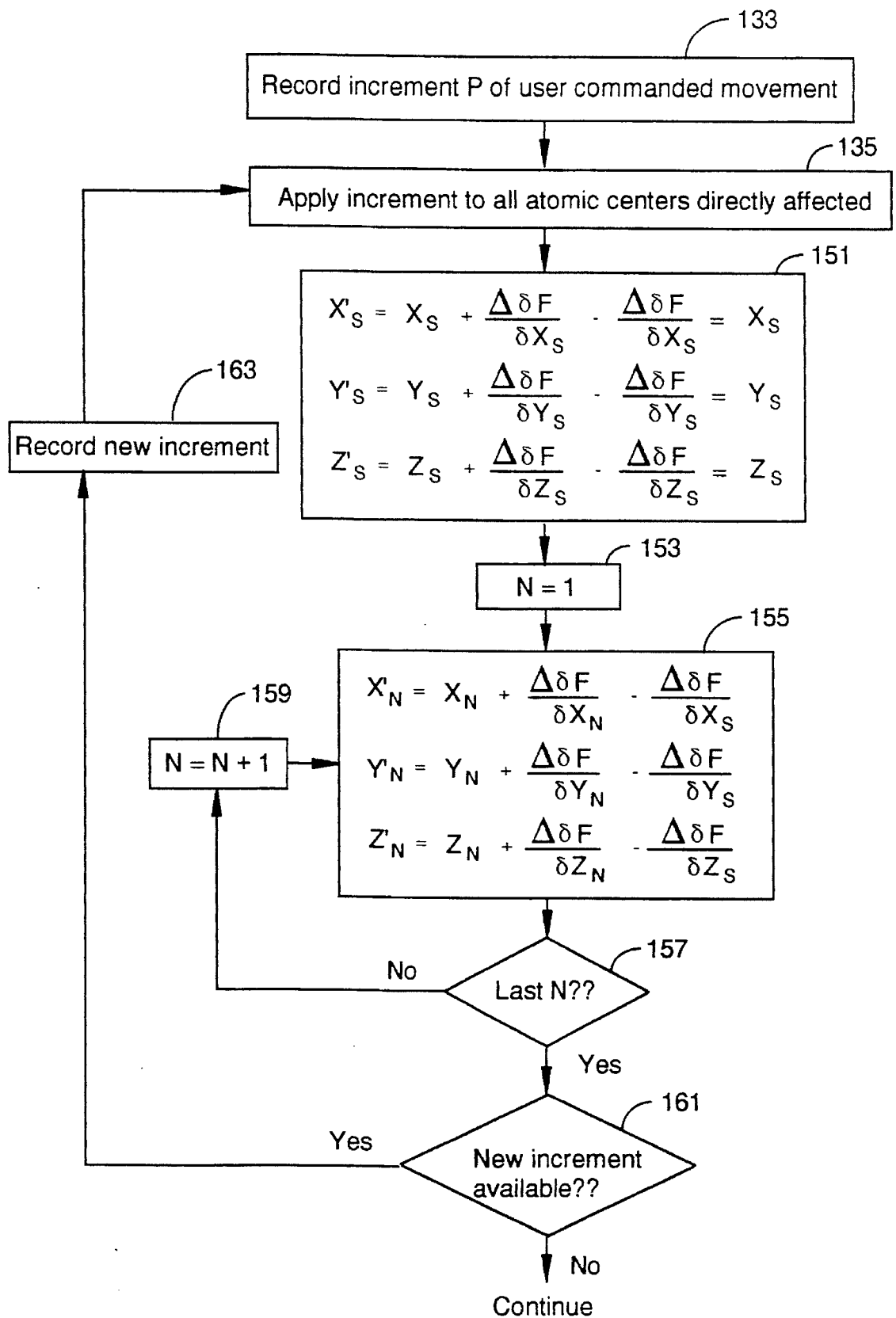
FIG. 18 is a flow diagram illustrating a method the system controller uses to determine movement of atomic centers when a user perturbs the geometry of a model of a molecule.

FIG. 18 illustrates the method by which the system in the preferred embodiment calculates and displays geometric perturbations in PBM. First, a user manipulates a knurl. The system tracks the user's direction with the cursor for a predetermined time (operation 133) and records the incremental move. The time can be a constant in the routine or another time interval, such as one clock cycle for the particular computer platform being used. The system then applies that increment to all atoms directly affected by the cursor movement (operation 135).

In selecting the atoms to be moved directly, the system follows simple rules. For example, a user may select a rotational knurl on a bond. If the group structure to either side of the knurl may be rotated, the system presents two knurls. To rotate the structure to one side, the user selects the knurl closer to that side. To rotate the other side, the user selects the knurl closest to the other side.

The rule for rotational knurls is that both atoms attached to the rotated bond remain stationary to the user's eye, just as would be the case if the user had a physical model, and held the two atoms one in each hand, and twisted. On the side that rotates, the system moves each atom directly affected by the rotation, keeping the interatomic distance from the moved atom to the atom attached to the rotating bond on the rotating side constant.

The rule for a stretch knurl is that all atoms to the side of the bond as the knurl move in the direction the user moves the cursor. Again, the increment applied in the routine is determined by the user's movement of the cursor in a pre-determined interval, such as a single clock cycle for the computer equipment. This is intuitively the same as though the user "grabs" an atom in one hand, then pulls (with the other hand) another atom bonded to the first to stretch the bond.

Figure 19:
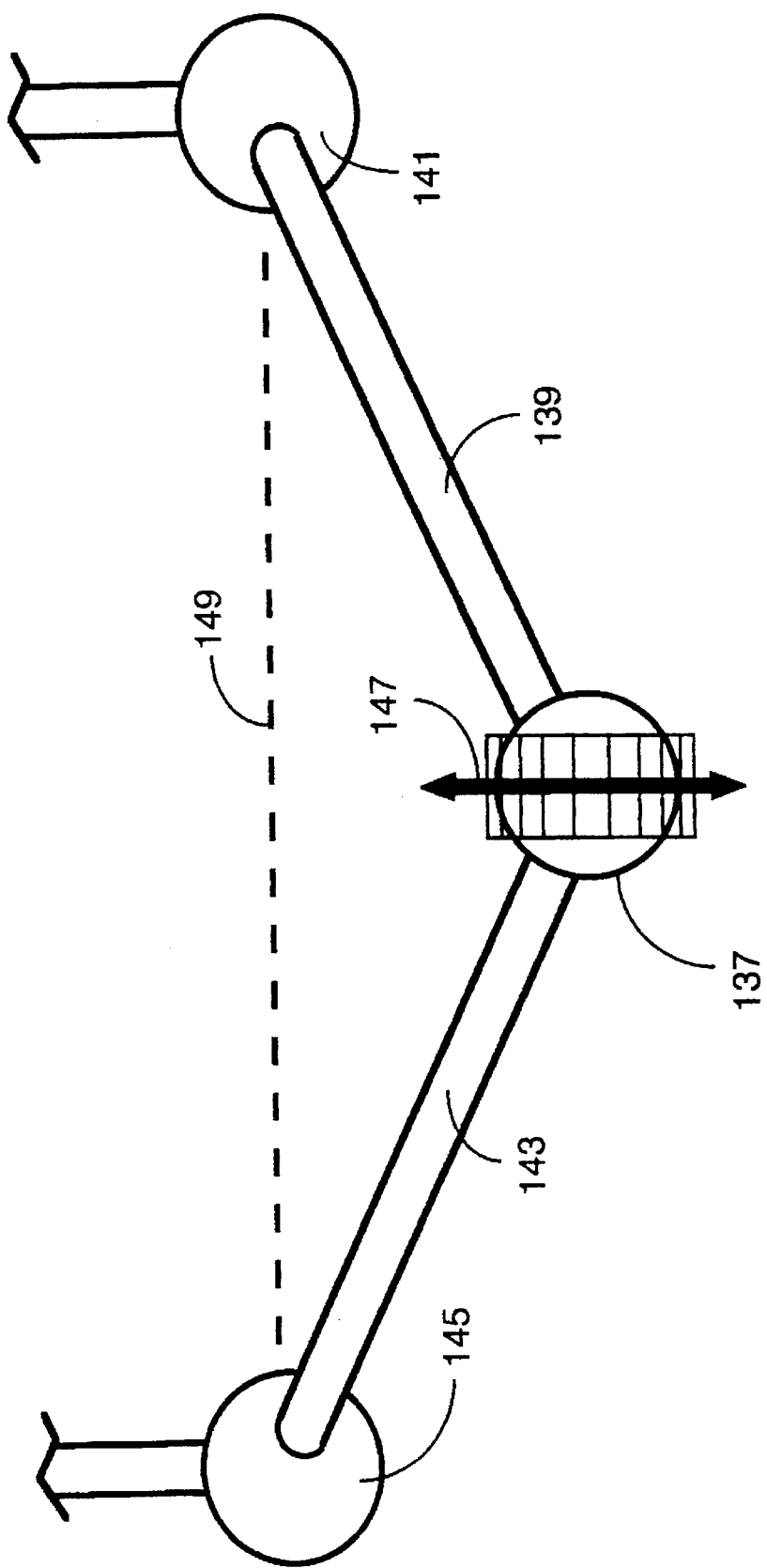
FIG. 19 shows a method of perturbation wherein an atom in a model is moved around a rotational axis between adjacent atoms of the model.

For a ring structure, where a user selects an atom for which the system displays an atom knurl, the rule is relative to the two atoms bonded to the atom selected. FIG. 19 illustrates this case. Atom 137 is selected and displays a knurl. Atom 137 is attached by bond 139 to atom 141 in a ring structure and by bond 143 to atom 145 in the same structure. Arrow 147 indicates the direction a user moves the knurled atom by action with the cursor. In this case the system establishes a rotational axis 149 between the two atoms attached to the atom perturbed, and holds this axis stationary relative to the user's viewpoint. The system "knows" the coordinates of the two atoms joined by bonds to the atom moved, and can thus determine a straight line between the two as a virtual axis. All other atoms may move in the display relative to this stationary axis. It may be true in evaluating interatomic forces that the distance between the two atoms at the ends of axis 149 will change, and if so, the system moves each by the same amount. In the case of FIG. 19, the only atom directly affected by the knurl-induced movement is atom 137.

Returning to FIG. 18, after the system applies the incremental movement to all the atoms directly affected, it updates all the forces and energy terms for each atomic center in the simulated molecule, calculates gradients, and applies changes in position relative to the display rules. In operation 151 the system calculates the displacement for the atom(s) that are to remain stationary, and this operation illustrates the heart of the calculation method for an intuitive display. $X'_s$ is the "new" x coordinate for the stationary atom. $X_s$ is the "old" x coordinate. The movement added is the partial derivative of the field function F with respect to the x direction at $X_s$, multiplied by a small step size shown as upper-case "Delta" in the calculation. Then the same movement is subtracted so the new X coordinate is the old X coordinate. The same calculation is done for the Y and Z coordinates for the stationary atom(s).

In the calculation shown as operation 151 Delta is the step size described above, wherein the system integrates the differential equation represented by the incremental gradients to anticipate the user's next move as a function of a sequence of recent gradient calculations. As described above, this is a technique that has been used in flight simulation equipment in the absence of more powerful computers. Well known integration techniques such as Bulirsch-Stoer and predictor-corrector techniques are used.

In operation 153 the system sets a flag to begin to index through all the atomic centers for the simulated molecule, except the center(s) that is to be stationary. In operation 155 the system calculates the displacement for an atomic center depending on the flag "N", and subtracts the displacement calculated in operation 151 for the atom to be held stationary for the user's viewpoint. In operation 157 the system checks if all atomic centers have ben calculated. If not, the flag is indexed and the next atomic center is calculated. If all the atomic centers have been calculated, the system checks in operation 161 if there has been additional cursor movement. If so, the system records the new increment in operation 163, and readjusts all atomic centers by repeating the routine. If not, control returns to the general control flow, typically to await new user input.

The routine loops illustrated by FIG. 18 illustrate just one procedure flow for maintaining stationary atomic centers. A person with skill in the art will recognize there are equivalent techniques for accomplishing the routine, but the routine is unique.

Figure 25:
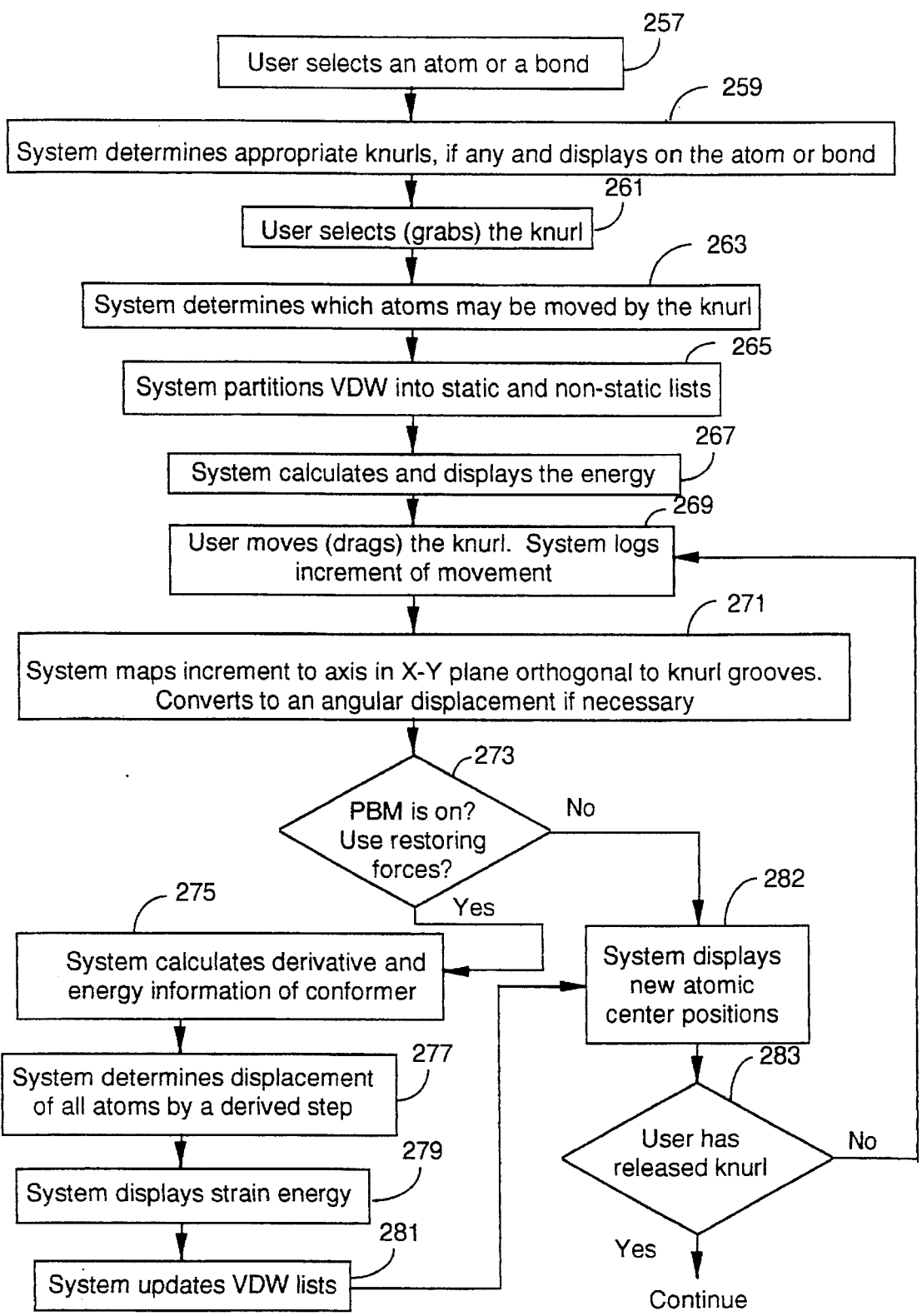
FIG. 25 is a flow diagram illustrating the procedure for perturbing the geometry of a model of a molecule with physically-based modelling turned on and turned off.

FIG. 25 is a flow chart illustrating the procedure of PBM. In step 257 the user selects an atom or bond. In step 259 the system displays in response to the selection, any appropriate knurl on the atom or the bond. Although only knurls are referenced in FIG. 25, there is also a case where the system displays a handle projecting from an atom in response to a selection.

In step 261 the user moves the cursor to the knurl and "grabs" the knurl. The system then determines which atoms may move in the display, and which may not (step 263). The system partitions the atomic center pairs into static and non-static lists for VDW determinations in step 265. In step 267 the energy is calculated from the force field energy function. At step 269 the user drags the knurl to perturb the geometry of the molecule.

The system tracks the user's drag motion for a period of time and maps an increment to an axis in the x-y plane orthogonal to the knurl grooves, and does any conversion to angular displacement that is necessary (step 271). Decision step 273 determines if PBM is turned on. If it is, the derivative is determined and energy information is calculated and displayed in step 275. In step 277 the system displaces all atomic centers by a derived step for each. This step is illustrated in more detail in FIG. 18, which is described above. In the case of atomic centers that are held stationary by design, the derived step is zero.

In step 279 the system displays the strain energy, which is the energy added to the molecule by the perturbation. In step 281 the VDW lists are updated according to the new atomic center positions. The system displays the new atomic center positions in step 282, then queries in step 283 if the user has released the knurl. If Yes, the control flow continues out of the sequence of FIG. 25. If not, control returns to step 269, and another increment of movement of the knurl is logged, and subsequently used for further determinations.

If at step 273 PBM is turned off, the mapped knurl motion is used to determine the displacement of the movable atoms directly, using geometric rules stored in the memory, the new atomic center positions are displayed in step 282, and control goes to decision step 283.

Docking

It is known in the art that many chemically-based phenomena (e.g. adhesion and drug response) are facilitated by an association between molecules called docking, wherein two or more molecules come into close proximity as a result of similar surface shape and chemical characteristics, rather than through covalent bonding. In the preferred embodiment a facility is provided for a user to investigate docking characteristics between molecules.

There is no restriction in the system to the simultaneous display and manipulation of only one molecule in the 2D/3D window. More than one may be displayed. One can select molecules from a data base for display, or even build multiple molecules on the screen. Once two or more molecules of interest are represented in the display, docking characteristics are investigated by bringing the molecules into proximity in a pair-wise fashion and noting the force and energy perturbations that result. The system uses the same techniques described above, such as fast Van der Waals calculations incorporating table look-ups, to speed the process and minimize the computing power required.

There are two methods that may be used for docking studies, one wherein inputs are made via the three-dimensional display, and the other using the two-dimensional display for input. The three-dimensional technique employs the rotation and translation tool for positioning and moving molecules on the screen.

Figure 20:
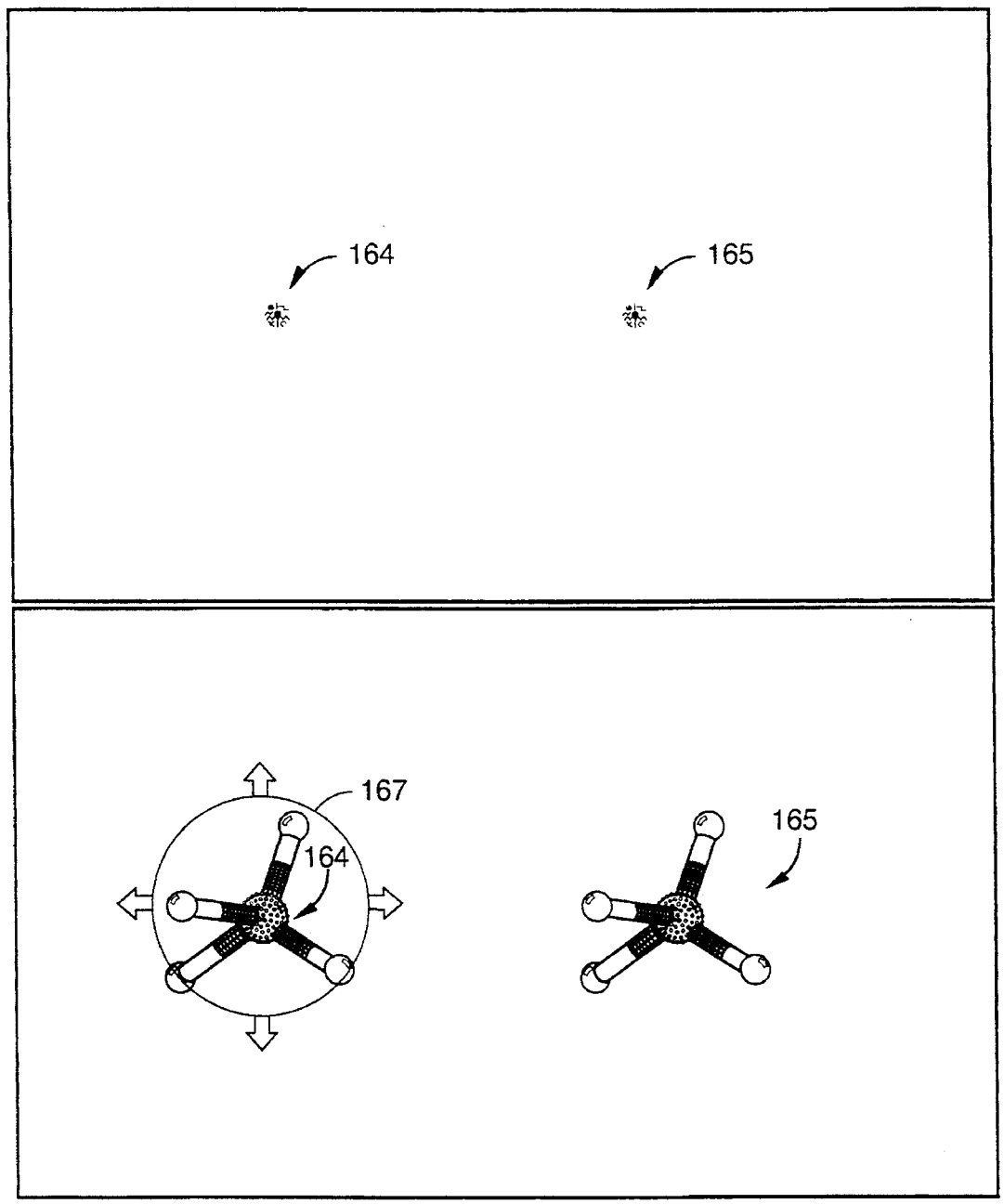
FIG. 20 is an annotated screen print of a display showing two models of molecules opposed in a docking investigation using the three-dimensional display.

FIG. 20 shows two methane molecules 164 and 165 as an example, even though these would not be likely candidates for a docking study. They are small enough to be easily rendered to illustrate the techniques used in docking.

In the default operation in the preferred embodiment energy evaluations may be performed by the system as one builds a molecule, and force and strain are calculated and displayed as one perturbs the geometry of a molecule in some fashion by manipulating knurls that are displayed on bonds and atoms, as described above. In a docking investigation of the first type, one does not select a bond or atom, so the system does not "know" to display a knurl or enable the energy and force evaluations performed when one distorts the geometry of a molecule. In the preferred embodiment this drawback is overcome by a keystroke signal to the system to enable a docking operation. Any one of several keystroke signals may be assigned for the purpose.

Once there are two molecules displayed, and a docking investigation is enabled by the appropriate keystroke signal, the system "knows" to perform the required calculations as an investigator moves one or the other (or both) molecules. FIG. 20 shows two methane molecules ($CH_4$) 164 and 165 with the system enabled to do docking. Molecule 164 shows a rotation and translation sphere 167 the same as described above with reference to element 49 in FIG. 9A, used in the preferred embodiment to rotate and translate molecules in three dimensions. With docking enabled the investigator may rotate and translate the molecule showing the sphere tool, and may alternatively select the other molecule to transfer the sphere tool to that molecule. By selectively rotating and translating the investigator may move the molecules into proximity, much as one would bring together and orient two transparent balls containing and holding the respective molecules. The rotate and transfer tool, although displayed, is not a part of the molecular structure, but a virtual indicator, and does not interfere with any part of a molecule.

When one distorts the geometry of a molecule by manipulating a knurl, the system has to track the "knurl motion" the user supplies by the input device, and then calculate the changes in energy, the restoring forces, and the changes in conformation of the atomic centers as a result of the restoring forces for the single molecule. For docking, the case is a little different. What is of primary interest are the interatomic interactions (forces) due to Van der Waals and electrostatic effects between atoms of the respective molecules, which have no covalent bonds between them.

The situation in docking is that all the atoms of one molecule, until the investigator moves the molecules quite close, are generally well beyond a threshold distance (i.e for Van der Waals and electrostatic interactions) from the atoms of the other molecule, and the interatomic forces may be safely assumed to be negligible. This is because the force contributions from the 6–12 potential as described above in the force field description under the section titled "Physically Based Modeling" approach zero very rapidly with distance. This threshold is substantially the same as for the case of the atoms of a single molecule, about 8 angstroms. As the investigator rotates for position and translates the molecules toward one another, the distances change. As they come within the threshold distance, the system calculates the forces, and if necessary perturbs the atomic center positions within each molecule as a result of forced movement of one or the other molecule by the investigator. That is, an investigator may affect an intimacy between the two molecules that will cause the repulsive and/or attractive forces between atoms of one molecule and the other to be great enough to cause angle stretches, bends, etc., changing the conformation of one or both of the molecules. The evaluations are the same as described above for the force-field in physically based modeling. The idea in docking studies is to investigate whether two molecules can be induced to "fit together" with no repulsion, or even with a net attraction, and without strain within either molecule.

The routine in the calculations for docking is much like the routine shown for the deformation case by manipulating knurls, detailed in FIG. 18, except the increment of user movement is not the movement applied to a knurl, but the movement of an entire molecule (all atoms) relative to atoms of another molecule using the translation and rotation tool. The atomic centers directly affected in the case of translating one molecule toward another are all the atomic centers of the molecule translated. This is not very different from the case of stretching a bond in a single atom, for example, in which case all of the atoms to one side of the bond are translated in the same direction.

As in the case of the single atom being deformed, the atomic centers to be held stationary are designated by a simple rule, which in the case of docking in the preferred embodiment is that all the atomic centers of the molecule not translated are held stationary. Different rules may be applied in alternative preferred embodiments. This is done in the same manner as described in the routine of FIG. 18, by subtracting any incremental move calculated for an atom held stationary by the rule, from the motion of atoms not held stationary.

In docking, the resisting force of the stationary molecule to closer proximity of the moving molecule is displayed as strain, and audio feedback is used as well to indicate the "steepness" of the gradient.

A second and more automatic method for docking investigation is provided through input in the two-dimensional display. There is a distinct advantage to using the two-dimensional display to initiate a docking investigation, because the geometry in two dimensions can be stylized. That is, one may relocate atomic centers in the molecules of interest in the two-dimensional display to expose the particular parts of a molecule that are of particular interest in a docking investigation.

Figure 26:
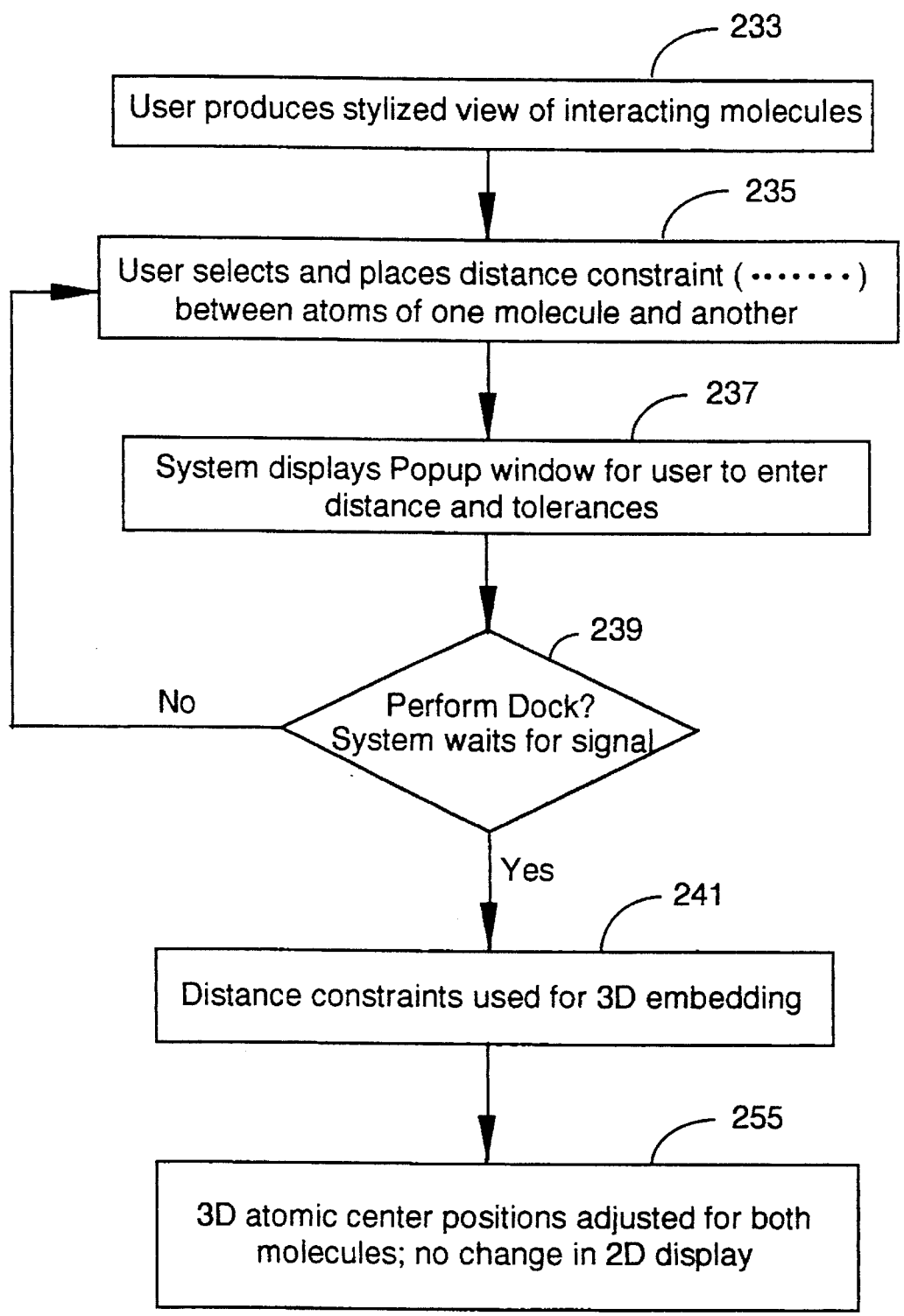
FIG. 26 is a flow diagram illustrating the procedure for performing a docking investigation using the 2 display for entering constraints.

FIG. 26 shows the sequence of steps in a docking study by the method of entering constraints in the two-dimensional display and studying the results in the three-dimensional display, where the system moves the molecules, if possible, into the specific proximity established by the entered constraints.

At step 233 the user produces a stylized two-dimensional view of two (or more) molecules of interest for a docking study. The molecules can be recalled from memory or assembled in the display, and the user may move atoms around with the aid of two-dimensional drawing tools to best show atoms in the area of the molecules where docking is to be investigated.

In the next step (235) the user selects a distance constraint tool from a pull down menu, and selects two atoms, one on each molecule. The purpose is to impose a distance constraint, and the system displays a dotted line between the two selected atoms after the second atom is selected. After the selection of the two atoms, the system displays a Popup window on the display for entry of a distance constraint to be applied between the two atoms just selected. This is step 237. The Popup window is an entry field, and the user may enter a distance, typically in angstroms. The system also allows the user to enter an upper and lower tolerance for the constraint, also typically in angstroms. For example, a user may enter 7 angstroms, +2, −1 angstrom. If the user does not enter tolerances the system uses a default tolerance, typically ½ angstrom upper and lower.

At least one set of atomic centers must be selected before docking can be performed. In step 239 the system presents an opportunity for docking to be initiated. The user does this by selecting from a pull down menu. Alternatively, the user can enter more constraints between more atoms in the molecules displayed, and enter distance constraints and tolerances for each. After each entry of a new constraint there is another opportunity to initiate docking at step 239.

Figure 21:
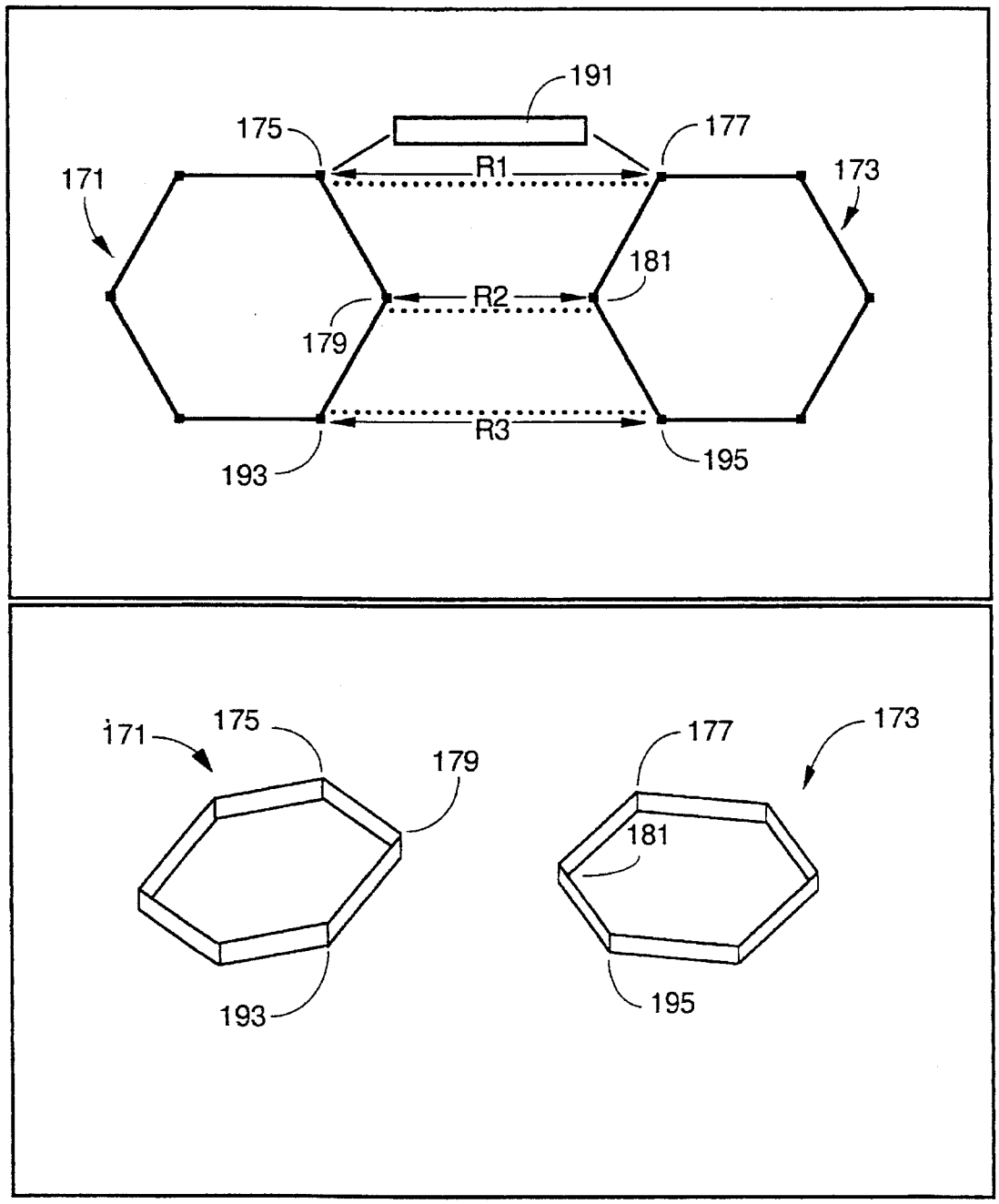
FIG. 21 shows two ring structures in a docking investigation using the 2 display for entering constraints.

FIG. 21 shows two molecules 171 and 173 in the two-dimensional display, and three sets of constraints entered, between atoms 175 and 177, 179 and 181, and 183 and 185. Entry field 191 represents the Popup window described above. Distances R1, R2, and R3 are the distance constraints. The dimensions are not shown in the display, except when entered in the Popup window.

When the signal described above to enable the docking function is received the system determines new atomic center positions within the constraints entered by the user. If the constraints are not reasonable, and the molecules cannot be put in the new position, the system displays the closest approximation it can. The process is one of three-dimensional embedding represented by step 241 and shown in additional detail in FIG. 27.

Figure 27:
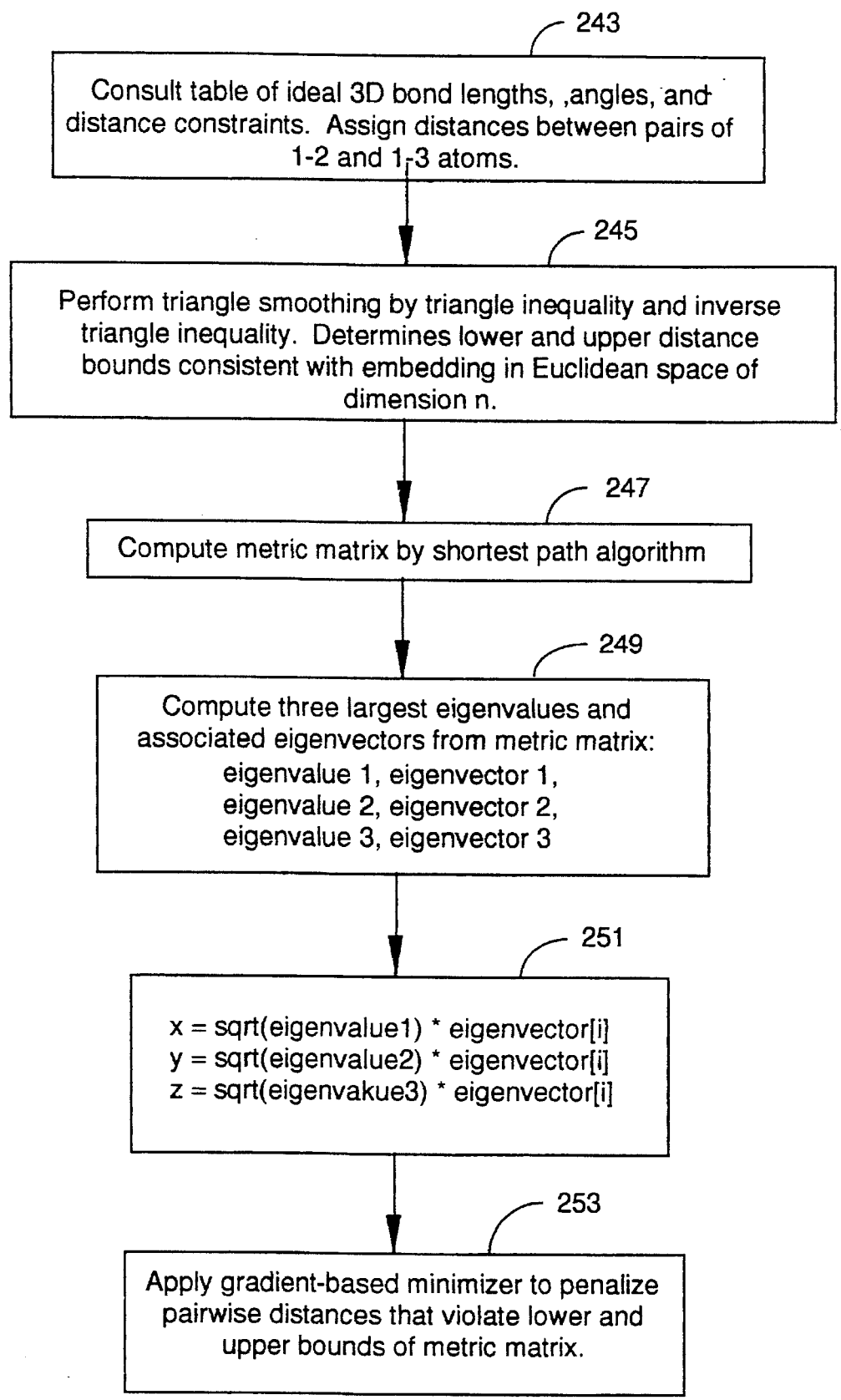
FIG. 27 is a flow diagram illustrating the process of three-dimensional embedding.

In FIG. 27, step 243, the system consults stored tables of ideal three-dimensional bond lengths and angles, obtains inter-molecular distances from the constraints put in by the user (see above), and assigns distances between pairs of 1–2 and 1–3 atoms. In step 245, the system does triangle smoothing of the assignments in step 243. In step 247 the system computes the metric matrix by a shortest path algorithm. In step 249 the system computes eigenvalues and eigenvectors. In step 251 the system computes the three-dimensional coordinate (for each atomic center). In the final embedding step 253 the system applies a gradient-based minimizer as a final adjustment to the atomic centers.

Returning to FIG. 26, after the three-dimensional embedding process, the system displays in three dimensions (step 255) the molecules in their new positions imposed by the entered constraints. There is no change in the two-dimensional display.

This method, entering constraints in the two-dimensional display and displaying the docking result in three dimensions, besides being more automatic than the first method described, also takes into account that an experienced investigator may have definite clues to docking configurations, and information to lead to experimental values for inter-atomic distances.

In many molecules of interest for a docking study there are a relatively large number of atoms, and the specific areas of interest where docking might occur may be obscured by molecular structure defining other areas of a molecule. With the aid of the stylization possible in the two-dimensional display a user can "push aside" the obscuring structure and get a better look at the areas of interest, and also define distances between areas of interest on two molecules.

It will be apparent to one with skill in the art that there are a large number of changes that may be made in the preferred embodiments of the invention without departing in any significant manner from the spirit and scope of the invention. One might, for example, separate the two-dimensional and three-dimensional windows on the screen, or even display one at a time, while maintaining a single data base. One might also maintain two copies of the, one to serve the two-dimensional display and the other to serve the three-dimensional display, but this would not depart from the spirit of the invention. There are also different ways that knurls might be displayed on parts of a molecule other than the specific examples provided in the description of the preferred embodiments, but that may be considered equivalent. There are also alternate ways known in the art for implementing the unique routines described, such as the Fast Van der Waals method of evaluating Van der Waals potentials. There are similarly many other alterations that can be made without departing from the spirit and scope of the invention. The scope of protection should only be limited by the scope of the broadest interpretation of the appended claims.

What is claimed is:

1. A computer graphics system to display a model of atoms and molecules and to investigate chemical and physical properties of said atoms and molecules comprising:

a processor;

a controller coupled to said processor to direct operations of said graphics system;

a memory coupled to said processor to store dam relative to known atoms and molecules, and intra-molecular forces between atoms in said molecules;

a monitor coupled to said processor to provide a display of information and said model of the user selected atoms and molecules from said data in said memory with a three-dimensional technique used by chemists to illustrate a relationship between atoms and molecules, said model displayed as graphical elements representing atoms located at atomic center positions with graphical coordinates of said atomic centers relative to each other stored in said memory, and connecting graphical elements between said atomic centers representing bonds therebetween; and a pointer manipulation device coupled to said processor to provide a user a capability to dynamically model said molecular model by selecting data relative to atoms and molecules from said memory for said model, to conformationally alter a molecular model, and to direct operation of said controller;

wherein said controller permits limited movement of an atomic center position with respect to the atomic center positions of other atoms within said model to dynamically model said molecular model by conformationally altering said three-dimensional displayed molecular model in keeping with said intra-molecular forces between atoms of said molecular model under the operation of said pointer manipulation device.

2. A computer graphics system as in claim 1 wherein said three dimensional models comprise one or more ring structures.

3. A system as in claim 1 wherein said controller, in response to user selection of a graphical element of one of said three-dimensional models, displays a pictorial manipulation element on said selected graphical element for a user to manipulate in order to move the selected graphical element to change the conformation of the atoms and molecules of said three-dimensional model.

\* \* \* \* \*